(12) United States Patent
Chatterjee et al.

(10) Patent No.: US 10,077,434 B2
(45) Date of Patent: Sep. 18, 2018

(54) NON-FUCOSYLATED PROTEIN AND METHODS THEREOF

(71) Applicant: Zumutor Biologics, Inc., Woburn, MA (US)

(72) Inventors: Sohang Chatterjee, Bangalore (IN); Kavitha Iyer Rodrigues, Bangalore (IN); Maloy Ghosh, Bangalore (IN); Sunit Maity, Bangalore (IN); Rajeshwari Pendse, Bangalore (IN); Divya Unnikrishnan, Bangalore (IN); Yogendra Manjunath B. M., Bangalore (IN); Jahnabi Arika, Bangalore (IN); Sathyabalan M., Bangalore (IN); Pavithra M., Kundapur (IN); Bhargav Prasad, Chennai (IN); Veeresha K., Bangalore (IN); Prabhat Kumar Pathak, Varanasi (IN); Sanghamitra Bhattacharjee, Bangalore (IN); Pravin Kumar D., Chennai (IN); Vivek Halan, Tamil Nadu (IN); Sankaranarayanan Srinivasan, Bangalore (IN); Anuradha Hora, Sitapur (IN); Bairavabalakumar N., Chennai (IN); Karthika Nair, Bangalore (IN); Aswini Thanigaivel, Chennai (IN); Amol Maliwalave, Bangalore (IN); Bharath R. Shenoy, Bangalore (IN); Anisha Kurup, Delhi (IN)

(73) Assignee: Zumutor Biologics Inc., San Francisco, CA (US)

( * ) Notice: Subject to any disclaimer, the term of this patent is extended or adjusted under 35 U.S.C. 154(b) by 0 days.

(21) Appl. No.: 15/500,509

(22) PCT Filed: Jul. 30, 2015

(86) PCT No.: PCT/IB2015/055777
§ 371 (c)(1),
(2) Date: Jan. 30, 2017

(87) PCT Pub. No.: WO2016/016842
PCT Pub. Date: Feb. 4, 2016

(65) Prior Publication Data
US 2017/0306305 A1    Oct. 26, 2017

(30) Foreign Application Priority Data

Jul. 30, 2014 (IN) .......................... 3728/CHE/2014

(51) Int. Cl.
C07K 1/00 (2006.01)
C12N 9/22 (2006.01)
C07K 16/00 (2006.01)

(52) U.S. Cl.
CPC ................ *C12N 9/22* (2013.01); *C07K 16/00* (2013.01); *C07K 2317/14* (2013.01); *C07K 2317/732* (2013.01); *C07K 2319/80* (2013.01)

(58) Field of Classification Search
None
See application file for complete search history.

(56) References Cited

FOREIGN PATENT DOCUMENTS

| WO | 2006089232 A2 | 8/2006 |
|----|---------------|--------|
| WO | 2009009086 A2 | 1/2009 |
| WO | 2013169802 A1 | 11/2013 |
| WO | 2014039585 A2 | 3/2014 |
| WO | 2014071039 A1 | 5/2014 |

OTHER PUBLICATIONS

PCT/IB2015/055777, "International Search Report and Written Opinion," dated Nov. 9, 2015, 11 pages.
PCT/IB2015/055777, "Written Opinion of the International Preliminary Examining Authority," dated Jul. 5, 2016, 6 pages.
PCT/IB2015/055777, "International Preliminary Report on Patentability," dated Sep. 28, 2016, 28 pages.
Kanda, et al., "Comparison of Cell Lines for Stable Production of Fucose-Negative Antibodies With Enhanced ADCC," Biotechnology and Bioengineering, Wiley & Sons, Hoboken, NJ, US, vol. 94, No. 4, Jul. 1, 2006 (Jul. 1, 2006), pp. 680-688.

*Primary Examiner* — Sean E Aeder
(74) *Attorney, Agent, or Firm* — Kilpatrick Townsend & Stockton LLP

(57) ABSTRACT

The present disclosure relates to developing cell lines where specific biological pathways are modified, particularly by modifications in the enzymes of the cell. The present disclosure develops protein expression systems wherein specific modification of glycan chain of the protein is achieved, which produces non-fucosylated proteins, including non-fucosylated antibodies. The non-fucosylated proteins are used in developing therapeutic monoclonal antibodies and biomarkers, and in diagnosis and prognosis of various diseases. The present disclosure employs the Transcription Activator like Effector Nuclease (TALEN) technology for inactivating fucosylation in a cell.

24 Claims, 18 Drawing Sheets

Specification includes a Sequence Listing.

MRAWTGSWRWIMLILFAWGTLLFYIGGHLVRDNDHPOHSSRELSKILAKLERLKQQNEDLRRMAESLRIPEGPIDQGTATGRVR

VLEEQLVKAKEQIENYKKQARNDLGKDHEILRRKIENGAKELWFFLQSELKKLKKLEGNELQRHADEILLDLGHHERSIMTDLY

YLSQTDGAGEWREKEAKDLTELVQRRITYLQNPKDCSKARKLVCNINKGCGYGCLHHVVYCFMIAYGTQRTLILESQNWRYAT

GGWETVFRPVSETCTDRSGLSTGHWSGEVKDKNVQVVELPIVDSLHPRPPYLPLAVPEDLADRLLRVHGDPAVWWVSQFVKYLI

RPQPWLEREIEETTKKLGFKHPVIGVHVRRTDKVGTEAAFHPIEEYMVHVEEHFQLLERRMKVDKKRVYLATDDPSLLKEAKTK

YSNYEFISDNSISWSAGLHNRYTENSLRGVILDIHFLSQADFLVCTFSSQVCRVAYEIMQTLHPDASANFHSLDDIYYFGGQNA

HNQIAVYPHQPRTKEEIPMEPGDIIGVAGNHWNGYSKGVNRKLSKTGLYPSYKVREKIETVKYPTYPEAEK

FIG. 2

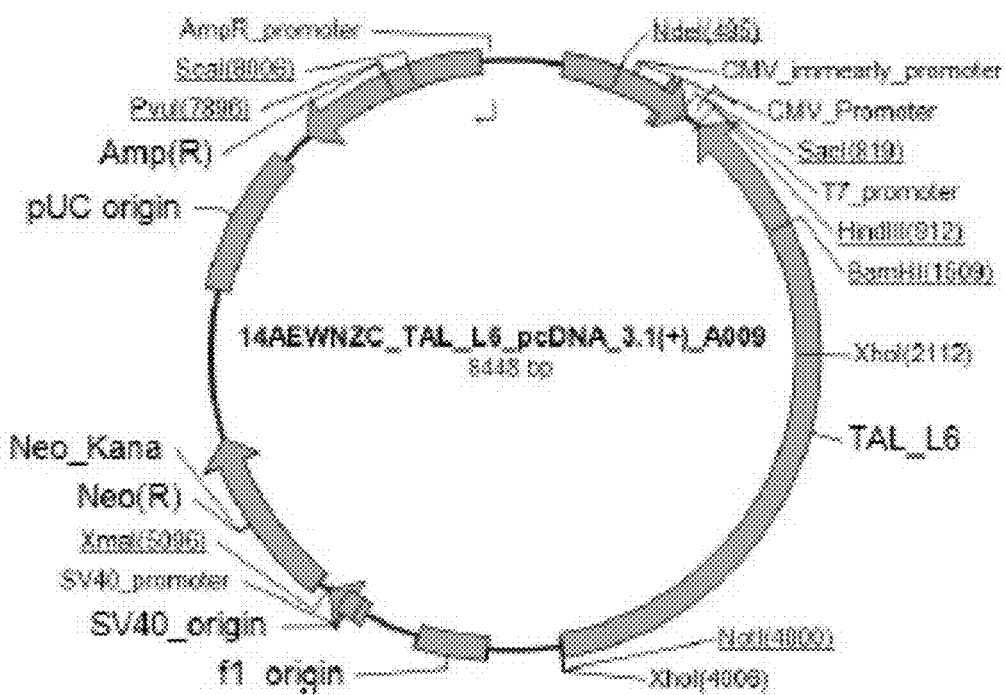

FIG. 3

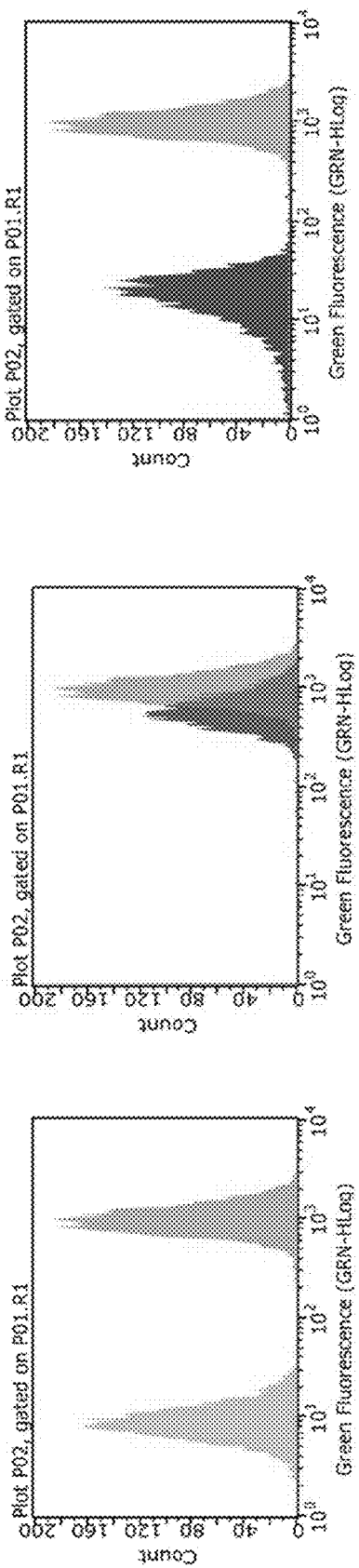
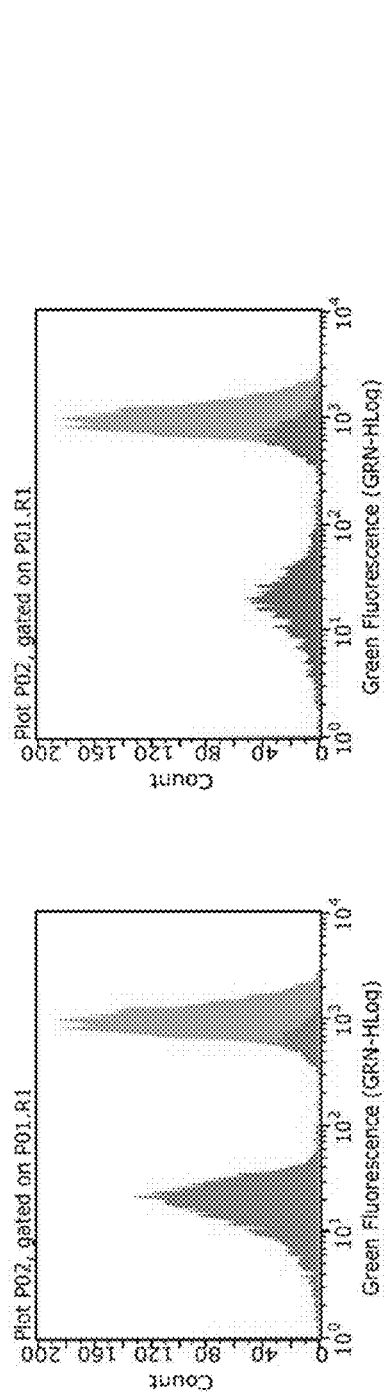
FIG. 8

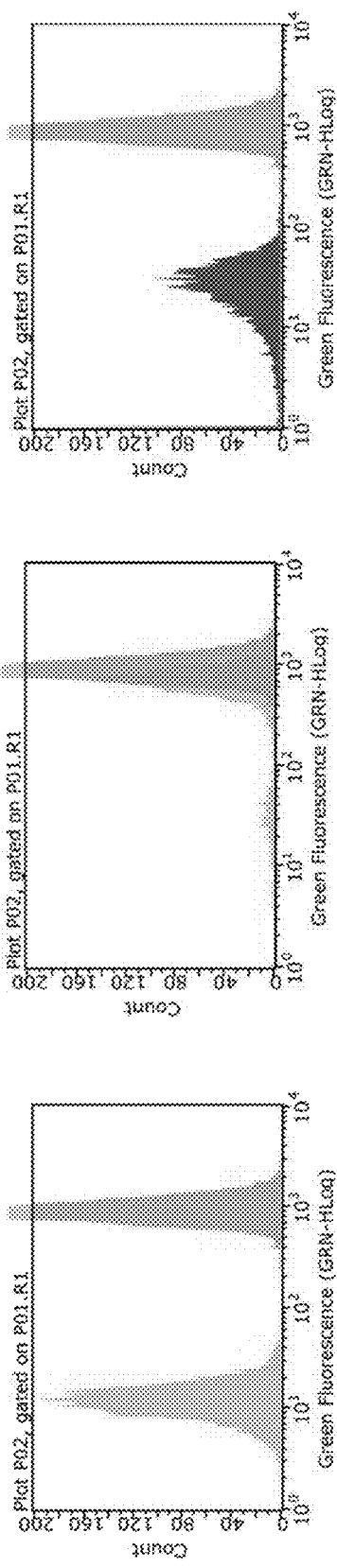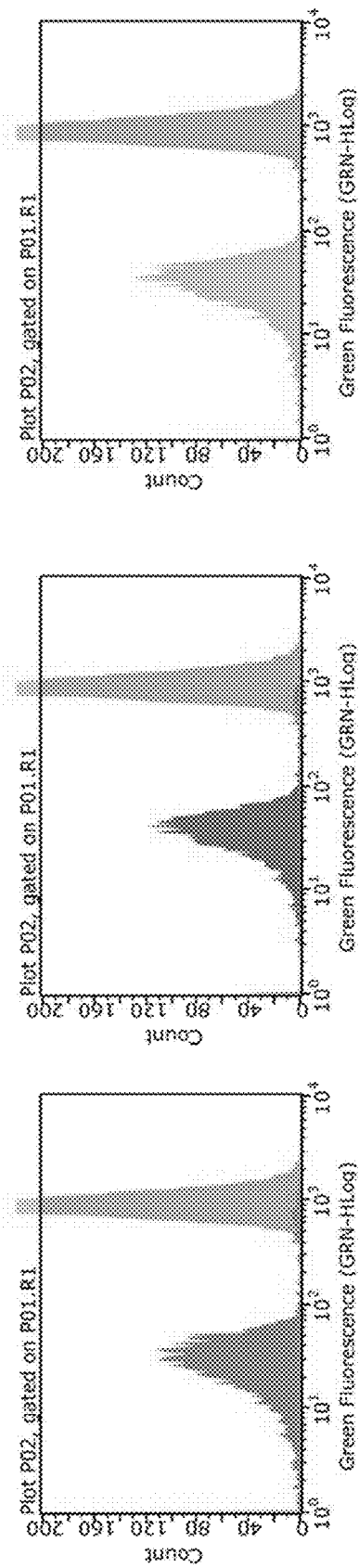
FIG. 11

Results:
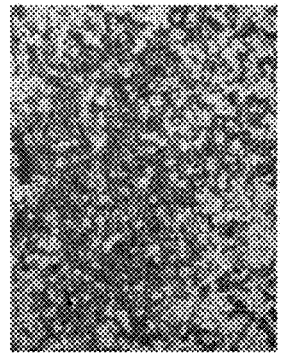
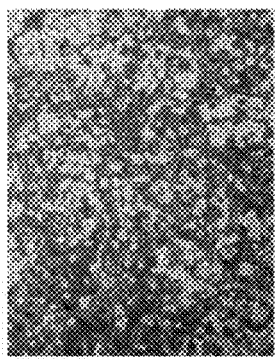
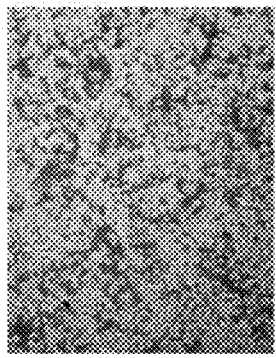
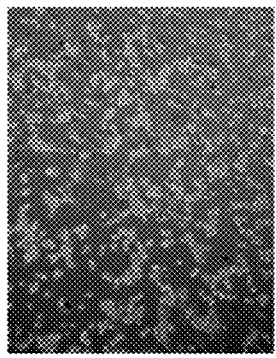
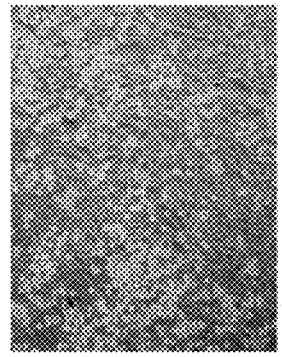
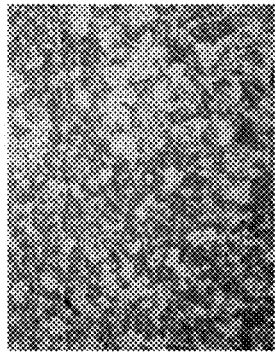
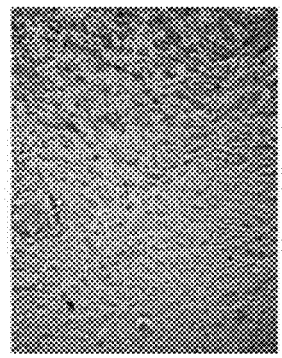
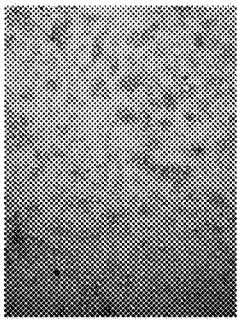
FIG. 16

FIG. 22B

FIG. 23 ical Field, genetic engineering and immunology. Particularly, the present disclosure relates to developing cell lines where specific biological pathways are modified. Such modifications are in the enzymes of the cell, particularly in enzymes involved in glycosylation of proteins. The present disclosure

SEQUENCE LISTING

```
<160> NUMBER OF SEQ ID NOS: 42

<210> SEQ ID NO 1
<211> LENGTH: 177
<212> TYPE: DNA
<213> ORGANISM: Cricetulus griseus
<220> FEATURE:
<221> NAME/KEY: gene
<222> LOCATION: (1)..(177)
<223> OTHER INFORMATION: Exon 9 DNA sequence

<400> SEQUENCE: 1
agtccatgtc agacgcactg acaaagtggg aacagaagca gccttccatc ccattgagga      60
atacatggta cacgttgaag aacattttca gcttctcgaa cgcagaatga aagtggataa     120
aaaaagagtg tatctggcca ctgatgaccc ttctttgtta aaggaggcaa agacaaa       177

<210> SEQ ID NO 2
<211> LENGTH: 58
<212> TYPE: PRT
<213> ORGANISM: Cricetulus griseus
<220> FEATURE:
<221> NAME/KEY: MISC_FEATURE
<222> LOCATION: (1)..(58)
<223> OTHER INFORMATION: Exon 9 amino acid sequence
```

<400> SEQUENCE: 2

```
Val His Val Arg Arg Thr Asp Lys Val Gly Thr Glu Ala Ala Phe His
1               5                   10                  15

Pro Ile Glu Glu Tyr Met Val His Val Glu Glu His Phe Gln Leu Leu
            20                  25                  30

Glu Arg Arg Met Lys Val Asp Lys Lys Arg Val Tyr Leu Ala Thr Asp
        35                  40                  45

Asp Pro Ser Leu Leu Lys Glu Ala Lys Thr
        50                  55
```

<210> SEQ ID NO 3
<211> LENGTH: 2177
<212> TYPE: DNA
<213> ORGANISM: Cricetulus griseus
<220> FEATURE:
<221> NAME/KEY: misc_feature
<222> LOCATION: (1)..(2177)

<400> SEQUENCE: 3

| | | |
|---|---|---|
| cgaaagtaca tagtgaaacc agaatattaa atagtgttca tctcctcaga cttcattgaa | 60 |
| attcagtgtg gcacattctc cctgcctcac ttcatttgta tagaacacac ggaacaagtc | 120 |
| caatttcctg agagaaacag tgattaagag gaatgtagga agaaaagat gactgcatag | 180 |
| ttattcctgt ggtcaaatcc acaactggac tatagtctgg gatgcaaagg aaacagtagc | 240 |
| atgaaggtgg cacagttacc ccagtgtgct acagccctga ctccagattc aagacataac | 300 |
| cctgtctttg gcaacactaa gatgcaggag agtgctggga agtcagtgac ttggccattg | 360 |
| caggtcagtg taagtctgta ttccttgctt tataacattg tgactttct tcaaaatgag | 420 |
| aaaatgaggt ctgtttctgt ttgcagttga tagagaaaaa aaatgcaaaa aaagtctgta | 480 |
| gtaacttcat gaacataaaa taaccaacat ctttaaaagg ctagcttgtc ttaaactaca | 540 |
| ggaaaagttc atatggatct ttgttttctt agatgacttt aaattctatg aactgaagtg | 600 |
| gtagtaactt tacagggtaa aatgaaagaa aaaaattaat aaactttggc ataagaatgt | 660 |
| tacaagcatt atcttttaagc tttgaattct gttatgattt tggtctcaaa accaaaaaaa | 720 |
| cttaaatctg ttgattccag gttcccatat attcttggat atgccaatta cttttctgt | 780 |
| aagcaagtgt ttcataaaac ttttacttaa ctttcatatt gacctgtact attcaacatt | 840 |
| cagctatgtt aaagtatttg tgaagtgttt tgaaatgatt ttatatttc taaggtgaga | 900 |
| ataaatgaga aaatgtttta atatgtctcc agtgcccca tgactaggga tactaattga | 960 |
| gtaccagtac attatcagtg tgctctccac ttctccccag agtccatgtc agacgcactg | 1020 |
| acaaagtggg aacagaagca gccttccatc ccattgagga atacatggta cacgttgaag | 1080 |
| aacattttca gcttctcgaa cgcagaatga aagtggataa aaaaagagtg tatctggcca | 1140 |
| ctgatgaccc ttctttgtta aaggaggcaa agacaaagta agttagacca caagtggtt | 1200 |
| ctgtatggga ttatctctta gttgaagaaa atccttaatt ctgggaactt gtggttcttg | 1260 |
| ttgctaacta ataggttcca aaatcaaaga ctacatgtgc aaatattaat ctaatcaagt | 1320 |
| cataccttac tagctgtatc tgatgcaaat taagaagtct aaaatgaatt agactgctga | 1380 |
| tttgtgtagc atcactagca gtcatcattc aacacagtac cacacttctt agtaccaaaa | 1440 |
| tctgtttaac atactagagt ttccataaat caaattttgt agcctggggc ttaagtaaca | 1500 |
| gaagtttatg tctcacagtt ttgatctggg atattccaga tcgaggtcct agtgatattg | 1560 |
| attttttactc tgaagtttct tagcttacag gtagtcacta tccagtcatg atacactgtg | 1620 |

```
ttgttaagga atttccattc tggggatgga acagaccatt agtatatggt acacctagta    1680
ctactgtggc attaggggaa gcacatagac agactttgat gattcccccc atgggaggcc    1740
tcaccctccc tgaggactgg atgggggagt gagatgggag ggttggtgag gggaatggga    1800
aagtgggagg gagagggaac tgggattggt atgtaaataa tatcatttta atttaaataa    1860
aaattaattt aaaaagaaag aagaagcac atagacaaag ccgtgagcaa aattggaaat     1920
tctcagaaga tctgggcgaa taaaattaaa agataaaatta tttatgaaat agaggaagga   1980
agaaaaattt agtcttagct cattatacta cctcctccaa aaatcatccc taagctttga    2040
gtaagtatcc ctcctctaca tattattggt gtatcattga atacttgtgc acttctgtct    2100
ccttcagtac attttatata cttttgatga gagtcctagc tgtggtatag gcctagtaaa    2160
tattgaatta tttactt                                                    2177

<210> SEQ ID NO 4
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL L6 binding site

<400> SEQUENCE: 4
tccacttctc cccagagtc                                                   19

<210> SEQ ID NO 5
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL R6 binding site

<400> SEQUENCE: 5
tgcttctgtt cccactttg                                                   19

<210> SEQ ID NO 6
<211> LENGTH: 36
<212> TYPE: PRT
<213> ORGANISM: Artificial Sequence
<220> FEATURE:
<223> OTHER INFORMATION: TAL-L6 amino acid sequence
<220> FEATURE:
<221> NAME/KEY: misc_feature
<222> LOCATION: (1)..(36)

<400> SEQUENCE: 6

His Asp His Asp Asn Ile His Asp Asn Gly Asn Gly His Asp Asn Gly
1               5                   10                  15

His Asp His Asp His Asp His Asp Asn Ile Asn Asn Ile Asn Asn
            20                  25                  30

Asn Gly His Asp
        35

<210> SEQ ID NO 7
<211> LENGTH: 1865
<212> TYPE: DNA
<213> ORGANISM: Artificial Sequence
<220> FEATURE:
<223> OTHER INFORMATION: TAL-L6 nucleotide sequence
<220> FEATURE:
```

<221> NAME/KEY: misc_feature
<222> LOCATION: (1)..(1865)

<400> SEQUENCE: 7

```
ggtggaagcc gtgcacgcct ggagaaatgc cctgacagga gccctctga acctgacccc    60
cgaacaggtg gtggccattg ccagccacga cggcggcaag caggccctgg aaaccgtgca   120
gagactgctg cccgtgctgt gccaggccca tggcctgaca cctgaacagg tggtggctat   180
cgcctctcac gacggaggaa acaggctct ggaaacagtg cagcggctgc tgcctgtgct   240
gtgtcaggct cacggcttga ctccagaaca ggtggtggct attgcttcca atattggggg   300
gaaacaggcc ctggaaactg tgcagcgcct gctgccagtc tgtgccagg ctcacggact   360
gaccccgaa caggtggtgg ccattgccag ccacgacggc ggcaagcagg ccctggaaac   420
cgtgcagaga ctgctgcccg tgctgtgcca ggcccatggc ctgacacctg aacaggtggt   480
ggctatcgcc tctaacggcg aggaaaaaca ggctctggaa acagtgcagc ggctgctgcc   540
tgtgctgtgt caggctcacg gcttgactcc agaacaggtg gtggctattg cttccaacgg   600
cgggggaaa caggccctgg aaactgtgca gcgcctgctg ccagtgctgt gccaggctca   660
cgggctgacc cccgaacagg tggtggccat tgccagccac gacggcggca agcaggccct   720
ggaaaccgtg cagagactgc tgcccgtgct gtgccaggcc catggcctga cacctgaaca   780
ggtggtggct atcgcctcta acggcggagg aaaacaggct ctggaaacag tgcagcggct   840
gctgcctgtg ctgtgtcagg ctcacggctt gactccagaa caggtggtgg ctattgcttc   900
ccacgacggg gggaaacagg ccctggaaac tgtgcagcgc ctgctgccag tgctgtgcca   960
ggctcacggc tcactcccg aacaggtggt ggccattgcc agccacgacg gcggcaagca  1020
ggccctggaa accgtgcaga gactgctgcc cgtgctgtgc aggcccatg gcctgacacc  1080
tgaacaggtg gtggctatcg cctctcacga cggaggaaaa caggctctgg aaacagtgca  1140
gcggctgctg cctgtgctgt gtcaggctca cggcttgact ccagaacagg tggtggctat  1200
tgcttcccac gacgggggga acaggccct ggaaactgtg cagcgcctgc tgccagtgct  1260
gtgccaggct cacggactga ccccgaaca ggtggtggcc attgccagca acatcggcgg  1320
caagcaggcc ctggaaaccg tgcagagact gctgcccgtg ctgtgccagg cccatggcct  1380
gacacctgaa caggtggtgg ctatcgcctc taacaacgga ggaaaacaag cactcgagac  1440
agtgcagcgg ctgctgcctg tgctgtgtca ggctcacggc ttgactccag aacaggtggt  1500
ggctattgct tccaatattg gggggaaaca ggccctggaa actgtgcagc gcctgctgcc  1560
agtgctgtgc caggctcacg gctgacccc gaacaggtg gtggccattg ccagcaacaa  1620
cggcggcaag caggccctgg aaaccgtgca gagactgctg cccgtgctgt gccaggccca  1680
tggcctgaca cctgaacagg tggtggctat cgcctctaac ggcggaggaa acaggctct  1740
ggaaacagtg cagcggctgc tgcctgtgct gtgtcaggct cacggcttga ctccacagca  1800
ggtcgtggca attgctagcc acgacggcgg acgcccgcc ctggagagca ttgtggccca  1860
gctgt                                                             1865
```

<210> SEQ ID NO 8
<211> LENGTH: 36
<212> TYPE: PRT
<213> ORGANISM: Artificial Sequence
<220> FEATURE:
<223> OTHER INFORMATION: TAL-R6 amino acid sequence
<220> FEATURE:
<221> NAME/KEY: MISC_FEATURE
<222> LOCATION: (1)..(36)

<400> SEQUENCE: 8

Asn Asn His Asp Asn Gly Asn Gly His Asp Asn Gly Asn Asn Gly
1               5                   10                  15

Asn Gly His Asp His Asp His Asp Asn Ile His Asp Asn Gly Asn Gly
            20                  25                  30

Asn Gly Asn Asn
        35

<210> SEQ ID NO 9
<211> LENGTH: 1865
<212> TYPE: DNA
<213> ORGANISM: Artificial Sequence
<220> FEATURE:
<223> OTHER INFORMATION: TAL-R6 nucleotide sequence
<220> FEATURE:
<221> NAME/KEY: misc_feature
<222> LOCATION: (1)..(1865)

<400> SEQUENCE: 9

```
ggtggaagcc gtgcacgcct ggagaaatgc cctgacagga gccctctga acctgacccc      60
cgaacaggtg gtggccattg ccagcaacaa cggcggcaag caggccctgg aaaccgtgca    120
gagactgctg cccgtgctgt gccaggccca tggcctgaca cctgaacagg tggtggctat    180
cgcctctcac gacggaggaa acaggtctct ggaaacagtg cagcggctgc tgcctgtgct    240
gtgtcaggct cacggcttga ctccagaaca ggtggtggct attgcttcca acggcggggg    300
gaaacaggcc ctgaaactg tgcagcgcct gctgccagtg ctgtgccagg ctcacggact    360
gaccccgaa caggtggtgg ccattgccag caacggcggg gcaagcagg ccctggaaac    420
cgtgcagaga ctgctgcccg tgctgtgcca ggcccatggc ctgacacctg aacaggtggt    480
ggctatcgcc tctcacgacg gagaaaaca ggctctggaa acagtgcagc ggctgctgcc    540
tgtgctgtgt caggctcacg gcttgactcc agaacaggtg gtggctattg cttccaacgg    600
cgggggaaa caggccctgg aaactgtgca gcgcctgctg ccagtgctgt gccaggctca    660
cgggctgacc cccgaacagg tggtggccat tgccagcaac aacggcggca agcaggccct    720
ggaaaccgtg cagagactgc tgcccgtgct gtgcaggcc atggcctga cacctgaaca    780
ggtggtggct atcgcctcta cggcggagg aaaacaggct ctggaaacag tgcagcggct    840
gctgcctgtg ctgtgtcagg ctcacggctt gactccagaa caggtggtgg ctattgcttc    900
caacggcggg gggaaacagg ccctggaaac tgtgcagcgc ctgctgccag tgctgtgcca    960
ggctcacggc ctcactcccg aacaggtggt ggccattgcc agccacgacg gcggcaagca   1020
ggccctggaa accgtgcaga gactgctgcc cgtgctgtgc aggcccatg gcctgacacc   1080
tgaacaggtg gtggctatcg cctctcacga cggaggaaaa caggctctgg aaacagtgca   1140
gcggctgctg cctgtgctgt gtcaggctca cggcttgact ccagaacagg tggtggctat   1200
tgcttcccac gacgggggga acaggccct ggaaactgtg cagcgcctgc tgccagtgct   1260
gtgccaggct cacggactga cccccgaaca ggtggtggcc attgccagca acatcggcgg   1320
caagcaggcc ctggaaaccg tgcagagact gctgcccgtg ctgtgccagg cccatggcct   1380
gacacctgaa caggtggtgg ctatcgcctc tcacgacggg gaaaacaag cactcgagac   1440
agtgcagcgg ctgctgcctg tgctgtgtca ggctcacggc ttgactccag aacaggtggt   1500
ggctattgct tccaacggcg gggggaaaca ggccctggaa actgtgcagc gcctgctgcc   1560
agtgctgtgc caggctcacg gcctgacccc cgaacaggtg gtggccattg ccagcaacgg   1620
```

-continued

```
cggcggcaag caggccctgg aaaccgtgca gagactgctg cccgtgctgt gccaggccca      1680
tggcctgaca cctgaacagg tggtggctat cgcctctaac ggcggaggaa acaggctct       1740 ggaaacagtg cagcggctgc tgcctgtgct gtgtcaggct cacggcttga ctccacagca     1800
ggtcgtggca attgctagca acaacggcgg acggcccgcc ctggagagca ttgtggccca     1860
gctgt                                                                 1865
```

<210> SEQ ID NO 10
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL L1- Binding site

<400> SEQUENCE: 10

```
tgtgctctcc acttctccc                                                    19
```

<210> SEQ ID NO 11
<211> LENGTH: 36
<212> TYPE: PRT
<213> ORGANISM: Artificial Sequence
<220> FEATURE:
<223> OTHER INFORMATION: TAL-L1 amino acid sequence
<220> FEATURE:
<221> NAME/KEY: MISC_FEATURE
<222> LOCATION: (1)..(36)

<400> SEQUENCE: 11

```
Asn Asn Asn Gly Asn Asn His Asp Asn Gly His Asp Asn Gly His Asp
1               5                   10                  15

His Asp Asn Ile His Asp Asn Gly Asn Gly His Asp Asn Gly His Asp
            20                  25                  30

His Asp His Asp
        35
```

<210> SEQ ID NO 12
<211> LENGTH: 1865
<212> TYPE: DNA
<213> ORGANISM: Artificial Sequence
<220> FEATURE:
<223> OTHER INFORMATION: TAL-L1 nucleotide sequence
<220> FEATURE:
<221> NAME/KEY: misc_feature
<222> LOCATION: (1)..(1865)

<400> SEQUENCE: 12

```
ggtggaagcc gtgcacgcct ggagaaatgc cctgacagga gcccctctga acctgacccc       60
cgaacaggtg gtggccattg ccagcaacaa cggcggcaag caggccctgg aaaccgtgca      120
gagactgctg cccgtgctgt gccaggccca tggcctgaca cctgaacagg tggtggctat     180
cgcctctaac ggcggaggaa acaggctct ggaaacagtg cagcggctgc tgcctgtgct      240
gtgtcaggct cacggcttga ctccagaaca ggtggtggct attgcttcca acaacggggg     300
gaaacaggcc ctggaaactg tgcagcgcct gctgccagtg ctgtgccagg ctcacggact     360
gacccccgaa caggtggtgg ccattgccag ccacgacggc ggcaagcagg ccctggaaac     420
cgtgcagaga ctgctgcccg tgctgtgcca gggccatggc ctgacacctg aacaggtggt     480
ggctatcgcc tctaacggcg gaggaaaaca ggctctggaa acagtgcagc ggctgctgcc     540
tgtgctgtgt caggctcacg gcttgactcc agaacaggtg gtggctattg cttcccacga     600
```

```
cgggggggaaa caggccctgg aaactgtgca gcgcctgctg ccagtgctgt gccaggctca    660
cgggctgacc cccgaacagg tggtggccat tgccagcaac ggcggcggca agcaggccct    720
ggaaaccgtg cagagactgc tgcccgtgct gtgccaggcc catggcctga cacctgaaca    780
ggtggtggct atcgcctctc acgacggagg aaaacaggct ctggaaacag tgcagcggct    840
gctgcctgtg ctgtgtcagg ctcacggctt gactccagaa caggtggtgg ctattgcttc    900
ccacgacggg gggaaacagg ccctggaaac tgtgcagcgc tgctgccag tgctgtgcca    960 ggctcacggc ctcactcccg aacaggtggt ggccattgcc agcaatattg cggcaagca   1020 ggccctggaa accgtgcaga gactgctgcc cgtgctgtgc caggcccatg gcctgacacc   1080
tgaacaggtg gtggctatcg cctctcacga cggaggaaaa caggctctgg aaacagtgca   1140
gcggctgctg cctgtgctgt gtcaggctca cggcttgact ccagaacagg tggtggctat   1200
tgcttccaac ggcggggga acaggccct ggaaactgtg cagcgcctgc tgccagtgct   1260
gtgccaggct cacggactga cccccgaaca ggtggtggcc attgccagca acggcggcgg   1320
caagcaggcc ctggaaaccg tgcagagact gctgcccgtg ctgtgccagg cccatggcct   1380
gacacctgaa caggtggtgg ctatcgcctc tcacgacgga ggaaaacaag cactcgagac   1440
agtgcagcgg ctgctgcctg tgctgtgtca ggctcacggc ttgactccag aacaggtggt   1500
ggctattgct tccaacggcg gggaaaca ggccctggaa actgtgcagc gcctgctgcc   1560
agtgctgtgc caggctcacg gctgacccc cgaacaggtg gtggcattg ccagccacga   1620 cggcggcaag caggccctgg aaaccgtgca gagactgctg cccgtgctgt gccaggccca   1680
tggcctgaca cctgaacagg tggtggctat cgcctctcac gacggaggaa acaggctct   1740 ggaaacagtg cagcggctgc tgcctgtgct gtgtcaggct cacggcttga ctccacagca   1800
ggtcgtggca attgctagcc acgacggcgg acggcccgcc ctggagagca ttgtggccca   1860
gctgt                                                                1865

<210> SEQ ID NO 13
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL R1 - Binding site

<400> SEQUENCE: 13
tcccactttg tcagtgcgt                                                    19

<210> SEQ ID NO 14
<211> LENGTH: 36
<212> TYPE: PRT
<213> ORGANISM: Artificial Sequence
<220> FEATURE:
<223> OTHER INFORMATION: TAL-R1 amino acid sequence
<220> FEATURE:
<221> NAME/KEY: MISC_FEATURE
<222> LOCATION: (1)..(36)

<400> SEQUENCE: 14

His Asp His Asp His Asp Asn Ile His Asp Asn Gly Asn Gly Asn Gly
1               5                   10                  15

Asn Asn Asn Gly His Asp Asn Ile Asn Asn Gly Asn Asn His Asp
            20                  25                  30

Asn Asn Asn Gly
        35
```

```
<210> SEQ ID NO 15
<211> LENGTH: 1865
<212> TYPE: DNA
<213> ORGANISM: Artificial Sequence
<220> FEATURE:
<223> OTHER INFORMATION: TAL-R1 nucleotide sequence
<220> FEATURE:
<221> NAME/KEY: misc_feature
<222> LOCATION: (1)..(1865)

<400> SEQUENCE: 15
```

| | | | | | |
|---|---|---|---|---|---|
| ggtggaagcc | gtgcacgcct | ggagaaatgc | cctgacagga | gcccctctga | acctgacccc      60 |
| cgaacaggtg | gtggccattg | ccagccacga | cggcggcaag | caggccctgg | aaaccgtgca     120 |
| gagactgctg | cccgtgctgt | gccaggccca | tggcctgaca | cctgaacagg | tggtggctat     180 |
| cgcctctcac | gacggaggaa | acaggctct | ggaaacagtg | cagcggctgc | tgcctgtgct     240 |
| gtgtcaggct | cacggcttga | ctccagaaca | ggtggtggct | attgcttccc | acgacggggg     300 |
| gaaacaggcc | ctggaaactg | tgcagcgcct | gctgccagtc | tgtgccaggc | tcacggact     360 |
| gaccccgaa | caggtggtgg | ccattgccag | caatattggc | ggcaagcagg | ccctggaaac     420 |
| cgtgcagaga | ctgctgcccg | tgctgtgcca | ggcccatggc | ctgacacctg | aacaggtggt     480 |
| ggctatcgcc | tctcacgacg | gaggaaaaca | ggctctggaa | acagtgcagc | ggctgctgcc     540 |
| tgtgctgtgt | caggctcacg | gcttgactcc | agaacaggtg | gtggctattg | cttccaacgg     600 |
| cgggggaaa | cagcccctgg | aaactgtgca | gcgcctgctg | ccagtgctgt | gccaggctca     660 |
| cgggctgacc | cccgaacagg | tggtggccat | tgccagcaac | ggcggcgca | agcaggccct     720 |
| ggaaaccgtg | cagagactgc | tgcccgtgct | gtgccaggcc | catggcctga | cacctgaaca     780 |
| ggtggtggct | atcgcctcta | acggcggagg | aaaacaggct | ctggaaacag | tgcagcggct     840 |
| gctgcctgtg | ctgtgtcagg | ctcacggctt | gactccagaa | caggtggtgg | ctattgcttc     900 |
| caacaacggg | gggaaacagg | ccctggaaac | tgtgcagcgc | ctgctgccag | tgctgtgcca     960 |
| ggctcacggc | ctcactcccg | aacaggtggt | ggccattgcc | agcaacggcg | gcggcaagca    1020 |
| ggccctggaa | accgtgcaga | gactgctgcc | cgtgctgtgc | caggcccatg | gcctgacacc    1080 |
| tgaacaggtg | gtggctatcg | cctctcacga | cggaggaaaa | caggctctgg | aaacagtgca    1140 |
| gcggctgctg | cctgtgctgt | gtcaggctca | cggcttgact | ccagaacagg | tggtggctat    1200 |
| tgcttccaat | attgggggga | aacaggccct | ggaaactgtg | cagcgcctgc | tgccagtgct    1260 |
| gtgccaggct | cacggactga | ccccgaaca | ggtggtggcc | attgccagca | acaacggcgg    1320 |
| caagcaggcc | ctggaaaccg | tgcagagact | gctgcccgtg | ctgtgccagg | cccatggcct    1380 |
| gacacctgaa | caggtggtgg | ctatcgcctc | taacggcgga | ggaaaacaag | cactcgagac    1440 |
| agtgcagcgg | ctgctgcctg | tgctgtgtca | ggctcacggc | ttgactccag | aacaggtggt    1500 |
| ggctattgct | tccaacaacg | gggggaaaca | ggccctggaa | actgtgcagc | gcctgctgcc    1560 |
| agtgctgtgc | caggctcacg | gcctgacccc | cgaacaggtg | gtggccattg | ccagccacga    1620 |
| cggcggcaag | caggccctgg | aaaccgtgca | gagactgctg | cccgtgctgt | gccaggccca    1680 |
| tggcctgaca | cctgaacagg | tggtggctat | cgcctctaac | aacggaggaa | acaggctct    1740 |
| ggaaacagtg | cagcggctgc | tgcctgtgct | gtgtcaggct | cacggcttga | ctccacagca    1800 |
| ggtcgtggca | attgctagca | acggcggcgg | acggcccgcc | ctggagagca | ttgtggccca    1860 |
| gctgt | | | | |            1865 |

```
<210> SEQ ID NO 16
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL L2 binding site

<400> SEQUENCE: 16
tcagcttctc gaacgcaga                                                  19

<210> SEQ ID NO 17
<211> LENGTH: 36
<212> TYPE: PRT
<213> ORGANISM: Artificial Sequence
<220> FEATURE:
<223> OTHER INFORMATION: TAL L2 amino acid sequence
<220> FEATURE:
<221> NAME/KEY: MISC_FEATURE
<222> LOCATION: (1)..(36)

<400> SEQUENCE: 17

His Asp Asn Ile Asn Asn His Asp Asn Gly Asn Gly His Asp Asn Gly
1               5                   10                  15

His Asp Asn Asn Asn Ile Asn Ile His Asp Asn Asn His Asp Asn Ile
            20                  25                  30

Asn Asn Asn Ile
        35

<210> SEQ ID NO 18
<211> LENGTH: 1865
<212> TYPE: DNA
<213> ORGANISM: Artificial Sequence
<220> FEATURE:
<223> OTHER INFORMATION: TAL L2 nucleotide sequence
<220> FEATURE:
<221> NAME/KEY: misc_feature
<222> LOCATION: (1)..(1865)

<400> SEQUENCE: 18
ggtggaagcc gtgcacgcct ggagaaatgc cctgacagga gccctctga  acctgacccc     60 cgaacaggtg gtggccattg ccagccacga cggcggcaag caggccctgg aaaccgtgca    120
gagactgctg cccgtgctgt gccaggccca tggcctgaca cctgaacagg tggtggctat    180
cgcctctaat attggaggaa acaggctct  ggaaacagtg cagcggctgc tgcctgtgct    240
gtgtcaggct cacggcttga ctccagaaca ggtggtggct attgcttcca acaacggggg    300
gaaacaggcc ctggaaactg tgcagcgcct gctgccagtg ctgtgccagg ctcacggact    360
gacccccgaa caggtggtgg ccattgccag ccacgacggc ggcaagcagg ccctggaaac    420
cgtgcagaga ctgctgcccg tgctgtgcca ggcccatggc ctgacacctg aacaggtggt    480
ggctatcgcc tctaacggcg gagaaaaaca ggctctggaa acagtgcagc ggctgctgcc    540
tgtgctgtgt caggctcacg gcttgactcc agaacaggtg gtggctattg cttccaacgg    600 cgggggggaaa caggccctgg aaactgtgca gcgcctgctg ccagtgctgt gccaggctca    660
cgggctgacc cccgaacagg tggtggccat tgccagccac gacggcggca agcaggccct    720
ggaaaccgtg cagagactgc tgcccgtgct gtgccaggcc catggcctga cacctgaaca    780
ggtggtggct atcgcctcta acggcggagg aaaacaggct ctggaaacag tgcagcggct    840
gctgcctgtg ctgtgtcagg ctcacggctt gactccagaa caggtggtgg ctattgcttc    900
ccacgacggg gggaaacagg ccctggaaac tgtgcagcgc ctgctgccag tgctgtgcca    960
```

```
ggctcacggc ctcactcccg aacaggtggt ggccattgcc agcaacaacg gcggcaagca    1020
ggccctggaa accgtgcaga gactgctgcc cgtgctgtgc caggcccatg gcctgacacc    1080
tgaacaggtg gtggctatcg cctctaatat tggaggaaaa caggctctgg aaacagtgca    1140
gcggctgctg cctgtgctgt gtcaggctca cggcttgact ccagaacagg tggtggctat    1200
tgcttccaat attgggggga aacaggccct ggaaactgtg cagcgcctgc tgccagtgct    1260
gtgccaggct cacggactga cccccgaaca ggtggtggcc attgccagcc acgacggcgg    1320
caagcaggcc ctggaaaccg tgcagagact gctgcccgtg ctgtgccagg cccatggcct    1380
gacacctgaa caggtggtgg ctatcgcctc taacaacgga ggaaaacaag cactcgagac    1440
agtgcagcgg ctgctgcctg tgctgtgtca ggctcacggc ttgactccag aacaggtggt    1500
ggctattgct tcccacgacg gggggaaaca ggccctggaa actgtgcagc gcctgctgcc    1560
agtgctgtgc caggctcacg gctgaccccc gaacaggtg gtggccattg ccagcaatat    1620
tggcggcaag caggccctgg aaaccgtgca gagactgctg cccgtgctgt gccaggccca    1680
tggcctgaca cctgaacagg tggtggctat cgcctctaac aacgaggaa acaggctct    1740 ggaaacagtg cagcggctgc tgcctgtgct gtgtcaggct cacggcttga ctccacagca    1800
ggtcgtggca attgctagca atattggcgg acggcccgcc ctggagagca ttgtggccca    1860
gctgt                                                                1865

<210> SEQ ID NO 19
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL R2 binding site

<400> SEQUENCE: 19
tggccagata cactcttt                                                  19

<210> SEQ ID NO 20
<211> LENGTH: 36
<212> TYPE: PRT
<213> ORGANISM: Artificial Sequence
<220> FEATURE:
<223> OTHER INFORMATION: TAL R2 amino acid sequence
<220> FEATURE:
<221> NAME/KEY: MISC_FEATURE
<222> LOCATION: (1)..(36)

<400> SEQUENCE: 20

Asn Asn Asn Asn His Asp His Asp Asn Ile Asn Asn Asn Ile Asn Gly
1               5                   10                  15

Asn Ile His Asp Asn Ile His Asp Asn Gly His Asp Asn Gly Asn Gly
            20                  25                  30

Asn Gly Asn Gly
        35

<210> SEQ ID NO 21
<211> LENGTH: 1865
<212> TYPE: DNA
<213> ORGANISM: Artificial Sequence
<220> FEATURE:
<223> OTHER INFORMATION: TAL R2 nucleotide sequence
<220> FEATURE:
<221> NAME/KEY: misc_feature
<222> LOCATION: (1)..(1865)
```

<400> SEQUENCE: 21

```
ggtggaagcc gtgcacgcct ggagaaatgc cctgacagga gccctctga  acctgacccc     60
cgaacaggtg gtggccattg ccagcaacaa cggcggcaag caggccctgg aaaccgtgca    120
gagactgctg cccgtgctgt gccaggccca tggcctgaca cctgaacagg tggtggctat    180
cgcctctaac aacggaggaa aacaggctct ggaaacagtg cagcggctgc tgcctgtgct    240
gtgtcaggct cacggcttga ctccagaaca ggtggtggct attgcttccc acgacggggg    300
gaaacaggcc ctggaaactg tgcagcgcct gctgccagtg ctgtgccagg ctcacggact    360
gacccccgaa caggtggtgg ccattgccag ccacgacggc ggcaagcagg ccctggaaac    420
cgtgcagaga ctgctgcccg tgctgtgcca ggcccatggc ctgacacctg aacaggtggt    480
ggctatcgcc tctaatattg gaggaaaaca ggctctggaa acagtgcagc ggctgctgcc    540
tgtgctgtgt caggctcacg gcttgactcc agaacaggtg gtggctattg cttccaacaa    600
cggggggaaa caggccctgg aaactgtgca gcgcctgctg ccagtgctgt gccaggctca    660
cgggctgacc cccgaacagg tggtggccat tgccagcaat attggcggca agcaggccct    720
ggaaaccgtg cagagactgc tgcccgtgct gtgccaggcc atggcctga  cacctgaaca    780
ggtggtggct atcgcctcta acggcggagg aaaacaggct ctggaaacag tgcagcggct    840
gctgcctgtg ctgtgtcagg ctcacggctt gactccagaa caggtggtgg ctattgcttc    900
caatattggg gggaaacagg ccctggaaac tgtgcagcgc ctgctgccag tgctgtgcca    960
ggctcacggc tcactcccg aacaggtggt ggccattgcc agccacgacg gcggcaagca   1020
ggccctggaa accgtgcaga gactgctgcc cgtgctgtgc caggcccatg gcctgacacc   1080
tgaacaggtg gtggctatcg cctctaatat tggaggaaaa caggtctggg aaacagtgca   1140
gcggctgctg cctgtgctgt gtcaggctca cggcttgact ccagaacagg tggtggctat   1200
tgcttcccac gacggggga aacaggccct ggaaactgtg cagcgcctgc tgccagtgct   1260
gtgccaggct cacggactga ccccgaaca ggtggtggcc attgccagca acggcggcgg   1320
caagcaggcc ctggaaaccg tgcagagact gctgcccgtg ctgtgccagg cccatggcct   1380
gacacctgaa caggtggtgg ctatcgcctc tcacgacgga ggaaaacaag cactcgagac   1440
agtgcagcgg ctgctgcctg tgctgtgtca ggctcacggc ttgactccag aacaggtggt   1500
ggctattgct tccaacggcg ggggaaaca ggccctggaa actgtgcagc gcctgctgcc   1560
agtgctgtgc caggctcacg gctgacccc cgaacaggtg gtggccattg ccagcaacgg   1620
cggcggcaag caggccctgg aaaccgtgca gagactgctg cccgtgctgt gccaggccca   1680
tggcctgaca cctgaacagg tggtggctat cgcctctaac ggcggaggaa aacaggctct   1740
ggaaacagtg cagcggctgc tgcctgtgct gtgtcaggct cacggcttga ctccacagca   1800
ggtcgtggca attgctagca acggcggcgg acggcccgcc ctggagagca ttgtggccca   1860
gctgt                                                                1865
```

<210> SEQ ID NO 22
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL L3 binding site

<400> SEQUENCE: 22

-continued tgacaaagtg ggaacagaa            19

<210> SEQ ID NO 23
<211> LENGTH: 36
<212> TYPE: PRT
<213> ORGANISM: Artificial Sequence
<220> FEATURE:
<223> OTHER INFORMATION: TAL L3 amino acid sequence
<220> FEATURE:
<221> NAME/KEY: MISC_FEATURE
<222> LOCATION: (1)..(36)

<400> SEQUENCE: 23

Asn Asn Asn Ile His Asp Asn Ile Asn Ile Asn Asn Asn Gly
1               5                   10                  15

Asn Asn Asn Asn Asn Asn Asn Ile Asn Ile His Asp Asn Ile Asn Asn
                20                  25                  30

Asn Ile Asn Ile
        35

<210> SEQ ID NO 24
<211> LENGTH: 1865
<212> TYPE: DNA
<213> ORGANISM: Artificial Sequence
<220> FEATURE:
<223> OTHER INFORMATION: TAL L3 nucleotide sequence
<220> FEATURE:
<221> NAME/KEY: misc_feature
<222> LOCATION: (1)..(1865)

<400> SEQUENCE: 24
ggtggaagcc gtgcacgcct ggagaaatgc cctgacagga gccctctga acctgacccc      60 cgaacaggtg gtggccattg ccagcaacaa cggcggcaag caggccctgg aaaccgtgca    120
gagactgctg cccgtgctgt gccaggccca tggcctgaca cctgaacagg tggtggctat    180
cgcctctaat attggaggaa aacaggtctg gaaacagtg cagcggctgc tgcctgtgct    240
gtgtcaggct cacggcttga ctccagaaca ggtggtggct attgcttccc acgacggggg    300
gaaacaggcc ctggaaactg tgcagcgcct gctgccagtg ctgtgccagg ctcacggact    360
gacccccgaa caggtggtgg ccattgccag caatattggc ggcaagcagg ccctggaaac    420
cgtgcagaga ctgctgcccg tgctgtgcca ggcccatggc ctgacacctg aacaggtggt    480
ggctatcgcc tctaatattg gaggaaaaca ggctctggaa acagtgcagc ggctgctgcc    540
tgtgctgtgt caggctcacg gcttgactcc agaacaggtg gtggctattg cttccaatat    600
tggggggaaa caggccctgg aaactgtgca gcgcctgctg ccagtgctgt gccaggctca    660
cgggctgacc cccgaacagg tggtggccat tgccagcaac aacggcggca agcaggccct    720
ggaaaccgtg cagagactgc tgcccgtgct gtgccaggcc catggcctga cacctgaaca    780
ggtggtggct atcgcctcta acggcggagg aaaacaggct ctggaaacag tgcagcggct    840
gctgcctgtg ctgtgtcagg ctcacggctt gactccagaa caggtggtgg ctattgcttc    900
caacaacggg gggaaacagg ccctggaaac tgtgcagcgc ctgctgccag tgctgtgcca    960
ggctcacggc tcactcccg aacaggtggt ggccattgcc agcaacaacg gcggcaagca   1020
ggccctggaa accgtgcaga gactgctgcc cgtgctgtgc caggcccatg gcctgacacc   1080
tgaacaggtg gtggctatcg cctctaacaa cggaggaaaa caggctctgg aaacagtgca   1140
gcggctgctg cctgtgctgt gtcaggctca cggcttgact ccagaacagg tggtggctat   1200
tgcttccaat attgggggga acaggccct ggaaactgtg cagcgcctgc tgccagtgct   1260

```
gtgccaggct cacggactga cccccgaaca ggtggtggcc attgccagca atattggcgg    1320
caagcaggcc ctggaaaccg tgcagagact gctgcccgtg ctgtgccagg cccatggcct    1380
gacacctgaa caggtggtgg ctatcgcctc tcacgacgga ggaaaacaag cactcgagac    1440
agtgcagcgg ctgctgcctg tgctgtgtca ggctcacggc ttgactccag aacaggtggt    1500
ggctattgct tccaatattg gggggaaaca ggccctggaa actgtgcagc gcctgctgcc    1560
agtgctgtgc caggctcacg ggctgacccc gaacaggtg gtggccattg ccagcaacaa    1620
cggcggcaag caggccctgg aaaccgtgca gagactgctg cccgtgctgt gccaggccca    1680
tggcctgaca cctgaacagg tggtggctat cgcctctaat attggaggaa acaggctct    1740 ggaaacagtg cagcggctgc tgcctgtgct gtgtcaggct cacggcttga ctccacagca    1800
ggtcgtggca attgctagca atattggcgg acggcccgcc ctggagagca ttgtggccca    1860
gctgt                                                                1865

<210> SEQ ID NO 25
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL R3 binding site

<400> SEQUENCE: 25
tgtaccatgt attcctcaa                                                    19

<210> SEQ ID NO 26
<211> LENGTH: 36
<212> TYPE: PRT
<213> ORGANISM: Artificial Sequence
<220> FEATURE:
<223> OTHER INFORMATION: TAL R3 amino acid sequence
<220> FEATURE:
<221> NAME/KEY: MISC_FEATURE
<222> LOCATION: (1)..(36)

<400> SEQUENCE: 26

Asn Asn Asn Gly Asn Ile His Asp His Asp Asn Ile Asn Gly Asn Asn
1               5                   10                  15

Asn Gly Asn Ile Asn Gly Asn Gly His Asp His Asp Asn Gly His Asp
            20                  25                  30

Asn Ile Asn Ile
        35

<210> SEQ ID NO 27
<211> LENGTH: 1865
<212> TYPE: DNA
<213> ORGANISM: Artificial Sequence
<220> FEATURE:
<223> OTHER INFORMATION: TAL R3 nucleotide sequence
<220> FEATURE:
<221> NAME/KEY: misc_feature
<222> LOCATION: (1)..(1865)

<400> SEQUENCE: 27
ggtggaagcc gtgcacgcct ggagaaatgc cctgacagga gccctctga acctgacccc      60 cgaacaggtg gtggccattg ccagcaacaa cggcggcaag caggccctgg aaaccgtgca    120
gagactgctg cccgtgctgt gccaggccca tggcctgaca cctgaacagg tggtggctat    180
cgcctctaac ggcggaggaa acaggctct ggaaacagtg cagcggctgc tgcctgtgct    240
```

-continued

```
gtgtcaggct cacggcttga ctccagaaca ggtggtggct attgcttcca atattggggg    300
gaaacaggcc ctggaaactg tgcagcgcct gctgccagtg ctgtgccagg ctcacggact    360
gacccccgaa caggtggtgg ccattgccag ccacgacggc ggcaagcagg ccctggaaac    420
cgtgcagaga ctgctgcccg tgctgtgcca ggcccatggc ctgacacctg aacaggtggt    480
ggctatcgcc tctcacgacg gaggaaaaca ggctctggaa acagtgcagc ggctgctgcc    540
tgtgctgtgt caggctcacg gcttgactcc agaacaggtg gtggctattg cttccaatat    600
tggggggaaa caggccctgg aaactgtgca gcgcctgctg ccagtgctgt gccaggctca    660
cgggctgacc cccgaacagg tggtggccat tgccagcaac ggcggcggca agcaggccct    720
ggaaaccgtg cagagactgc tgcccgtgct gtgccaggcc catggcctga cacctgaaca    780
ggtggtggct atcgcctcta acaacggagg aaaacaggct ctggaaacag tgcagcggct    840
gctgcctgtg ctgtgtcagg ctcacggctt gactccagaa caggtggtgg ctattgcttc    900
caacggcggg gggaaacagg ccctggaaac tgtgcagcgc ctgctgccag tgctgtgcca    960
ggctcacggc ctcactcccg aacaggtggt ggccattgcc agcaatattg gcggcaagca   1020
ggccctggaa accgtgcaga gactgctgcc cgtgctgtgc caggcccatg gcctgacacc   1080
tgaacaggtg gtggctatcg cctctaacgg cggaggaaaa caggctctgg aaacagtgca   1140
gcggctgctg cctgtgctgt gtcaggctca cggcttgact ccagaacagg tggtggctat   1200
tgcttccaac ggcgggggga acaggccct ggaaactgtg cagcgcctgc tgccagtgct   1260
gtgccaggct cacggactga ccccgaaca ggtggtggcc attgccagcc acgacggcgg   1320
caagcaggcc ctggaaaccg tgcagagact gctgcccgtg ctgtgccagg cccatggcct   1380
gacacctgaa caggtggtgg ctatcgcctc tcacgacgga ggaaaacaag cactcgagac   1440
agtgcagcgc tgctgcctg tgctgtgtca ggctcacggc ttgactccag aacaggtggt   1500
ggctattgct tccaacggcg ggggaaaca ggccctggaa actgtgcagc gcctgctgcc   1560
agtgctgtgc caggctcacg gctgacccc gaacaggtg gtggccattg ccagccacga   1620
cggcggcaag caggccctgg aaaccgtgca gagactgctg cccgtgctgt gccaggccca   1680
tggcctgaca cctgaacagg tggtggctat cgcctctaat attggaggaa aacaggctct   1740
ggaaacagtg cagcggctgc tgcctgtgct gtgtcaggct cacggcttga ctccacagca   1800
ggtcgtggca attgctagca atattggcgg acggcccgcc ctggagagca ttgtggccca   1860
gctgt                                                                1865
```

<210> SEQ ID NO 28
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL L4 binding site

<400> SEQUENCE: 28
tgtcagacgc actgacaaa                                                    19

<210> SEQ ID NO 29
<211> LENGTH: 36
<212> TYPE: PRT
<213> ORGANISM: Artificial Sequence
<220> FEATURE:
<223> OTHER INFORMATION: TAL L4 amino acid sequence
<220> FEATURE:
<221> NAME/KEY: MISC_FEATURE

<222> LOCATION: (1)..(36)

<400> SEQUENCE: 29

Asn Asn Asn Gly His Asp Asn Ile Asn Asn Asn Ile His Asp Asn
1               5                   10                  15

His Asp Asn Ile His Asp Asn Gly Asn Asn Ile His Asp Asn Ile
            20                  25                  30

Asn Ile Asn Ile
        35

<210> SEQ ID NO 30
<211> LENGTH: 1865
<212> TYPE: DNA
<213> ORGANISM: Artificial Sequence
<220> FEATURE:
<223> OTHER INFORMATION: TAL L4 nucleotide sequence
<220> FEATURE:
<221> NAME/KEY: misc_feature
<222> LOCATION: (1)..(1865)

<400> SEQUENCE: 30

| | | | | |
|---|---|---|---|---|
| ggtggaagcc | gtgcacgcct | ggagaaatgc | cctgacagga | gcccctctga acctgacccc | 60 |
| cgaacaggtg | gtggccattg | ccagcaacaa | cggcggcaag | caggccctgg aaaccgtgca | 120 |
| gagactgctg | cccgtgctgt | gccaggccca | tggcctgaca | cctgaacagg tggtggctat | 180 |
| cgcctctaac | ggcggaggaa | aacaggtctg | gaaacagtg | cagcggctgc tgcctgtgct | 240 |
| gtgtcaggct | cacggcttga | ctccagaaca | ggtggtggct | attgcttccc acgacggggg | 300 |
| gaaacaggcc | ctggaaactg | tgcagcgcct | gctgccagtc | tgtgccaggc tcacggact | 360 |
| gaccccgaa | caggtggtgg | ccattgccag | caatattggc | ggcaagcagg ccctggaaac | 420 |
| cgtgcagaga | ctgctgcccg | tgctgtgcca | ggcccatggc | ctgacacctg aacaggtggt | 480 |
| ggctatcgcc | tctaacaacg | gagaaaaca | ggctctggaa | acagtgcagc ggctgctgcc | 540 |
| tgtgctgtgt | caggctcacg | gcttgactcc | agaacaggtg | gtggctattg cttccaatat | 600 |
| tgggggaaa | caggccctgg | aaactgtgca | gcgcctgctg | ccagtgctgt gccaggctca | 660 |
| cgggctgacc | cccgaacagg | tggtggccat | tgccagccac | gacggcggca agcaggccct | 720 |
| ggaaaccgtg | cagagactgc | tgcccgtgct | gtgccaggcc | atggcctga cacctgaaca | 780 |
| ggtggtggct | atcgcctcta | caacggagg | aaaacaggct | ctggaaacag tgcagcggct | 840 |
| gctgcctgtg | ctgtgtcagg | ctcacggctt | gactccagaa | caggtggtgg ctattgcttc | 900 |
| ccacgacggg | gggaaacagg | ccctggaaac | tgtgcagcgc | ctgctgccag tgctgtgcca | 960 |
| ggctcacggc | ctcactcccg | aacaggtggt | ggccattgcc | agcaatattg gcggcaagca | 1020 |
| ggccctggaa | accgtgcaga | gactgctgcc | cgtgctgtgc | caggcccatg gcctgacacc | 1080 |
| tgaacaggtg | gtggctatcg | cctctcacga | cggaggaaaa | caggctctgg aaacagtgca | 1140 |
| gcggctgctg | cctgtgctgt | gtcaggctca | cggcttgact | ccagaacagg tggtggctat | 1200 |
| tgcttccaac | ggcgggggga | aacaggccct | ggaaactgtg | cagcgcctgc tgccagtgct | 1260 |
| gtgccaggct | cacggactga | ccccgaaca | ggtggtggcc | attgccagca acaacggcgg | 1320 |
| caagcaggcc | ctggaaaccg | tgcagagact | gctgcccgtg | ctgtgccagg cccatggcct | 1380 |
| gacacctgaa | caggtggtgg | ctatcgcctc | taatattgga | ggaaaacaag cactcgagac | 1440 |
| agtgcagcgg | ctgctgcctg | tgctgtcaa | ggctcacggc | ttgactccag aacaggtggt | 1500 |
| ggctattgct | tccacgacg | gggggaaaca | ggccctggaa | actgtgcagc gcctgctgcc | 1560 |
| agtgctgtgc | caggctcacg | gctgacccc | cgaacaggtg | gtggccattg ccagcaatat | 1620 |

| | | | | |
|---|---|---|---|---|
| tggcggcaag | caggccctgg | aaaccgtgca | gagactgctg | cccgtgctgt gccaggccca | 1680 |
| tggcctgaca | cctgaacagg | tggtggctat | cgcctctaat | attggaggaa aacaggctct | 1740 |
| ggaaacagtg | cagcggctgc | tgcctgtgct | gtgtcaggct | cacggcttga ctccacagca | 1800 |
| ggtcgtggca | attgctagca | atattggcgg | acggcccgcc | ctggagagca ttgtggccca | 1860 |
| gctgt | | | | | 1865 |

<210> SEQ ID NO 31
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL R4 binding site

<400> SEQUENCE: 31
tcctcaatgg gatggaagg                                                 19

<210> SEQ ID NO 32
<211> LENGTH: 36
<212> TYPE: PRT
<213> ORGANISM: Artificial Sequence
<220> FEATURE:
<223> OTHER INFORMATION: TAL R4 amino acid sequence
<220> FEATURE:
<221> NAME/KEY: MISC_FEATURE
<222> LOCATION: (1)..(36)

<400> SEQUENCE: 32

His Asp His Asp Asn Gly His Asp Asn Ile Asn Ile Asn Gly Asn Asn
1               5                   10                  15

Asn Asn Asn Asn Asn Ile Asn Gly Asn Asn Asn Asn Ile Asn Ile
            20                  25                  30

Asn Asn Asn Gly
        35

<210> SEQ ID NO 33
<211> LENGTH: 1865
<212> TYPE: DNA
<213> ORGANISM: Artificial Sequence
<220> FEATURE:
<223> OTHER INFORMATION: TAL R4 Nucleotide sequence
<220> FEATURE:
<221> NAME/KEY: misc_feature
<222> LOCATION: (1)..(1865)

<400> SEQUENCE: 33

| | | | | |
|---|---|---|---|---|
| ggtggaagcc | gtgcacgcct | ggagaaatgc | cctgacagga | gcccctctga acctgacccc | 60 |
| cgaacaggtg | gtggccattg | ccagccacga | cggcggcaag | caggccctgg aaaccgtgca | 120 |
| gagactgctg | cccgtgctgt | gccaggccca | tggcctgaca | cctgaacagg tggtggctat | 180 |
| cgcctctcac | gacggaggaa | acaggctct | ggaaacagtg | cagcggctgc tgcctgtgct | 240 |
| gtgtcaggct | cacggcttga | ctccagaaca | ggtggtggct | attgcttcca acggcggggg | 300 |
| gaaacaggcc | ctggaaactg | tgcagcgcct | gctgccagtg | ctgtgccagg ctcacggact | 360 |
| gaccccgaa | caggtggtgg | ccattgccag | ccacgacggc | ggcaagcagg ccctggaaac | 420 |
| cgtgcagaga | ctgctgcccg | tgctgtgcca | ggcccatggc | ctgacacctg aacaggtggt | 480 |
| ggctatcgcc | tctaatattg | gaggaaaaca | ggctctggaa | acagtgcagc ggctgctgcc | 540 |
| tgtgctgtgt | caggctcacg | gcttgactcc | agaacaggtg | gtggctattg cttccaatat | 600 |

-continued

```
tgggggaaa caggccctgg aaactgtgca gcgcctgctg ccagtgctgt gccaggctca      660
cgggctgacc cccgaacagg tggtggccat tgccagcaac ggcggcggca agcaggccct      720
ggaaaccgtg cagagactgc tgcccgtgct gtgccaggcc catggcctga cacctgaaca      780
ggtggtggct atcgcctcta acaacggagg aaaacaggct ctggaaacag tgcagcggct      840
gctgcctgtg ctgtgtcagg ctcacggctt gactccagaa caggtggtgg ctattgcttc      900
caacaacggg gggaaacagg ccctggaaac tgtgcagcgc ctgctgccag tgctgtgcca      960
ggctcacggc ctcactcccg aacaggtggt ggccattgcc agcaacaacg gcggcaagca     1020
ggccctggaa accgtgcaga gactgctgcc cgtgctgtgc caggcccatg gcctgacacc     1080
tgaacaggtg gtggctatcg cctctaatat ggaggaaaaa caggctctgg aaacagtgca     1140
gcggctgctg cctgtgctgt gtcaggctca cggcttgact ccagaacagg tggtggctat     1200
tgcttccaac ggcgggggga acaggcccct ggaaactgtg cagcgcctgc tgccagtgct     1260
gtgccaggct cacggactga cccccgaaca ggtggtggcc attgccagca acaacggcgg     1320
caagcaggcc ctggaaaccg tgcagagact gctgcccgtg ctgtgccagg ccatggcct     1380 gacacctgaa caggtggtgg ctatcgcctc taacaacgga ggaaaacaag cactcgagac     1440
agtgcagcgg ctgctgcctg tgctgtgtca ggctcacggc ttgactccag aacaggtggt     1500
ggctattgct tccaatattg gggggaaaca ggccctggaa actgtgcagc gcctgctgcc     1560
agtgctgtgc caggctcacg gctgaccccc gaacaggtg gtggccattg ccagcaatat     1620
tggcggcaag caggccctgg aaaccgtgca gagactgctg cccgtgctgt gccaggccca     1680
tggcctgaca cctgaacagg tggtggctat cgcctctaac aacggaggaa acaggctct     1740 ggaaacagtg cagcggctgc tgcctgtgct gtgtcaggct cacggcttga ctccacagca     1800
ggtcgtggca attgctagca acaacggcgg acggcccgcc ctggagagca ttgtggccca     1860
gctgt                                                                  1865
```

<210> SEQ ID NO 34
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL L5 binding site

<400> SEQUENCE: 34

```
tccccagagt ccatgtcag                                                   19
```

<210> SEQ ID NO 35
<211> LENGTH: 36
<212> TYPE: PRT
<213> ORGANISM: Artificial Sequence
<220> FEATURE:
<223> OTHER INFORMATION: TAL L5 amino acid sequence
<220> FEATURE:
<221> NAME/KEY: MISC_FEATURE
<222> LOCATION: (1)..(36)

<400> SEQUENCE: 35

```
His Asp His Asp His Asp His Asp Asn Ile Asn Asn Asn Ile Asn Asn
1               5                   10                  15

Asn Gly His Asp His Asp Asn Ile Asn Gly Asn Asn Asn Gly His Asp
            20                  25                  30

Asn Ile Asn Asn
```

<210> SEQ ID NO 36
<211> LENGTH: 1865
<212> TYPE: DNA
<213> ORGANISM: Artificial Sequence
<220> FEATURE:
<223> OTHER INFORMATION: TAL L5 nucleotide sequence
<220> FEATURE:
<221> NAME/KEY: misc_feature
<222> LOCATION: (1)..(1865)

<400> SEQUENCE: 36

| | | | | | |
|---|---|---|---|---|---|
| ggtggaagcc | gtgcacgcct | ggagaaatgc | cctgacagga | gcccctctga | acctgacccc | 60 |
| cgaacaggtg | gtggccattg | ccagccacga | cggcggcaag | caggccctgg | aaaccgtgca | 120 |
| gagactgctg | cccgtgctgt | gccaggccca | tggcctgaca | cctgaacagg | tggtggctat | 180 |
| cgcctctcac | gacggaggaa | acaggctct | ggaaacagtg | cagcggctgc | tgcctgtgct | 240 |
| gtgtcaggct | cacggcttga | ctccagaaca | ggtggtggcc | attgcttccc | acgacggggg | 300 |
| gaaacaggcc | ctggaaactg | tgcagcgcct | gctgccagtg | ctgtgccagg | ctcacggact | 360 |
| gacccccgaa | caggtggtgg | ccattgccag | ccacgacggc | ggcaagcagg | ccctggaaac | 420 |
| cgtgcagaga | ctgctgcccg | tgctgtgcca | ggcccatggc | ctgacacctg | aacaggtggt | 480 |
| ggctatcgcc | tctaatattg | gaggaaaaca | ggctctggaa | acagtgcagc | ggctgctgcc | 540 |
| tgtgctgtgt | caggctcacg | gcttgactcc | agaacaggtg | gtggctattg | cttccaacaa | 600 |
| cggggggaaa | caggccctgg | aaactgtgca | gcgcctgctg | ccagtgctgt | gccaggctca | 660 |
| cgggctgacc | cccgaacagg | tggtggccat | tgccagcaat | attggcggca | gcaggccct | 720 |
| ggaaaccgtg | cagagactgc | tgcccgtgct | gtgccaggcc | catggcctga | cacctgaaca | 780 |
| ggtggtggct | atcgcctcta | caacggagg | aaaacaggct | ctggaaacag | tgcagcggct | 840 |
| gctgcctgtg | ctgtgtcagg | ctcacggctt | gactccagaa | caggtggtgg | ctattgcttc | 900 |
| caacggcggg | gggaaacagg | ccctggaaac | tgtgcagcgc | ctgctgccag | tgctgtgcca | 960 |
| ggctcacggc | ctcactcccg | aacaggtggt | ggccattgcc | agccacgacg | gcggcaagca | 1020 |
| ggccctggaa | accgtgcaga | gactgctgcc | cgtgctgtgc | caggcccatg | gcctgacacc | 1080 |
| tgaacaggtg | gtggctatcg | cctctcacga | cggaggaaaa | caggctctgg | aaacagtgca | 1140 |
| gcggctgctg | cctgtgctgt | gtcaggctca | cggcttgact | ccagaacagg | tggtggctat | 1200 |
| tgcttccaat | attgggggga | acaggcccct | ggaaactgtg | cagcgcctgc | tgccagtgct | 1260 |
| gtgccaggct | cacggactga | cccccgaaca | ggtggtggcc | attgccagca | acggcggcgg | 1320 |
| caagcaggcc | ctggaaaccg | tgcagagact | gctgcccgtg | ctgtgccagg | cccatggcct | 1380 |
| gacacctgaa | caggtggtgg | ctatcgcctc | taacaacgga | ggaaaacaag | cactcgagac | 1440 |
| agtgcagcgg | ctgctgcctg | tgctgtgtca | ggctcacggc | ttgactccag | aacaggtggt | 1500 |
| ggctattgct | tccaacggcg | ggggaaaca | ggccctggaa | actgtgcagc | gcctgctgcc | 1560 |
| agtgctgtgc | caggctcacg | gctgacccc | cgaacaggtg | gtggccattg | ccagccacga | 1620 |
| cggcggcaag | caggccctgg | aaaccgtgca | gagactgctg | cccgtgctgt | gccaggccca | 1680 |
| tggcctgaca | cctgaacagg | tggtggctat | cgcctctaat | attggaggaa | acaggctct | 1740 |
| ggaaacagtg | cagcggctgc | tgcctgtgct | gtgtcaggct | cacggcttga | ctccacagca | 1800 |
| ggtcgtggca | attgctagca | acaacggcgg | acggcccgcc | ctggagagca | ttgtggccca | 1860 |
| gctgt | | | | | | 1865 |

<210> SEQ ID NO 37
<211> LENGTH: 19
<212> TYPE: DNA
<213> ORGANISM: Cricetulus griseus
<220> FEATURE:
<221> NAME/KEY: misc_binding
<222> LOCATION: (1)..(19)
<223> OTHER INFORMATION: TAL R5 binding site

<400> SEQUENCE: 37
tggaaggctg cttctgttc                                                    19

<210> SEQ ID NO 38
<211> LENGTH: 36
<212> TYPE: PRT
<213> ORGANISM: Artificial Sequence
<220> FEATURE:
<223> OTHER INFORMATION: TAL R5 amino acid sequence
<220> FEATURE:
<221> NAME/KEY: MISC_FEATURE
<222> LOCATION: (1)..(36)

<400> SEQUENCE: 38

Asn Asn Asn Asn Asn Ile Asn Ile Asn Asn Asn Asn His Asp Asn Gly
1               5                   10                  15

Asn Asn His Asp Asn Gly Asn Gly His Asp Asn Gly Asn Asn Asn Gly
            20                  25                  30

Asn Gly His Asp
        35

<210> SEQ ID NO 39
<211> LENGTH: 1865
<212> TYPE: DNA
<213> ORGANISM: Artificial Sequence
<220> FEATURE:
<223> OTHER INFORMATION: TAL R5 nucleotide sequence
<220> FEATURE:
<221> NAME/KEY: misc_feature
<222> LOCATION: (1)..(1865)

<400> SEQUENCE: 39
ggtggaagcc gtgcacgcct ggagaaatgc cctgacagga gccctctga acctgacccc        60 cgaacaggtg gtggccattg ccagcaacaa cggcggcaag caggccctgg aaaccgtgca      120
gagactgctg cccgtgctgt gccaggccca tggcctgaca cctgaacagg tggtggctat      180
cgcctctaac aacggaggaa aacaggctct ggaaacagtg cagcggctgc tgcctgtgct      240
gtgtcaggct cacggcttga ctccagaaca ggtggtggct attgcttcca atattggggg      300
gaaacaggcc ctggaaactg tgcagcgcct gctgccagtg ctgtgccagg ctcacggact      360
gacccccgaa caggtggtgg ccattgccag caatattggc ggcaagcagg ccctggaaac      420
cgtgcagaga ctgctgcccg tgctgtgcca ggcccatggc ctgacacctg aacaggtggt      480
ggctatcgcc tctaacaacg gaggaaaaca ggctctggaa acagtgcagc ggctgctgcc      540
tgtgctgtgt caggctcacg gcttgactcc agaacaggtg gtggctattg cttccaacaa      600
cggggggaaa caggccctgg aaactgtgca gcgcctgctg ccagtgctgt gccaggctca      660
cgggctgacc cccgaacagg tggtggccat tgccagccac gacggcggca agcaggccct      720
ggaaaccgtg cagagactgc tgcccgtgct gtgccaggcc catggcctga cacctgaaca      780
ggtggtggct atcgcctcta acggcggagg aaaacaggct ctggaaacag tgcagcggct      840
gctgcctgtg ctgtgtcagg ctcacggctt gactccagaa caggtggtgg ctattgcttc      900

| | |
|---|---|
| caacaacggg gggaaacagg ccctggaaac tgtgcagcgc ctgctgccag tgctgtgcca | 960 |
| ggctcacggc ctcactcccg aacaggtggt ggccattgcc agccacgacg cggcaagca | 1020 |
| ggccctggaa accgtgcaga gactgctgcc cgtgctgtgc caggcccatg gcctgacacc | 1080 |
| tgaacaggtg gtggctatcg cctctaacgg cggaggaaaa caggctctgg aaacagtgca | 1140 |
| gcggctgctg cctgtgctgt gtcaggctca cggcttgact ccagaacagg tggtggctat | 1200 |
| tgcttccaac ggcggggggga acaggccct ggaaactgtg cagcgcctgc tgccagtgct | 1260 |
| gtgccaggct cacggactga cccccgaaca ggtggtggcc attgccagcc acgacggcgg | 1320 |
| caagcaggcc ctggaaaccg tgcagagact gctgcccgtg ctgtgccagg cccatggcct | 1380 |
| gacacctgaa caggtggtgg ctatcgcctc taacggcgga ggaaaacaag cactcgagac | 1440 |
| agtgcagcgg ctgctgcctg tgctgtgtca ggctcacggc ttgactccag aacaggtggt | 1500 |
| ggctattgct tccaacaacg ggggaaaca ggccctggaa actgtgcagc gcctgctgcc | 1560 |
| agtgctgtgc caggctcacg gctgacccc cgaacaggtg gtggccattg ccagcaacgg | 1620 |
| cggcggcaag caggccctgg aaaccgtgca gagactgctg cccgtgctgt gccaggccca | 1680 |
| tggcctgaca cctgaacagg tggtggctat cgcctctaac ggcggaggaa acaggctct | 1740 |
| ggaaacagtg cagcggctgc tgcctgtgct gtgtcaggct cacggcttga ctccacagca | 1800 |
| ggtcgtggca attgctagcc acgacggcgg acggcccgcc ctggagagca ttgtggccca | 1860 |
| gctgt | 1865 |

<210> SEQ ID NO 40
<211> LENGTH: 3126
<212> TYPE: DNA
<213> ORGANISM: Cricetulus griseus
<220> FEATURE:
<221> NAME/KEY: mRNA
<222> LOCATION: (1)..(3126)
<223> OTHER INFORMATION: Cricetulus griseus Fut8 mRNA

<400> SEQUENCE: 40

| | |
|---|---|
| caggtcttgg ctctggctta ggccatctat gaccctggtg gtgttttcat tcactataag | 60 |
| tccttcccat cttattaac tgagcaagtt cagctagtaa ttttagagac cgaggttcaa | 120 |
| gcaataacac ctatctctgc aataccgtgt ggctttcttc aatgtcttac atcctaagga | 180 |
| aaggaagcat gtagagccca ggaagcacag gacaagaaag ctgcctcctt gtatcaccag | 240 |
| gaagatcttt ttgtaagagt catcacagta taccagagag actaattttg tctgaagcat | 300 |
| catgtgttga acaacagaa acttattttc ctgtgtggct aactgaacc agagtacaat | 360 |
| gtttccaatt ctttgagctc cgagaagaca gaagggagtt gaaactctga aaatgcgggc | 420 |
| atggactggt tcctggcgtt ggattatgct cattcttttt gcctggggga ccttattgtt | 480 |
| ttatataggt ggtcatttgg ttcgagataa tgaccaccct gaccattcta gcagagaact | 540 |
| ctccaagatt cttgcaaagc tggagcgctt aaaacaacaa atgaagact tgaggagaat | 600 |
| ggctgagtct ctccgaatac cagaaggccc tattgatcag gggacagcta caggaagagt | 660 |
| ccgtgttta aagaacagc ttgttaaggc caagaacag attgaaaatt acaagaaaca | 720 |
| agctaggaat gatctgggaa aggatcatga atcttaagg aggaggattg aaaatgagc | 780 |
| taaagagctc tggtttttc tacaaagtga attgaagaaa ttaaagaaat tagaaggaaa | 840 |
| cgaactccaa agacatgcag atgaaattct tttggattta ggacatcatg aaaggtctat | 900 |
| catgacagat ctatactacc tcagtcaaac agatggagca ggtgagtggc gggaaaaaga | 960 |
| agccaaagat ctgacagagc tggtccagcg gagaataaca tatctgcaga atcccaagga | 1020 |

```
ctgcagcaaa gccagaaagc tggtatgtaa tatcaacaaa ggctgtggct atggatgtca    1080
actccatcat gtggtttact gcttcatgat tgcttatggc acccagcgaa cactcatctt    1140
ggaatctcag aattggcgct atgctactgg aggatgggag actgtgttta gacctgtaag    1200
tgagacatgc acagacaggt ctggcctctc cactggcacg tggtcaggtg aagtgaagga    1260
caaaaatgtt caagtggtcg agctccccat tgtagacagc ctccatcctc gtcctcctta    1320
cttacccttg gctgtaccag aagacctcgc agatcgactc ctgagagtcc atggtgatcc    1380
tgcagtgtgg tgggtatccc agtttgtcaa atacttgatc cgtccacaac cttggctgga    1440
aagggaaata gaagaaacca ccaagaagct tggcttcaaa catccagtta ttggagtcca    1500
tgtcagacgc actgacaaag tgggaacaga agcagccttc catcccattg aggaatacat    1560
ggtacacgtt gaagaacatt ttcagcttct cgaacgcaga atgaaagtgg ataaaaaaag    1620
agtgtatctg gccactgatg acccttcttt gttaaaggag gcaaagacaa agtactccaa    1680
ttatgaattt attagtgata actctatttc ttggtcagct ggactacaca accgatacac    1740
agaaaattca cttcggggcg tgatcctgga tatacacttt ctctcccagg ctgacttcct    1800
tgtgtgtact ttttcatccc aggtctgtag ggttgcttat gaaatcatgc aaacactgca    1860
tcctgatgcc tctgcaaact tccattcttt agatgacatc tactattttg gaggccaaaa    1920
tgcccacaac cagattgcag tttatcctca ccaacctcga actaaagagg aaatccccat    1980
ggaacctgga gatatcattg gtgtggctgg aaaccattgg aatggttact ctaaaggtgt    2040
caacagaaaa ctaggaaaaa caggcctgta cccttcctac aaagtccgag agaagataga    2100
aacagtcaaa taccctacat atcctgaagc tgaaaaatag agatggagtg taagagatta    2160
acaacgaaat ttagttcaga ccatctcagc caagcagaag acccagacta acatatggtt    2220
cattgacaga catgctccgc accaagagca agtgggaacc ctcagatgct gcactggtgg    2280
aacgcctctt tgtgaagggc tgctgtgccc tcaagcccat gcacagtaaa ataatgtact    2340
cacacataac atacaaatgg attattttct actttgccct ttaaatattc tgtccccatg    2400
aaacaaacac tgccacatta tgtaatttaa gtgacacaga cgttttgtgt gagacttcaa    2460
acatggtgcc tatatctgag agacctctgt gatttactga gaagatgaga acagctccct    2520
tctgtgggga agttggttct tagtcagtgg tggactggcc actgaattca ctgcaatcaa    2580
cagattcaga atgagaatgg atgttttcc tttatatggt tgtctggatt ttttttaaag    2640
taatttcatc agttcagttc atccacctca ttaataaatg aaggaatata ccaataaaat    2700
caaatgaaat attcactgtc cattaggaag ttttataaaa caatgccatg aacaaaaaat    2760
tctttagtac tcaatgtttc tggacattct ctttgataac aaaaataaat tttaaaaagg    2820
aattttgtaa agtttctggg attctgtatc actggatgat gtagttataa gctttgtagt    2880
agaaatatgg gaagtgggtt tatagctttt aagattttt tctacttttg tcctacttt    2940 tctatttctg atagaataat catatttcaa gagaagcatt ggtcccctct aatactagta    3000
actgccttta gtcatgcata ttatatgaag ttgctaagaa cacgctttgg gggaggtgtt    3060
cactctctta gtttgatatt gttgacttga tataattgaa tgaaatagtc attctcttgc    3120
ttccag                                                              3126
```

<210> SEQ ID NO 41
<211> LENGTH: 24
<212> TYPE: DNA
<213> ORGANISM: Artificial Sequence
<220> FEATURE:

```
<223> OTHER INFORMATION: Forward Primer
<220> FEATURE:
<221> NAME/KEY: primer_bind
<222> LOCATION: (1)..(24)

<400> SEQUENCE: 41
gacctgtact attcaacatt cagc                                              24

<210> SEQ ID NO 42
<211> LENGTH: 23
<212> TYPE: DNA
<213> ORGANISM: Artificial Sequence
<220> FEATURE:
<223> OTHER INFORMATION: Reverse Primer
<220> FEATURE:
<221> NAME/KEY: primer_bind
<222> LOCATION: (1)..(23)

<400> SEQUENCE: 42
gagataatcc catacagaac cac                                               23
```

NON-FUCOSYLATED PROTEIN AND METHODS THEREOF

CROSS REFERENCE TO RELATED APPLICATIONS

This application is a U.S. National Stage entry of International Application No. PCT/IB2015/055777, filed Jul. 30, 2015, which claims priority to Indian Patent Application No. 3728/CHE/2014, filed Jul. 30, 2014.

STATEMENT REGARDING SEQUENCE LISTING

This application incorporates by reference a Sequence Listing submitted with this application as text file, Sequence Listing 102365-1037515-000200US, created on Jun. 26, 2017, and having a size of 49,681 bytes. The sequence listing has the same content as the sequence listing that was submitted with the as-filed international application PCT/IB2015/055777 and includes no new matter.

TECHNICAL FIELD

The present disclosure pertains to the field of biotechnology, genetic engineering and immunology. Particularly, the present disclosure relates to developing cell lines where specific biological pathways are modified. Such modifications are in the enzymes of the cell, particularly in enzymes involved in glycosylation of proteins. The present disclosure develops protein expression systems wherein specific modification of glycan chain of the protein is achieved. The specific modification of the glycan chain produces non-fucosylated proteins, including antibodies. Such products are used in developing therapeutics and biomarkers, and in diagnosis and prognosis of various diseases. The present disclosure employs the Transcription Activator like Effector Nuclease (TALEN) technology.

BACKGROUND AND PRIOR ART OF THE DISCLOSURE

Glycosylation in eukaryotes has been studied intensively for decades as the most common covalent post translational protein modification mechanism (Varki et al 2009). About 1-2% of the human transcriptome (about 250-500 glycogenes) is predicted to translate proteins which are responsible for glycosylation (Campbell and Yarema 2005). Glycosylation of cellular proteins plays many key biological functions such as protein folding, stability, intracellular and inter-cellular trafficking, cell-cell and cell matrix Interaction.

There are four distinct groups of Glycoproteins: N-linked, O-linked, glycosaminoglycans, and glycosylphosphatidylinositol-anchored proteins. N-linked glycosylation occurs through the side chain amide nitrogen of asparagine residues, while O-linked glycosylation uses the oxygen atom in the side chain of serine or threonine residues. N-linked glycosylation takes place in the amino acid sequence of Asn-X-Ser/Thr, where X can be any amino acid except proline and aspartic acid (Helenius and Aebi 2004).

Fucose (6-deoxy-L-galactose) is a monosaccharide that is present in many glycoproteins and glycolipids present in vertebrates, invertebrates, plants, and bacteria. Fucosylation is the process of transferring a fucose residue to various proteins and oligosaccharides. Fucosylation is regulated by several molecules, including fucosyltransferases, guanosine diphosphate (GDP)-fucose synthetic enzymes, and GDP-fucose transporter(s). A large number of fucosylated glycoproteins are secretary proteins or membrane proteins on the cell surface. A potent example of fucosylated glycoprotein is fucosylated alpha-fetoprotein (AFP), an important cancer biomarker (Simm, 1979).

There are 14.1 million new cancer cases, 8.2 million cancer deaths and 32.6 million people living with cancer (within 5 years of diagnosis) in 2014 worldwide. The high mortality rate of cancer serves as a reminder of the need for more effective therapies. The most prominent change in oncology drug development in the last 20 years has been the shift from classic cytotoxics to drugs that affect signaling pathways implicated in cancer, known as "Monoclonal Antibodies" or mAbs. A decade ago, there were only two mAbs on the market and currently there are around 30 FDA approved mAbs of diverse therapeutic modalities, like Adalimumab, Infliximab, Rituximab etc. mAbs are the fastest growing segment in pharmaceutical industry and this rapid expansion is set to continue. Now there are more than 100 monoclonal antibody-based biologic drugs in clinical trials. Many of these are in phase II and phase III trials and will be coming before the Regulatory agencies for approval. Improvement of monoclonal antibody therapeutics through technologies described here will pave the way of better clinical outcome for patients.

Human IgG1 antibody is a highly fucosylated glycoprotein. Two N-linked biantennary oligosaccharides consisting of core hepta-saccharide with variable addition of fucose, galactose, bisecting N-acetylglucosamine and sialic acid are present at Asn-297 of IgG1. Antibody glycosylation leads to unique biological functions known as "effector functions"—Antibody Dependent Cellular Cytotoxicity (ADCC) and Complement Dependent Cytotoxicity (CDC). ADCC is a cell mediated immune system where immune cells (like natural killer cells) lyse the target cells identified through antibodies against cell surface antigens.

The effector function of IgG molecule is defined by the interaction of antibody Fc region with leukocyte receptors, known as FcγRs or interactions with complement components. The composition of the oligosaccharide structure is critically important for effector function through FcγR binding (Shields et al. 2002; Shinkawa et al. 2003; Niwa et al. 2004; Niwa, Shoji-Hosaka, et al. 2004; Yamane-Ohnuki et al. 2004;). Crystal structure analysis of human IgG1 revealed intricate interaction of the oligosaccharide chains with the CH2 domain (Harris et al. 1998; Radaev et al. 2001).

The efficiency of the ADCC mechanism is considerably dependent on the level of antibody fucosylation; the lower the fucosylation, the higher is the rate of ADCC. Therefore, loss of fucosylation has significant biological consequences. The loss could be due to non-functional fucosyltransferase enzymes, resulting in non-fucosylation of cellular proteins. The absence of fucose from the primary N-acetylglucosamine results in the IgG1 antibody having increased binding affinity for the FcγRIIIα receptor, with consequent increase of 50-100 times higher efficacy of ADCC (Shinkawa et al. 2003). Improvement of ADCC with non-fucosylated IgG is directly proportional to the increased affinity for FcγRIIIα—this allows the non-fucosylated IgG Fc to overcome the competition from high concentrations of fucosylated IgG in normal serum. Plausible rationale for the increased affinity of non-fucosylated IgG Fc for FcγRIIIa may be the reduction or absence of steric inhibition at the receptor-ligand interface (Harris, 1998; Radaev, 2001).

In mammalian expression system, the enzyme α1-6 fucosyltransferase encoded by the Fut8 gene is responsible for transferring fucose moiety from GDP-fucose to N-acetylglucosamine of N-glycan chain in proteins (Miyoshi, 1999). Disruption of this gene function through various means leads to production of non-fucosylated proteins including antibodies (Naoko Yamane-Ohnuki, 2004).

Non-fucosylated forms of therapeutic antibodies developed in mammalian platforms, where fucose biosynthesis is impaired, may have clinical advantage over the fucosylated forms due to the enhanced efficiency of ADCC towards target tumor cells.

Historically, gene knock out systems completely depended on homologous recombination (HR) mediated targeted mutation, deletion and/or insertion. The HR system, although very specific, is highly inefficient, as thousands of clones need to be screened to find one mutated clone. Moreover, deleting allelic variations would take even further time and much larger screening. Multiple technologies have evolved in the last decade to achieve targeted gene modification using a combination of a DNA sequence recognition domain and a nuclease domain. These systems are highly efficient at identifying specific sites of interest and then introducing DNA strand breaks. DNA double-strand break (DSB) at genomic target locus activates DNA repair, which is utilized for modifying genes. The DNA damage response is highly conserved in eukaryotic cells. The concept of DSB-based genome engineering is easily transferrable between highly diverse organisms. Creating double strand break increases the frequency of gene knock out at targeted loci by thousand folds through homologous recombination and non-homologous end joining mechanisms.

In comparison Zinc Finger Nuclease (ZFN) requires three bases at the DNA level for each zinc finger tandem array. Moreover, target site overlap and cross-talk between individual fingers in a zinc-finger array considerably complicate the production of sequence-specific ZFNs. Additionally, major drawback of ZFNs includes elaborate and time-consuming experimental selection process to identify the ZFN motifs for specific DNA sequence recognition.

There are methods in the prior art for disruption of Fut8 genomic loci. However, none of the methods target the specific location on the FUT8 genomic loci by the TALEN technology.

The present disclosure overcomes the disadvantages or limitations associated with methods of the prior art by using the TALEN technology to target a specific location on the FUT8 genomic loci, which results in complete disruption of the FUT8 gene and related function, providing a cell that produces non-fucosylated proteins.

STATEMENT OF THE DISCLOSURE

Accordingly, the present disclosure relates to a DNA-binding domain of Transcription Activator like Effector Nuclease protein, wherein the DNA-binding domain comprises an amino acid sequence selected from the group consisting of SEQ ID No. 6, SEQ ID No.8, SEQ ID No. 11, SEQ ID No.14, SEQ ID No. 17, SEQ ID No.20, SEQ ID No. 23, SEQ ID No.26, SEQ ID No. 29, SEQ ID No.32, SEQ ID No. 35, SEQ ID No.38, and combinations thereof; a polynucleotide encoding the DNA-binding domain as above, wherein the polynucleotide comprises a nucleotide sequence selected from the group consisting of SEQ ID No. 7, SEQ ID No. 9, SEQ ID No. 12, SEQ ID No. 15, SEQ ID No. 18, SEQ ID No. 21, SEQ ID No. 24, SEQ ID No. 27, SEQ ID No. 30, SEQ ID No. 33, SEQ ID No. 36, SEQ ID No. 39 and combinations thereof; a Transcription Activator like Effector Nuclease protein comprising the DNA-binding domain as above and nuclease; a vector comprising a polynucleotide as above, a cell comprising a vector as above; a method of obtaining a cell without fucosylation activity, said method comprising steps of—a) Obtaining a Transcription Effector Like Activator Nuclease construct, and b) Transfecting a cell with the construct of step (a) to obtain a cell without fucosylation activity; a method of obtaining non-fucosylated protein, said method comprising steps of—a) Obtaining a Transcription Effector Like Activator Nuclease construct, b) Transfecting a cell with the construct of step (a) to obtain a cell without fucosylation activity, and c) Obtaining the non-fucosylated protein expressed by the cell of step (b); a non-fucosylated protein obtained by the method as above; and a composition comprising the non-fucosylated protein as above, optionally along with pharmaceutically acceptable excipient.

BRIEF DESCRIPTION OF THE DRAWINGS

The features of the present disclosure will become fully apparent from the following description taken in conjunction with the accompanying drawings. With the understanding that the drawings depict only several embodiments in accordance with the disclosure and are therefore, not to be considered limiting of its scope, the disclosure will be described with additional specificity and detail through use of the accompanying drawings:

FIG. 2 depicts the CHOK1 Fut8 amino-acid sequence.
FIG. 3 depicts Construct-pcDNA3.1-TALEN_L6.
FIGS. 7 and 8 depict the graphical result and fluorescence profile observed for the CHOK1 cell lines in the LCA-FITC Binding Assay.
FIGS. 10 and 11 depict in graphical representation and fluorescence profile observed for the CHOK1 cell lines in the LCA-FITC Binding Assay.
FIG. 16 depicts pictorial representation of the CHOK1 clones in the LCA selection assay.
FIGS. 22A and 22B depict nucleotide sequence analysis of genomic DNA of TALEN transfected CHOK1 FUT8 knock out clones and CHOK1 control cell lines.
FIG. 23 depicts amino acid alignment of Fut8 sequence with selected clonal sequences.

Figure 1:
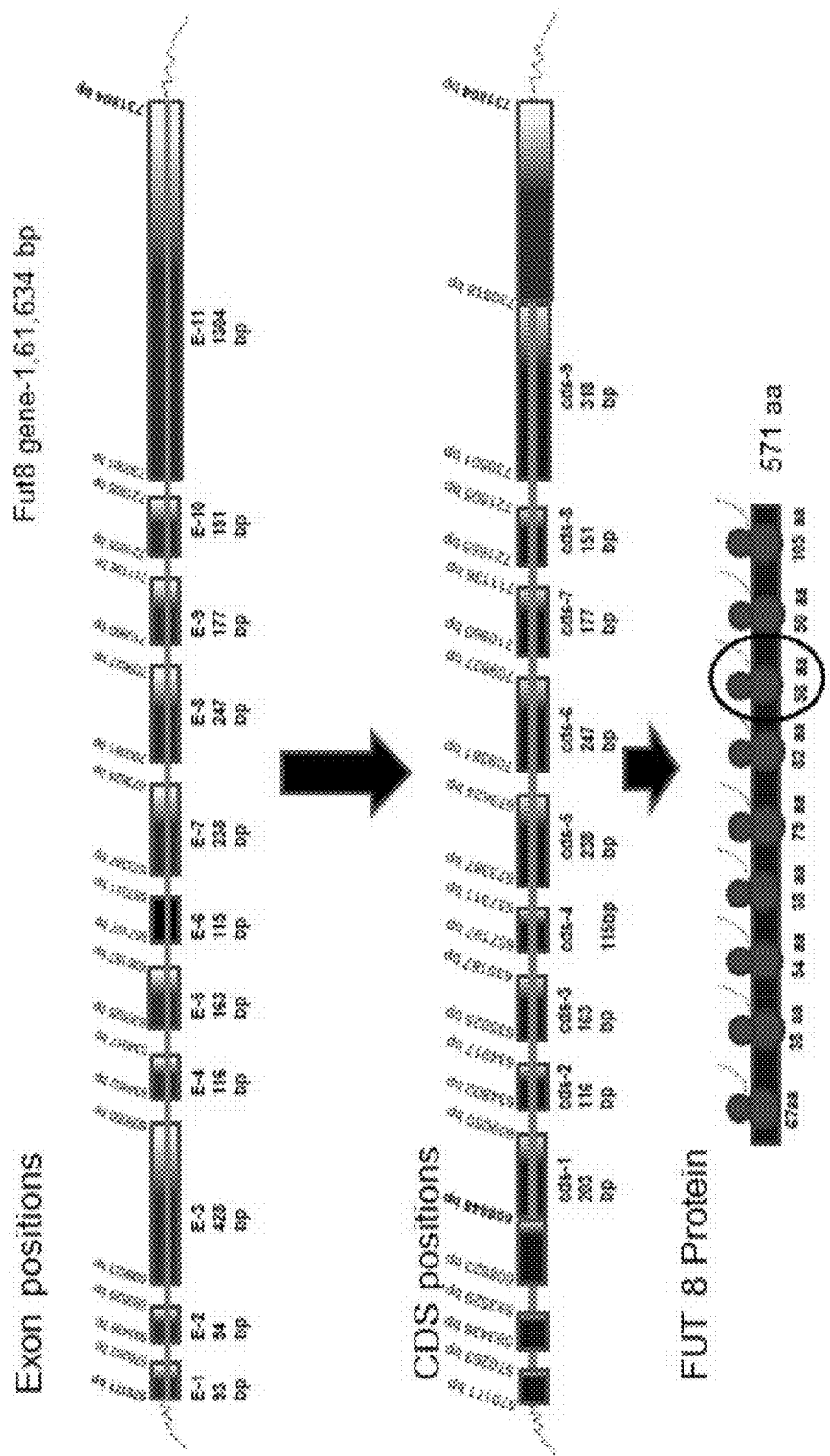
FIG. 1 depicts organization of the Fut8 gene sequence.

The various elements depicted in the drawings are merely representational and are not necessarily drawn to scale. Certain sections thereof may be exaggerated, while others may be minimized. The drawings are intended to illustrate example embodiments of the disclosure that can be understood and appropriately carried out by those of ordinary skill in the art.

DETAILED DESCRIPTION OF THE DISCLOSURE

The present disclosure relates to a DNA-binding domain of Transcription Activator like Effector Nuclease protein, wherein the DNA-binding domain comprises an amino acid sequence selected from the group consisting of SEQ ID No. 6, SEQ ID No.8, SEQ ID No. 11, SEQ ID No.14, SEQ ID No. 17, SEQ ID No.20, SEQ ID No. 23, SEQ ID No.26, SEQ ID No. 29, SEQ ID No.32, SEQ ID No. 35, SEQ ID No.38, and combinations thereof.

In an embodiment of the present disclosure, SEQ ID No. 6 binds SEQ ID No. 4 of the Fut8 gene sequence.

In another embodiment of the present disclosure, SEQ ID No.8 binds SEQ ID No. 5 of the Fut8 gene sequence.

In yet another embodiment of the present disclosure, SEQ ID No. 11 binds SEQ ID No. 10 of the Fut8 gene sequence.

In still another embodiment of the present disclosure, SEQ ID No.14 binds SEQ ID No. 13 of the Fut8 gene sequence.

In still another embodiment of the present disclosure, SEQ ID No. 17 binds SEQ ID No. 16 of the Fut8 gene sequence.

In still another embodiment of the present disclosure, SEQ ID No.20 binds SEQ ID No. 19 of the Fut8 gene sequence.

In still another embodiment of the present disclosure, SEQ ID No. 23 binds SEQ ID No. 22 of the Fut8 gene sequence.

In still another embodiment of the present disclosure, SEQ ID No.26 binds SEQ ID No. 25 of the Fut8 gene sequence.

In still another embodiment of the present disclosure, SEQ ID No. 29 binds SEQ ID No. 28 of the Fut8 gene sequence.

In still another embodiment of the present disclosure, SEQ ID No.32 binds SEQ ID No. 31 of the Fut8 gene sequence.

In still another embodiment of the present disclosure, SEQ ID No.35 binds SEQ ID No. 34 of the Fut8 gene sequence.

In still another embodiment of the present disclosure, SEQ ID No.38 binds SEQ ID No. 37 of the Fut8 gene sequence.

The present disclosure also relates to a polynucleotide encoding the DNA-binding domain as above, wherein the polynucleotide comprises a nucleotide sequence selected from the group consisting of SEQ ID No. 7, SEQ ID No. 9, SEQ ID No. 12, SEQ ID No. 15, SEQ ID No. 18, SEQ ID No. 21, SEQ ID No. 24, SEQ ID No. 27, SEQ ID No. 30, SEQ ID No. 33, SEQ ID No. 36, SEQ ID No. 39 and combinations thereof.

The present disclosure also relates to a Transcription Activator like Effector Nuclease protein comprising the DNA-binding domain as above and nuclease.

In an embodiment of the present disclosure, the nuclease is Fok1 endonuclease.

The present disclosure also relates to a vector comprising a polynucleotide as above.

The present disclosure also relates to a cell comprising a vector as above.

In an embodiment of the present disclosure, the cell is a mammalian cell.

The present disclosure also relates to a method of obtaining a cell without fucosylation activity, said method comprising steps of:
  a) Obtaining a Transcription Effector Like Activator Nuclease construct; and
  b) Transfecting a cell with the construct of step (a) to obtain a cell without fucosylation activity.

The present disclosure also relates to a method of obtaining non-fucosylated protein, said method comprising steps of:
  a) Obtaining a Transcription Effector Like Activator Nuclease construct;
  b) Transfecting a cell with the construct of step (a) to obtain a cell without fucosylation activity; and
  c) Obtaining the non-fucosylated protein expressed by the cell of step (b).

In an embodiment of the present disclosure, the non-fucosylated protein is a non-fucosylated antibody.

In another embodiment of the present disclosure, the non-fucosylated antibody is a non-fucosylated monoclonal antibody.

In yet another embodiment of the present disclosure, the Transcription Activator like Effector Nuclease is the nuclease protein as above; and the nuclease protein cleaves Fut8 gene sequence.

In still another embodiment of the present disclosure, the Fut8 gene sequence coding for α-1,6 Fucosyltransferase enzyme is cleaved at Exon 9.

In still another embodiment of the present disclosure, the Fucosyltransferase enzyme is mutated at an amino acid position selected from the group consisting of Arg-365, Arg-366, Asp-368, Lys-369, Glu-373, Tyr-382, Asp-409, Asp-410, Asp-453, Ser-469 and combinations thereof.

In still another embodiment of the present disclosure, the cell is mammalian cell.

In still another embodiment of the present disclosure, the cell is Chinese Hamster Ovary cell.

In still another embodiment of the present disclosure, the cell produces an endogenous non-fucosylated protein.

In still another embodiment of the present disclosure, the method further comprises a step of introducing a protein encoding gene into the cell and obtaining the non-fucosylated protein.

The present disclosure also relates to a non-fucosylated protein obtained by the method as above.

In an embodiment of the present disclosure, the protein is a non-fucosylated antibody.

The present disclosure also relates to a composition comprising the non-fucosylated protein as above, optionally along with pharmaceutically acceptable excipient.

In an embodiment of the present disclosure, the non-fucosylated protein is a non-fucosylated antibody.

The present disclosure relates to a method for obtaining non-fucosylated proteins, by disruption or inactivation of the fucosylating machinery in a cell.

In an embodiment, the non-fucosylated protein is a non-fucosylated antibody.

In a preferred but non-limiting embodiment, the non-fucosylated antibody is a non-fucosylated monoclonal antibody.

In the present disclosure, the terms "non-fucosylated antibody" and "afucosylated antibody" are used interchangeably and have the same meaning and scope.

The present disclosure particularly relates to disruption or inactivation of the FUT8 gene in a cell. The FUT8 gene encodes the enzyme α-1,6 fucosyltransferase.

In an embodiment of the present disclosure, the cell is a cell that naturally produces a protein.

In an embodiment of the present disclosure, the cell is a cell that naturally produces an antibody.

In an embodiment of the present disclosure, the cell is a cell that does not naturally produce a given protein, and a gene encoding the protein is introduced into the cell.

In an embodiment of the present disclosure, the cell is a cell that does not naturally produce an antibody, and a gene encoding an antibody is introduced into the cell.

In an embodiment of the present disclosure, the cell is a cell that naturally produces an antibody, and a gene encoding an antibody is introduced into the cell.

In an embodiment, the cell is a eukaryotic cell.

In an embodiment, the cell is mammalian cell.

In a non-limiting embodiment, the cell is Chinese Hamster Ovary cell.

In a non-limiting embodiment, the cell is Chinese Hamster Ovary K1 (CHOK1) cell.

In an embodiment, the CHOK1 cell is an antibody producing cell.

In an embodiment, the antibody produced by the method of the present disclosure is a therapeutic antibody.

In another embodiment, the CHOK1 cell is not an antibody producing cell, and a gene encoding an antibody is introduced into the cell.

In embodiments of the present disclosure, the cell line is selected from the group consisting of COS, CHO-S, CHO-K1, CHO-DG44, CHO-DUXB11, CHO-DUKX, CHOK1SV, VERO, MDCK, W138, V79, B14AF28-G3, BHK, HaK, NSO, SP2/0-Ag14, HeLa, HEK293-F, HEK293-H, HEK293-T, YB23HL.P2.G11.16Ag.20, perC6, Hybridoma cell which produces antibody, embryonic stem cell, Namalwa cell, insect cell line from *Spodoptera fugiperda* (Sf), *Pichia, Saccharomyces* and *Schizosaccharomyces*.

In an embodiment, the cell is referred to as a "Fucose Knockout" cell or "FKO" cell or "Fucose Knockout" platform or "FKO" platform.

In an embodiment, the cell is referred to as a Recombinant cell.

In an embodiment, TALEN (Transcription Activator-like Effector Nuclease) protein or enzyme is used to disrupt or inactivate the Fucosylation pathway of a cell.

In an embodiment, TALEN (Transcription Activator-like Effector Nuclease) protein or enzyme is used to disrupt or inactivate one or more genes of the Fucosylation pathway of a cell.

In an embodiment, TALEN (Transcription Activator-like Effector Nuclease) protein or enzyme is used to disrupt or inactivate or mutate gene selected from the group comprising α 1,6 Fucosyl transferase (Fut8 gene), GDP mannose 4, 6 dehydratase (GMD gene), GDP-keto-6 deoxymannose 3,5 epimerase 4-reductase (FX gene), GDP-beta-L-fucose pyrophosphorylase (GEPP gene), and Fucose kinase gene.

In an embodiment, the present disclosure relates to disruption of a combination of Fut8 gene and GMD gene by TALEN protein of the present disclosure.

In the de novo pathway of fucosylation, GDP-fucose is synthesized through conversion of GDP-mannose to GDP-4-keto-6-deoxy-mannose, catalyzed by the enzyme GDP-mannose 4, 6-dehydratase (GMD). This GDP-Fucose is then transported inside the golgi and used as a substrate for protein fucosylation by the enzyme α-(1-6) fucosyltransferase. The enzyme transfers the fucose moiety from GDP-fucose to N-acetyl glucosamine of the N-glycan chain.

In an embodiment, TALEN (Transcription Activator-like Effector Nuclease) protein or enzyme is used to disrupt the Fut8 gene encoding the α-1,6 fucosyltransferase enzyme.

In an embodiment of the present disclosure, the active site of the fucosyltransferase enzyme is targeted by TALEN protein.

In a particular embodiment, Exon 9 of the gene sequence of Fut8 is targeted by TALEN protein.

A TALEN protein is made of DNA binding domain and Nuclease domain. The DNA binding domain also has 2 parts—the TAL domain that identifies sequence left to the double strand break (DSB) target is termed as TAL-L and the TAL domain that identifies sequence right to the DSB target is termed as TAL-R. Both TAL-L and TAL-R domains are expressed as fusion protein with nuclease domain.

A family of proteins known as Transcription Activator like Effectors (TALE) have been identified from the plant pathogen *Xanthomonas*, which binds effector specific DNA sequences and activates transcription (Boch, 2009; Moscou, 2009). Naturally occurring TAL effectors in *Xanthomonas* bind to specific sequences of host DNA, altering the infected plant's gene expression.

The natural TAL effector proteins have two domains: an effector domain and a DNA-binding domain. The structure of the DNA-binding domain can be manipulated such that the domain binds specifically to any DNA sequence in the genome. These DNA-binding protein domains can be linked to a customised effector domain such as a nuclease, thus producing a chimeric TALEN (Transcription Activator-like Effector Nuclease) protein.

The DNA-binding domain which provides DNA sequence specificity of TALE/TALEN, consists of a variable number of amino acid repeats. Each repeat contains 33-35 amino acids and recognizes a single DNA base pair. The DNA recognition occurs via 2 hypervariable amino acid residues at positions 12 and 13 within each repeat, called Repeat-Variable Di-Residues (RVDs), which are critical for recognizing specific DNA sequences. The RVDs of the repeats in TAL effectors can be varied to create a TAL protein that recognizes a specific target DNA sequence. RVD is specific to a simple cipher like, NI=A, HD=C, NG=T, NN=G or A (Boch, 2009; Moscou, 2009). N, I, H, D, and G represent one letter amino acid codes.

The repeats of DNA binding domain are assembled in a TALE expression vector and co-expressed with a nuclease FokI endonuclease catalytic domain to create TALE nuclease (TALEN). Such TALENs, once expressed in cells, bind sequence specifically and create double stranded break; which is repaired by Non Homologous End Joining (NHEJ). During such cellular processes, mutations, i.e. either deletions and/or insertions within the gene sequence render non-functional protein products.

In embodiments of the present disclosure, the DNA binding domain is also referred to as the DNA recognition domain.

In an embodiment of the present disclosure, polynucleotides encoding said TALEN proteins are also provided, as are cells comprising said polynucleotides and proteins.

In a particular embodiment, nucleotides encoding for the DNA binding domain of TALEN protein are provided.

In another embodiment, nucleotides encoding for the effector domain or nuclease domain of TALEN protein are provided.

In an embodiment of the present disclosure, a DNA binding domain of Transcription Activator like Effector Nuclease protein comprises an amino acid sequence of SEQ ID No. 6.

In an embodiment of the present disclosure, a DNA binding domain of Transcription Activator like Effector Nuclease protein consists of an amino acid sequence of SEQ ID No. 6.

In an embodiment of the present disclosure, a DNA binding domain of Transcription Activator like Effector Nuclease protein comprises an amino acid sequence of SEQ ID No. 8.

In an embodiment of the present disclosure, a DNA binding domain of Transcription Activator like Effector Nuclease protein consists of an amino acid sequence of SEQ ID No. 8.

In an embodiment of the present disclosure, a DNA binding domain of Transcription Activator like Effector Nuclease protein comprises an amino acid sequence selected from SEQ ID No. 6 and SEQ ID No.8.

In an embodiment of the present disclosure, a DNA binding domain of Transcription Activator like Effector Nuclease protein comprises a nucleic acid sequence of SEQ ID No. 7.

In an embodiment of the present disclosure, a DNA binding domain of Transcription Activator like Effector Nuclease protein consists of a nucleic acid sequence of SEQ ID No. 7.

In an embodiment of the present disclosure, a DNA binding domain of Transcription Activator like Effector Nuclease protein comprises a nucleic acid sequence of SEQ ID No.9.

In an embodiment of the present disclosure, a DNA binding domain of Transcription Activator like Effector Nuclease protein consists of a nucleic acid sequence of SEQ ID No. 9.

In an embodiment of the present disclosure, a DNA binding domain of Transcription Activator like Effector Nuclease protein comprises a nucleic acid sequence selected from SEQ ID No. 7 and SEQ ID No.9.

In an embodiment of the present disclosure, a DNA binding domain of Transcription Activator like Effector Nuclease protein comprises an amino acid sequence of SEQ ID No. 11.

In an embodiment of the present disclosure, a DNA binding domain of Transcription Activator like Effector Nuclease protein consists of an amino acid sequence of SEQ ID No. 11.

In an embodiment of the present disclosure, a DNA binding domain of Transcription Activator like Effector Nuclease protein comprises an amino acid sequence of SEQ ID No. 14.

In an embodiment of the present disclosure, a DNA binding domain of Transcription Activator like Effector Nuclease protein consists of an amino acid sequence of SEQ ID No. 14.

In an embodiment of the present disclosure, a DNA binding domain of Transcription Activator like Effector Nuclease protein comprises an amino acid sequence selected from SEQ ID No. 11 and SEQ ID No.14.

In an embodiment of the present disclosure, a DNA binding domain of Transcription Activator like Effector Nuclease protein comprises a nucleic acid sequence of SEQ ID No. 12.

In an embodiment of the present disclosure, a DNA binding domain of Transcription Activator like Effector Nuclease protein consists of a nucleic acid sequence of SEQ ID No. 12.

In an embodiment of the present disclosure, a DNA binding domain of Transcription Activator like Effector Nuclease protein comprises a nucleic acid sequence of SEQ ID No.15.

In an embodiment of the present disclosure, a DNA binding domain of Transcription Activator like Effector Nuclease protein consists of a nucleic acid sequence of SEQ ID No. 15.

In an embodiment of the present disclosure, a DNA binding domain of Transcription Activator like Effector Nuclease protein comprises a nucleic acid sequence selected from SEQ ID No. 12 and SEQ ID No.15.

In an embodiment of the present disclosure, a DNA binding domain of Transcription Activator like Effector Nuclease protein comprises an amino acid sequence of SEQ ID No. 17.

In an embodiment of the present disclosure, a DNA binding domain of Transcription Activator like Effector Nuclease protein consists of an amino acid sequence of SEQ ID No. 17.

In an embodiment of the present disclosure, a DNA binding domain of Transcription Activator like Effector Nuclease protein comprises an amino acid sequence of SEQ ID No. 20.

In an embodiment of the present disclosure, a DNA binding domain of Transcription Activator like Effector Nuclease protein consists of an amino acid sequence of SEQ ID No. 20.

In an embodiment of the present disclosure, a DNA binding domain of Transcription Activator like Effector Nuclease protein comprises an amino acid sequence selected from SEQ ID No. 17 and SEQ ID No.20.

In an embodiment of the present disclosure, a DNA binding domain of Transcription Activator like Effector Nuclease protein comprises a nucleic acid sequence of SEQ ID No. 18.

In an embodiment of the present disclosure, a DNA binding domain of Transcription Activator like Effector Nuclease protein consists of a nucleic acid sequence of SEQ ID No. 18.

In an embodiment of the present disclosure, a DNA binding domain of Transcription Activator like Effector Nuclease protein comprises a nucleic acid sequence of SEQ ID No.21.

In an embodiment of the present disclosure, a DNA binding domain of Transcription Activator like Effector Nuclease protein consists of a nucleic acid sequence of SEQ ID No. 21.

In an embodiment of the present disclosure, a DNA binding domain of Transcription Activator like Effector Nuclease protein comprises a nucleic acid sequence selected from SEQ ID No. 18 and SEQ ID No.21.

In an embodiment of the present disclosure, a DNA binding domain of Transcription Activator like Effector Nuclease protein comprises an amino acid sequence of SEQ ID No. 23.

In an embodiment of the present disclosure, a DNA binding domain of Transcription Activator like Effector Nuclease protein consists of an amino acid sequence of SEQ ID No. 23.

In an embodiment of the present disclosure, a DNA binding domain of Transcription Activator like Effector Nuclease protein comprises an amino acid sequence of SEQ ID No. 26.

In an embodiment of the present disclosure, a DNA binding domain of Transcription Activator like Effector Nuclease protein consists of an amino acid sequence of SEQ ID No. 26.

In an embodiment of the present disclosure, a DNA binding domain of Transcription Activator like Effector Nuclease protein comprises an amino acid sequence selected from SEQ ID No. 23 and SEQ ID No.26.

In an embodiment of the present disclosure, a DNA binding domain of Transcription Activator like Effector Nuclease protein comprises a nucleic acid sequence of SEQ ID No. 24.

In an embodiment of the present disclosure, a DNA binding domain of Transcription Activator like Effector Nuclease protein consists of a nucleic acid sequence of SEQ ID No. 24.

In an embodiment of the present disclosure, a DNA binding domain of Transcription Activator like Effector Nuclease protein comprises a nucleic acid sequence of SEQ ID No.27.

In an embodiment of the present disclosure, a DNA binding domain of Transcription Activator like Effector Nuclease protein consists of a nucleic acid sequence of SEQ ID No. 27.

In an embodiment of the present disclosure, a DNA binding domain of Transcription Activator like Effector Nuclease protein comprises a nucleic acid sequence selected from SEQ ID No. 24 and SEQ ID No.27.

In an embodiment of the present disclosure, a DNA binding domain of Transcription Activator like Effector Nuclease protein comprises an amino acid sequence of SEQ ID No. 29.

In an embodiment of the present disclosure, a DNA binding domain of Transcription Activator like Effector Nuclease protein consists of an amino acid sequence of SEQ ID No. 29.

In an embodiment of the present disclosure, a DNA binding domain of Transcription Activator like Effector Nuclease protein comprises an amino acid sequence of SEQ ID No. 32.

In an embodiment of the present disclosure, a DNA binding domain of Transcription Activator like Effector Nuclease protein consists of an amino acid sequence of SEQ ID No. 32.

In an embodiment of the present disclosure, a DNA binding domain of Transcription Activator like Effector Nuclease protein comprises an amino acid sequence selected from SEQ ID No. 29 and SEQ ID No.32.

In an embodiment of the present disclosure, a DNA binding domain of Transcription Activator like Effector Nuclease protein comprises a nucleic acid sequence of SEQ ID No. 30.

In an embodiment of the present disclosure, a DNA binding domain of Transcription Activator like Effector Nuclease protein consists of a nucleic acid sequence of SEQ ID No. 30.

In an embodiment of the present disclosure, a DNA binding domain of Transcription Activator like Effector Nuclease protein comprises a nucleic acid sequence of SEQ ID No.33.

In an embodiment of the present disclosure, a DNA binding domain of Transcription Activator like Effector Nuclease protein consists of a nucleic acid sequence of SEQ ID No. 33.

In an embodiment of the present disclosure, a DNA binding domain of Transcription Activator like Effector Nuclease protein comprises a nucleic acid sequence selected from SEQ ID No. 30 and SEQ ID No.33.

In an embodiment of the present disclosure, a DNA binding domain of Transcription Activator like Effector Nuclease protein comprises an amino acid sequence of SEQ ID No. 35.

In an embodiment of the present disclosure, a DNA binding domain of Transcription Activator like Effector Nuclease protein consists of an amino acid sequence of SEQ ID No. 35.

In an embodiment of the present disclosure, a DNA binding domain of Transcription Activator like Effector Nuclease protein comprises an amino acid sequence of SEQ ID No. 38.

In an embodiment of the present disclosure, a DNA binding domain of Transcription Activator like Effector Nuclease protein consists of an amino acid sequence of SEQ ID No. 38.

In an embodiment of the present disclosure, a DNA binding domain of Transcription Activator like Effector Nuclease protein comprises an amino acid sequence selected from SEQ ID No. 35 and SEQ ID No.38.

In an embodiment of the present disclosure, a DNA binding domain of Transcription Activator like Effector Nuclease protein comprises a nucleic acid sequence of SEQ ID No. 36.

In an embodiment of the present disclosure, a DNA binding domain of Transcription Activator like Effector Nuclease protein consists of a nucleic acid sequence of SEQ ID No. 36.

In an embodiment of the present disclosure, a DNA binding domain of Transcription Activator like Effector Nuclease protein comprises a nucleic acid sequence of SEQ ID No.39.

In an embodiment of the present disclosure, a DNA binding domain of Transcription Activator like Effector Nuclease protein consists of a nucleic acid sequence of SEQ ID No. 39.

In an embodiment of the present disclosure, a DNA binding domain of Transcription Activator like Effector Nuclease protein comprises a nucleic acid sequence selected from SEQ ID No. 36 and SEQ ID No.39.

In embodiments of the present disclosure, SEQ ID No. 6 works in combination with SEQ ID No.8 as DNA binding domain of TALEN protein.

In embodiments of the present disclosure, SEQ ID No. 11 works in combination with SEQ ID No.14 as DNA binding domain of TALEN protein.

In embodiments of the present disclosure, SEQ ID No. 17 works in combination with SEQ ID No.20 as DNA binding domain of TALEN protein.

In embodiments of the present disclosure, SEQ ID No. 23 works in combination with SEQ ID No.26 as DNA binding domain of TALEN protein. In embodiments of the present disclosure, SEQ ID No. 29 works in combination with SEQ ID No.32 as DNA binding domain of TALEN protein.

In embodiments of the present disclosure, SEQ ID No. 35 works in combination with SEQ ID No.38 as DNA binding domain of TALEN protein.

In embodiments of the present disclosure, each unit of the DNA binding domain is prepared as a construct with Left TALEN nucleotide sequence with Nuclease.

In embodiments of the present disclosure, each unit of the DNA binding domain is prepared as a construct with Right TALEN nucleotide sequence with Nuclease.

Provided below is a table providing the nucleotide sequences, amino acid sequences and binding sites on Fut8 gene for TALEN proteins 1 to 6 of the present disclosure.

TABLE 1

| Sl No. | TALEN Protein | Amino Acid Sequence | Nucleotide Sequence | Binding site on Fut8 gene |
|---|---|---|---|---|
| 1 | L1 | SEQ ID No. 11 | SEQ ID No. 12 | SEQ ID No. 10 |
| 2 | R1 | SEQ ID No. 14 | SEQ ID No. 15 | SEQ ID No. 13 |
| 3 | L2 | SEQ ID No. 17 | SEQ ID No. 18 | SEQ ID No. 16 |
| 4 | R2 | SEQ ID No. 20 | SEQ ID No. 21 | SEQ ID No. 19 |
| 5 | L3 | SEQ ID No. 23 | SEQ ID No. 24 | SEQ ID No. 22 |
| 6 | R3 | SEQ ID No. 26 | SEQ ID No. 27 | SEQ ID No. 25 |
| 7 | L4 | SEQ ID No. 29 | SEQ ID No. 30 | SEQ ID No. 28 |
| 8 | R4 | SEQ ID No. 32 | SEQ ID No. 33 | SEQ ID No. 31 |
| 9 | L5 | SEQ ID No. 35 | SEQ ID No. 36 | SEQ ID No. 34 |
| 10 | R5 | SEQ ID No. 38 | SEQ ID No. 39 | SEQ ID No. 37 |
| 11 | L6 | SEQ ID No. 6 | SEQ ID No. 7 | SEQ ID No. 4 |
| 12 | R6 | SEQ ID No. 8 | SEQ ID No. 9 | SEQ ID No. 5 |

In an embodiment of the present disclosure, the nuclease component of TALEN protein is any nuclease having a target site in a FUT8 gene. In an embodiment of the present disclosure, the nuclease is a homing endonuclease. In another embodiment, the nuclease is a meganuclease. It is also known that the specificity of homing endonucleases and meganucleases can be engineered to bind non-natural target sites. Further, in exemplary embodiments, homing endonucleases include I-SceI, I-CeuI, PI-PspI, PI-Sce, I-SceIY, I-CsmI, I-PanI, I-SceII, I-PpoI, I-SceIII, I-CreI, I-TevI, I-TevII and I-TevIII. Their recognition sequences are known.

In an embodiment, a combination of one or more of the above-mentioned nucleases is used with the DNA binding domain of the TALEN protein.

In an embodiment, transfection is used to introduce a TALEN protein into a cell. Though a lipofection protocol is provided as an exemplary embodiment, any method of transfection known to one skilled in the art is equally applicable to the methods of the present disclosure.

In another embodiment, the present disclosure provides methodologies for producing recombinant proteins in any host cell where the host cell has endogenous FUT8 gene expression which is targeted through TALEN technology to disrupt endogenous FUT8 gene as described herein. The resulting cell line is null for FUT8 gene expression and is further used for expression of gene of interest.

In the present disclosure, nineteen FUT8 knock out clonal cell lines are created from a screen of less than 280 cell lines. In comparison, only three FUT8−/− cell lines could be selected from approximately 120,000 clonal cell lines as reported in the prior art.

The specificity, safety and simplicity of the protocol are some of the advantages offered by TALEN and the method of the present disclosure over the prior art methods. TALEN mediated gene disruption provides a unique advantage of "one repeat one base" code that allows customized TALE repeat arrays to recognize user defined target sequence of any complexity. TALEN constructs are more effective than ZFN in terms of genome editing efficiency and significantly less toxic, thereby allowing higher efficiency in generating mutant clones against a particular locus. In the present disclosure, FUT8 genomic loci are targeted for sequence specific deletions through TALENs.

The methodology described herein has achieved an efficiency of more than 6.5% success rate of generating CHOK1 FUT8 knock out cell lines (19 CHOK1 knock out cell lines from a screen of less than 280 clonal cell populations). This unanticipated achievement following the methodology and the specific TALEN constructs of the present disclosure has vastly improved the FUT8 knock out cell line development. Also, the present disclosure has used only one set of TALEN constructs targeting a very specific genomic location in the CHOK1 FUT8 DNA sequence. Surprisingly, the TALEN constructs result in not only disrupting the targeted amino acids but also produced long deletions which introduced frame shift mutations and early stop codon. Thereby, the present disclosure has achieved CHOK1 FUT8 knock out cell lines with very minimal DNA modifications at the target locus as well as large genome level modifications at the targeted FUT8 locus. Generation of such a large number of CHOK1 FUT8 knock out cell lines is unexpected, considering the small number of clonal populations screened for fucose knock out phenotype. This surprising achievement allowed us to screen multiple CHOK1 FUT8 knock out cell lines to establish best performing clonal lines for over expression of monoclonal antibody.

In an embodiment, the gene of interest is introduced in the resulting cell line through an expression vector comprising DNA sequences encoding the protein of interest, thereby producing recombinant protein.

In another embodiment, the expressed protein of interest includes antibodies, including monoclonal antibodies.

In embodiments, inactivating a FUT8 gene results in a cell line which produces recombinant proteins at higher levels.

In certain embodiments, inactivating a FUT8 gene provides a cell line in which one or more activities (functions) of a protein is increased, as compared to proteins produced in cells where the FUT8 gene is not inactivated.

In an embodiment, the non-fucosylated protein produced by the cell is a non-fucosylated antibody.

In a non-limiting embodiment, the non-fucosylated protein is a non-fucosylated IgG1 antibody, and preferably a non-fucosylated IgG1 monoclonal antibody.

In an embodiment, the non-fucosylated antibody exhibits greater effector function than a corresponding fucosylated antibody.

In an embodiment, the non-fucosylated antibody exhibits more efficacious therapeutic properties than a corresponding fucosylated antibody.

In an embodiment, the non-fucosylated antibody exhibits higher Antibody dependent Cellular Toxicity (ADCC) than a corresponding fucosylated antibody.

In the present disclosure, the methods, preparation and use of the proteins disclosed employ, unless otherwise indicated, conventional techniques in molecular biology, biochemistry, computational chemistry, cell culture, recombinant DNA technology, Polymerase Chain Reaction (PCR) and related fields. These techniques, their principles, and requirements are explained in the literature and known to a person skilled in the art. The techniques for determining nucleic acid and amino acid sequence identity are known to one skilled in the art.

The cell with the disrupted fucosylation machinery is a cell that produces antibodies, or a cell in which a gene encoding an antibody is introduced before or after disruption of fucosylation.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid.

The term "antibody" used here includes both polyclonal and monoclonal antibody preparations and also includes the following: Chimeric antibody molecules, F(ab')2 and F(ab) fragments, Fv molecules, single chain Fv molecules (ScFv), dimeric and trimeric antibody fragments, minibodies, humanized monoclonal antibody molecules, human antibodies, fusion proteins comprising of Fc region of antibody and any functional fragments arising out of these molecules, where derivative molecules retain immunological functionality of the parent antibody molecule.

The term "monoclonal antibody" in the present disclosure, refers to an antibody composition having a homogeneous antibody population. The antibody is not limited to the species or source of the antibody or by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

It is to be noted that clones/cells of the present disclosure are referred to by terms such as TAL R4 #003, TAL R4 #013 etc., which are internal denominations and do not represent any particular feature of the cell.

In an embodiment, a composition comprising the non-fucosylated antibody, optionally along with a pharmaceutically acceptable carrier or additive or excipient is provided. Pharmaceutically acceptable carrier or additive or excipient is determined by the composition being administered, as well as by the particular method used to administer the composition and are known to a person skilled in the art.

All sequences provided in the present disclosure are read in the 5' to 3' direction, unless stated otherwise.

Excipients are important for achieving protein stabilization and improving other qualities of biologics. A variety of excipients are added to compositions to stabilize proteins, act as antimicrobials, aid in the manufacture of the dosage form, control or target drug delivery, and minimize pain upon injection.

Excipients can be broadly divided into five categories based on their modes of action:

1. Protein stabilizers: These excipients stabilize the protein native conformation. Examples include polyols, sugars, amino acids, amines, and salting out salts. Sucrose and trehalose are the most frequently used sugars and large polyols are better stabilizers than smaller polyols.
2. Polymers and proteins: Hydrophilic polymers, such as Polyethylene Glycols (PEGs), polysaccharides, and inert proteins, are used non-specifically to stabilize proteins and enhance protein assembly. Examples include Dextran, Hydroxyl Ethyl Starch (HETA), PEG-4000, and gelatin.
3. Surfactants: Non-ionic surfactants are widely used to stabilize proteins, suppress aggregation, and assist in protein refolding. Polysorbate 80 and Polysorbate 20, also known as Tween 80 and Tween 20, respectively, are generally used in mAb therapeutics. Other examples include Brij 35, Triton X-10, Pluronic F127, and Sodium Doceyl Sulfate (SDS).
4. Amino acids: These excipients stabilize proteins by a variety of mechanisms. Examples include Histidine, Arginine, and Glycine. Other amino acids used as formulation excipients include Methionine, Proline, Lysine, Glutamic acid, and Arginine mixtures.
5. Preservatives: These compounds are included in formulations to prevent microbial growth. Examples include Benzyl alcohol, m-Cresol, and Phenol.

The biological material used in the present disclosure is obtained from outside India.

One of the most important aspects of the present disclosure is the targeting of the active site of the enzyme α 1,6-fucosyltransferase, encoded by the Fut8 gene. This active site corresponds to the Exon 9 on the mRNA of the Fut8 gene. This targeting is not a random selection, but has been arrived at, in the present disclosure, by experimentation to determine the highly specific location on the gene or enzyme, the disruption of which ensures that partial fucosylation that is caused by truncated or partially functional enzyme is avoided.

Thus, targeting the region equivalent to the active site of the enzyme ensures complete disruption of the Fut8 gene and provides efficacious results in comparison to either a technique that is unable to target a precise location on the Fut8 gene or a technique that targets another location on the Fut8 gene, which might result in partial disruption of Fut8 gene and enzyme activity. A cell with partially functional fucosylated machinery produces partially fucosylated proteins, which exhibits lower therapeutic functions as compared to non-fucosylated proteins. The cells produced by the method of the present disclosure produce completely or 100% non-fucosylated proteins, including 100% non-fucosylated antibodies.

The present disclosure introduces mutations at critical amino acid positions at the active site of the FUT8 codon sequence through TALENs. It has been reported that Arg365 and Arg366 in human FUT8 gene play an important role in catalytic function of α-1,6 fucosyltransferase (Takahashi 2000). Few other critical amino acids are also reported to be conserved in FUT8 gene across species.

Figure 24:
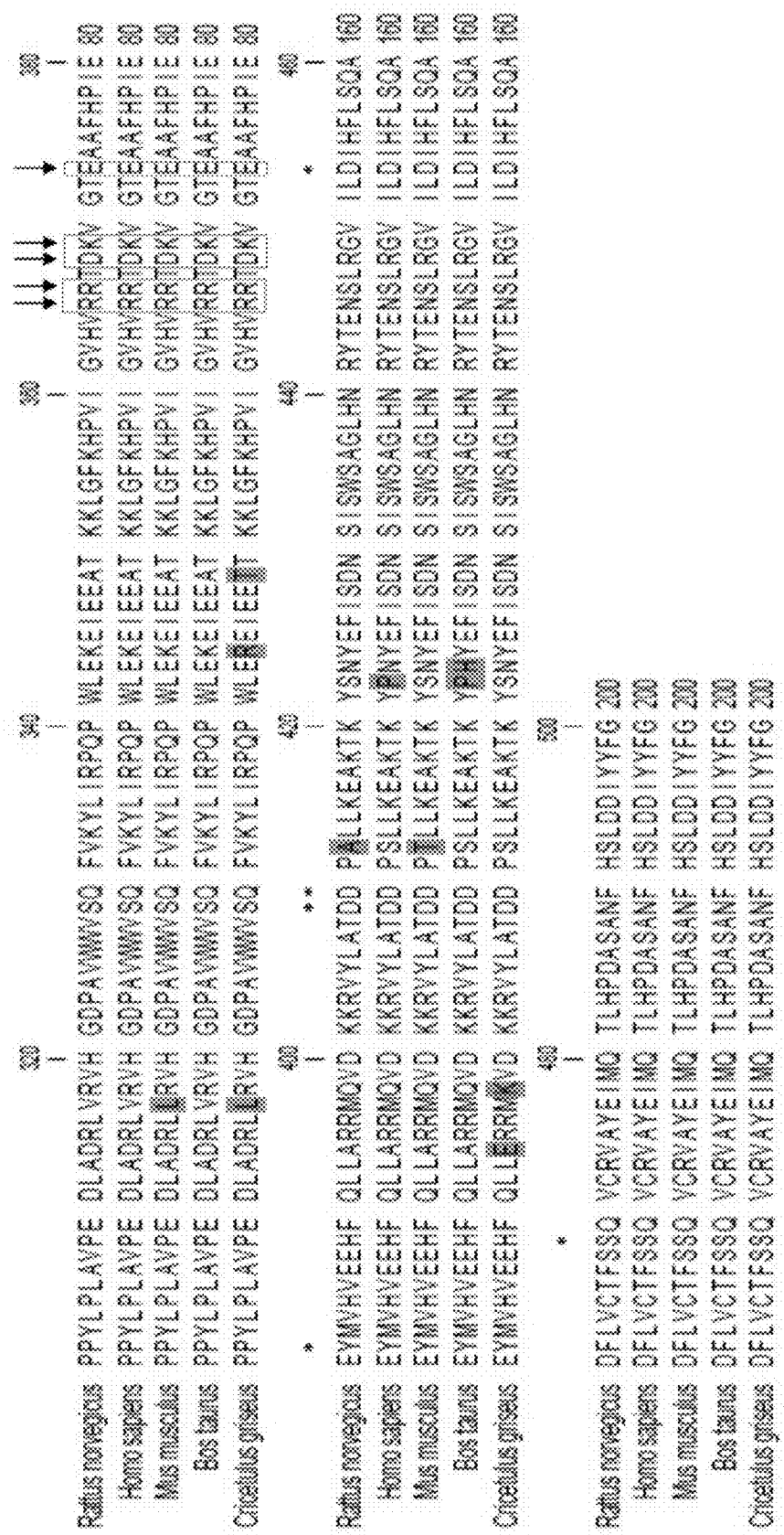
FIG. 24 depicts alignment of FUT8 amino acid sequence of rat, human, mouse, cattle and Chinese hamster from amino acid position 300 to 500 spanning over the three critical motifs.

FIG. 24 of the present disclosure depicts alignment of FUT8 amino acid sequence of rat, human, mouse, cattle and Chinese hamster from amino acid position 300 to 500 spanning over the three critical motifs. Amino acids 365, 366, 368, 369 and 373 are marked with open box and arrow marks are targeted in this study. Other important amino acids 382, 409, 410, 453 and 469 are marked with asterisks. Amino acids in shaded box indicate residues not aligned with consensus sequence.

In the present disclosure, the FUT8 amino acid sequence from CHOK1 genomic database is analyzed and it is confirmed that these critical amino acids are conserved in the FUT8 gene derived from CHOK1 cell line as well. Sequence specific TALENs are designed, targeting these amino acid motifs to introduce genomic modifications.

It is stated that mutation of these critical amino acids provides complete disruption of FUT8 gene functionality. Gene targeting using TALEN technology is a novel approach to create a Fucose knock out cell line platform. TALEN transfected cells are screened through FUT8 gene functionality assays. Selected clones are confirmed through sequencing of genomic FUT8 loci for mutations. The mutant fucose knock out CHOK1 cell line is then used for expressing non-fucosylated therapeutic proteins, including non-fucosylated therapeutic monoclonal antibodies or part of antibody.

The complete Fut8 gene locus in CHOK1 cell genome is analyzed from publicly available genome database. NW_003613860 consisting of 1822872 bp, is obtained from Pubmed. The complete Fut8 gene locus (NW_003613860.1) from this data corresponds to the region from 570171-731804 bases. This corresponds to a total of 161634 bp. The Pubmed accession number for the coding region or mRNA of the Fut8 gene is XM_003501735.1.

The target sequence encompasses the Fut8 gene responsible for expression of the FUT8 gene product, α-1,6 fucosyltransferase enzyme. The enzyme catalyzes transfer of fucose moiety from GDP-fucose to N-acetylglucosamine via α-1,6 linkage.

The Spidey alignment tool (http://www.ncbi.nlm.nih.gov/spidey/spideyweb.cgi) is used to identify the exons in the Fut8 genomic DNA by aligning the mRNA sequence with the genomic DNA sequence. A total of 11 exons with the boundaries as shown below in Table 2 are identified. A 100% identity between the genomic DNA and mRNA sequence is observed. Organization of the Fut8 gene showing all the 11 exons is shown in FIG. 1 of the present disclosure.

TABLE 2

Characterization of Fut8 mRNA

| EXON | Genomic coordinates | mRNA coordinates | Length (nucleotides) |
|---|---|---|---|
| Exon 1 | 570171-570263 | 1-93 | 93 |
| Exon 2 | 593436-593529 | 94-187 | 94 |
| Exon 3 | 608623-609050 | 188-615 | 428 |
| Exon 4 | 634802-634917 | 616-731 | 116 |
| Exon 5 | 635025-635187 | 732-894 | 163 |
| Exon 6 | 657197-657311 | 895-1009 | 115 |
| Exon 7 | 673387-673624 | 1010-1247 | 238 |
| Exon 8 | 709381-709627 | 1248-1494 | 247 |
| Exon 9 | 710960-711136 | 1495-1671 | 177 |
| Exon 10 | 721655-721805 | 1672-1822 | 151 |
| Exon 11 | 730501-731804 | 1823-3126 | 1304 |

FUT8 enzyme functionalities through site directed mutagenesis studies of critically important amino acid residues in the catalytic domain has been confirmed. Two Arginine residues at positions 365 and 366 along with Asp-368, Lys-369 and Glu-373 revealed reduction of FUT8 catalytic activity as measured through fluorescence based assays.

SEQ ID No.1 of the present disclosure indicates the Exon 9 of the genomic DNA sequence in the Fut8 gene of CHO (Chinese Hamster or *Cricetulus griseus*), for TALEN target. The nucleotide sequence corresponding to Arg 365, Arg 366, Asp 368, Lys 369 and Glu 373 are indicated in bold and underline in the sequence of Exon 9, provided below.

AGTCCATGTCAGACGCACTGACAAAGTGGAAGAGAAGCAGCCTTCCATC

CCATTGAGGAATACATGGTACACGTTGAAGAACATTTTCAGCTTCTCGAA

CGCAGAATGAAAGTGGATAAAAAAAGAGTGTATCTGGCCACTGATGACCC

TTCTTTGTTAAAGGAGGCAAAGACAAA

In the sequence above:
AGA codes for Arginine at position 365
CGC codes for Arginine at position 366
GAC codes for Aspartate at position 368
AAA codes for Lysine at position 369
GAA codes for Glutamic Acid at position 373

TALENs specifically targeting the amino acid codon sequences in genomic locations are designed, synthesized and cloned in expression vectors, for e.g. pcDNA3.1. The TALEN constructs are transiently transfected in CHOK1 cells; the cells are plated in 96 well plates for single colony generation. Each clone is then screened for FUT8 gene expression using fluorescence based Lens Culinaris Agglutinin assay (LCA). Clones positive for FUT8 gene disruption are further tested through enzymatic assays and kinetic analysis of mutant alleles of FUT8 gene. Finally, the genomic sequence at the FUT8 loci is analyzed for any mutation carried out through TALENs. These mutations involve deletions or insertions, thereby introducing frame shift mutations of the FUT8 codon sequence, and rendering the sequence disrupted and the enzyme non-functional.

The fucose knock out CHOK1 cell line derived from above mentioned process is used as a cell line platform for expressing proteins, monoclonal antibodies, peptides, fusion proteins of therapeutic purposes, biomarker development, diagnostic and prognosis uses.

The present disclosure is further described with reference to the following examples, which are only illustrative in nature and should not be construed to limit the scope of the present disclosure in any manner.

Reagent Preparation
Advanced DMEM Complete Growth Medium—500 ml
1. 50 ml FBS (final concentration 10%) is added to the upper chamber of the 500 ml filter unit.
2. 10 ml of 200 mM glutamine (final concentration 4 mM) is added.
3. 5 ml of 100× Pen-strep solution (final concentration 1×) is added.
4. The volume is adjusted up to 500 ml with advanced DMEM media.
5. The complete media is filtered through 0.22 μm filter.
6. The upper chamber is dismantled and the reservoir or media bottle is closed.
7. The media can be used within 30 days of preparation.
8. The media is stored at 2° C.-8° C. and away from continuous exposure to light.
9. In cases where LCA selection media is prepared, 10 milliliter of 10 mg/milliliter stock LCA reagent is mixed with 500 milliliter of prepared DMEM media to achieve final 200 μg/ml LCA concentration in DMEM media.

Materials & Equipment
1. Bio safety cabinet
2. Sorvall ST 16R centrifuge
3. Water bath
4. Inverted phase contrast microscope
5. CO$_2$ incubator
6. Millipore GUAVA 8HT easyCyte benchtop flow cytometer
7. Vi-cell XR cell viability analyser
8. Hemocytometer
9. Refrigerator
10. Eppendorf minispin centrifuge
11. Micropipettes
12. Micro tips
13. 96 well tissue culture plates
14. 12 well tissue culture plates
15. 6 well tissue culture plates
16. Serological pipettes (10 ml, 25 ml and 50 ml)
17. 1000 ml filtration unit-0.22 μm pore size
18. 70% ethanol
19. Advanced DMEM
20. Dulbecco's Phosphate Buffered Saline (DPBS)

21. Fetal Bovine Serum (FBS)
22. Penicillin Streptomycin (Penstrep)
23. Glutamine
24. 0.05% Trypsin EDTA
25. 0.4% Trypan blue
26. Microfuge tubes (1.5 ml and 2 ml)
27. Falcon tubes (15 ml and 50 ml)
28. Bovine serum albumin fraction V
29. Fluorescein Lens Culinaris Agglutinin (LCA-FITC)
30. Fluorescein Streptavidin (Strep-FITC)

TABLE 3

Reagents used in this disclosure

| S. No. | Reagent | Composition |
|---|---|---|
| 1 | Agarose | Agarose (SIGMA, Cat-A9539) |
| 2 | 1 kb DNA ladder | 1 kb ladder (Thermoscientific Cat-SM0311) |
| 3 | 100 bp DNA ladder | 100 bp ladder (Thermoscientific, Cat-SM0322) |
| 4 | QIAGEN genomic DNA isolation kit | DNeasy Blood & Tissue Kit (QIAGEN, Cat-69504) |
| 5 | Taq DNA polymerase | Taq DNA polymerase with thermopol (NEB, Cat-M0267 & M0273L) |
| 6 | Phusion high-fidelity DNA polymerase | Phusion high-fidelity DNA polymerase (Thermo Scientific, Cat-F530L) |
| 7 | Ins TAclone PCR cloning | TA cloning vector pTZ57R/T (Thermo Scientific, Cat- K1214) |
| 8 | Competent cells DH10B cells | Max Efficiency DH10B competent cells (Invitrogen, Cat- 18297-010) |
| 9 | Competent cells DH5alpha cells | NEB 5-alpha competent cells (NEB, Cat-C2987P) |
| 10 | Ethanol absolute (99.9%) | Sdfine chem, Cat-58051 L05 |
| 11 | Plasmid DNA isolation | QiaPrep spin miniprep Kit (QIAGEN, Cat-27104) |
| 12 | DNA elution kit | QIAGEN Gel Extraction kit (Cat-20021 and 20051) |
| 13 | Restriction enzymes | EcoRI-HF (NEB, Cat-R3101) Hind III-HF (NEB, Cat-R3104) |
| 14 | T4 ligase | T4 DNA Ligase (NEB, Cat-M0202) |

TABLE 4

Media and buffers used in this disclosure

| S. No. | Media/Buffers | Composition |
|---|---|---|
| 1 | 6X loading DNA dye | Sucrose-4 g, Bromophenol blue-0.025 g, made up to 10 mL using purified water. |
| 3 | 50× TAE buffer | Tris base-121 g, Glacial acetic acid-28.6 mL, EDTA (0.5M) pH-8 50 mL, made up to a volume of 500 mL with purified water. |

EXAMPLE 1

Designing of Talen Protein

The objective of this experiment is to design TALEN (Transcription activator-like effector nuclease) for specific inactivation of FUT8 alleles.

1.1-Rationale for Targeting Specific Genomic Sequence in FUT 8 Locus

FUT8 is comprised of three domains, an N-terminal coiled-coil domain, a catalytic domain, and a C-terminal SH3 domain. The C-terminal part of the catalytic domain of FUT8 includes a Rossmann fold with three conserved regions in α1,6-fucosyltransferases; α 1,2-fucosyltransferases; and protein O-fucosyltransferases. Furthermore, site-directed mutagenesis experiment shows that several residues, which are all highly conserved in the three fucosyltransferases in this fold, are essential for the enzyme activity of FUT8.

The putative catalytic domain is comprised of two structures, an open sheet a/b structure and a Rossmann fold which is frequently found in nucleotide binding proteins including glycosyltransferases. Ten amino acid residues, Arg 365, Arg 366, Asp-368, Lys-369, Glu-373, Tyr-382, Asp-409, Asp-410, Asp-453, and Ser-469 of human FUT8 enzyme protein are perfectly conserved among various species, including vertebrates, insect, nematode, and ascidian as observed in FIG. 24 of the present disclosure.

To understand the contribution of specific amino acid sequence in FUT8 gene in α 1,6 fucosyltransferase activity, regions of FUT8 amino acid sequence are compared among multiple species. The analysis shows many conserved regions, among them residues in 361-370 are observed to be highly homologous and this region is an essential part of the catalytic domain of the enzyme. The alignment shows that the enzyme sequences constitute highly conserved amino acid residues at position Arg 365, Arg 366, Asp-368, Lys-369, Glu-373. Thus, these amino acid positions are the target of TALEN proteins in the method of the present disclosure.

1.2—TALEN Constructs

TALEN constructs function in dimeric forms, referred to as left and right TALENS, based on their position on the genomic DNA sequence. The sequence in between the two TALEN binding sites is targeted to create double stranded break using FokI endonuclease and is referred to as the spacer sequence, Each TALEN is designed to recognize and bind to a 20 bp DNA sequence. The left and right TALENs target DNA sequences in the opposite strands. TALEN enzymes are constructed as fusion proteins involving TALE DNA binding domain and monomeric FokI nuclease domain. FokI nuclease is functional only in dimeric catalytic domain configuration. FokI dimerization happens once the right and left TALEN fusion proteins bind a spacing of approximately 14-20 bp region.

For example, if the TALEN binding sequence is -5' T-$N^{19}N^{14-20}N^{19}$-A3'

Then, the left TALEN sequence is -5'T-$N^{19}$-3' and the right TALEN sequence is the antisense strand sequence of -5'-$N^{19}$ A-3'.

Where N represents any nucleotide selected from A, G, T, C.

T represents nucleotide base Thymine in the target DNA sequence.

Thus, the amino acid sequence of the left and right TALEN constructs is represented as:
T-SEQ ID No.6
T-SEQ ID No.11
T-SEQ ID No.17
T-SEQ ID No.23
T-SEQ ID No.29
T-SEQ ID No.35
T-SEQ ID No.8
T-SEQ ID No.14
T-SEQ ID No.20
T-SEQ ID No.26
T-SEQ ID No.32
T-SEQ ID No.38

The functionality of FokI after dimerization allows stricter specificity at genomic location. Binding of both right and left TALEN at a specified location separated by 14-20 bp allows the FokI monomers to dimerize and become functional for double stranded break (DSB). Nonspecific binding of the TALEN at random locations does not create any DSB. Therefore, the off target effect of TAT EN constructs are minimal. This is one of the major advantages of the method of the present disclosure and is verified through analysis of large sequence data.

1.3—The complete process of obtains TALEN construct is composed of the following steps:
1. TALEN Designing.
2. Primer Designing.
3. Synthesis of Oligonucleotides.
4. Transformation of TALEN constructs (pcDNA3.1+TAL 6_Left and pcDNA3.1+TAL6_Right) on LB (Luria Broth)+ampicillin plate.
5. Inoculation of transformed cells (TALEN constructs) into LB with Ampicillin broth.
6. Isolation of Plasmid DNA pcDNA3.1+TAL6_Left and pcDNA3.1+TAL6_Right from DH10B or DH5alpha cells.
7. Transfection into CHOK1 cells; screening and selection by LCA assay.
8. Genomic DNA isolation of selected clones using QIAGEN DNeasy Blood & Tissue Kit.
9. Quantification by Spectrophotometry.
10. Optimization of PCR Condition.
11. Cross checking the Genomic DNA sample by PCR.
12. Electrophoresis on agarose gel.
13. PCR amplification using Phusion polymerase and tailing using Taq polymerase.
14. PCR product gel elution using QIAGEN kit.
15. TA cloning using pTZ57R/T vector.
16. Transformation of ligated sample pTZ57R/T+TAL (PCR) in DH10B or DH5alpha cells.
17. Inoculation of transformed cells (pTZ57R/T+TAL (PCR)) into LB with Ampicillin broth.
18. Isolation of plasmid DNA (pTZ57R/T+TAL(PCR) from DH5alpha and DH10B cells using QIAGEN plasmid DNA isolation kit.
19. Cross checking for the presence of insert by restriction digestion (Sites).
20. Sequencing primers; and
21. Confirmation of the INDELs by sequencing.

FIG. 1 of the present disclosure depicts the Fut8 coding sequence and protein sequence.

FUT8 genomic sequence is analyzed from database sequence, sequence ID NW_003613860. FUT8 genomic sequence spans from 570171-731804 bases and contains eleven exons depicted as E1 to E11 in FIG. 1. Base pairs locations for each exon are also indicated. E1, E2 and part of E3 constitute un-translated region in the upstream sequence, and part of E11 is also part of un-translated region. Translated regions are described as CDS 1 to CDS 9. Length of each CDS is indicated below the CDS number. CDS1 to CDS9 code for amino acid sequences varying from 38 amino acids to 105 amino acids. In FIG. 1, CDS7 indicated by black circle is targeted for amino acid modification through TALEN constructs. CDS7 corresponds to Exon 9 in the genomic locus.

*Cricetulus griseus* or Chinese Hamster fucosyltransferase 8 (Fut8)mRNA (3126 bp) is provided below. It is also represented by SEQ ID No. 40 of the present disclosure.

NCBI Reference Sequence: XM_003501735.1

CAGGTTGCTGCTCTGGCTTAGGCCATCTATGACCCTGGTGGTGTTTTCAT

TCACTATAAGTCCTTCCCATCTTTATTAACTGAGCAAGTTCAGctagtaa ttttagagaccgaggttcaagcaataacacctatctctgcaataccgtgt ggctttcttcaatgtcttacatcctaaggaaaggaagCATGTAGAGCCCA

GGAAGCACAGGACAAGAAAGCTGCCTCCTTGTATCACCAGGAAGATCTTT

TTGTAAGAGTCATCACAGTATACCAGAGAGACTAATTTTGTCTGAAGCAT

CATGTGTTGAAACAACAGAAACTTATTTTCCTGTGTGGCTAACTAGAACC

AGAGTACAATGTTTCCAATTCTTTGAGCTCCGAGAAGACAGAAGGGAGTT

GAAACTCTGAAAATGCGGGCATGGACTGGTTCCTGGCGTTGGATTATGCT

CATTCTTTTTGCCTGGGGGACCTTATTGTTTTATATAGGTGGTCATTTGG

TTCGAGATAATGACCACCCTGACCATTCTAGCAGAGAACTCTCCAAGATT

CTTGCAAAGCTGGAGCGCTTAAAACAACAAAATGAAGACTTGAGGAGAAT

GGCTGAGTCTCTCCGaataccagaaggccctattgatcaggggacagcta caggaagagtccgtgattagaagaacagcttgttaaggccaaagaacaga ttgaaaattacaagaaacaagctaggaatgATCTGGGAAAGGATCATGAA

ATCTTAAGGAGGAGGATTGAAAATGGAGCTAAAGAGCTCTGGTTTTTTCT

ACAAAGTGAATTGAAGAAATTAAAGAAATTAGAAGGAAACGAACTCCAAA

GACATGCAGATGAAATTCTTTTGGATTTAGGACATCATGAAAGgtctatc atgacagatctatactacctcagtcaaacagatggagcaggtgagtggcg ggaaaaagaagccaaagatctgacagagctggtccagcggagaataacat atctgcagAATCCCAAGGACTGCAGCAAAGCCAGAAAGCTGGTATGTAAT

ATCAACAAAGGCTGTGGCTATGGATGTCAACTCCATCATGTGGTTTACTG

CTTCATGATTGCTTATGGCACCCAGCGAACACTCATCTTGGAATCTCAGA

ATTGGCGCTATGCTACTGGAGGATGGGAGACTGTGTTTAGACCTGTAAGT

GAGACATGCACAGACAGGTCTGGCCTCTCCACTGGACACTGGTCAGgtga agtgaagga caaaaatgacaagtggtcgagctcccattgtagacagcctccatcctcg tcctccttacttaccatggctgtaccagaagaccttgcagatcgactcct gagagtccatggtgatcctgcagtgtggtgggtatcccagtagtcaaata cttgatccgtccacaaccaggctggaaagggaaatagaagaaaccaccaa gaagcaggcttcaaacatccagttattggAGTCCATGTCAGACGCACTGA

CAAAGTGGGAACAGAAGCAGCCTTCCATCCCATTGAGGAATACATGGTAC

ACGTTGAAGAACATTTTCAGCTTCTCGAACGCAGAATGAAAGTGGATAAA

AAAAGAGTGTATCTGGCCACTGATGACCCTTCTTTGTTAAAGGAGGCAAA

GACAAAgtactccaattatgaatttattagtgataactctatttcaggtc agctggactacacaaccgatacacagaaaattcacttcggggcgtgatcc tggatatacactactctcccaggctgacttccttgtgtgtacttatcatc ccagGTCTGTAGGGTTGCTTATGAAATCATGCAAACACTGCATCCTGATG

CCTCTGCAAACTTCCATTCTTTAGATGACATCTACTATTTTGGAGGCCAA

AATGCCCACAACCAGATTGCAGTTTATCCTCACCAACCTCGAACTAAAGA

GGAAATCCCCATGGAACCTGGAGATATCATTGGTGTGGCTGGAAACCATT

GGAATGGTTACTCTAAAGGTGTCAACAGAAAACTAGGAAAAACAGGCCTG

-continued
TACCCTTCCTACAAAGTCCGAGAGAAGATAGAAACAGTCAAATACCCTAC

ATATCCTGAAGCTGAAAAATAGAGATGGAGTGTAAGAGATTAACAACAGA

ATTTAGTTCAGACCATCTCAGCCAAGCAGAAGACCCAGACTAACATATGG

TTCATTGACAGACATGCTCCGCACCAAGAGCAAGTGGGAACCCTCAGATG

CTGCACTGGTGGAACGCCTCTTTGTGAAGGGCTGCTGTGCCCTCAAGCCC

ATGCACAGTAAAATAATGTACTCACACATAACATACAAATGGATTATTTT

CTACTTTGCCCTTTAAATATTCTGTCCCCATGAAACAAACACTGCCACAT

TATGTAATTTAAGTGACACAGACGTTTTGTGTGAGACTTCAAACATGGTG

CCTATATCTGAGAGACCTCTGTGATTTACTGAGAAGATGAGAACAGCTCC

CTTCTGTGGGGAAGTTGGTTCTTAGTCAGTGGTGGACTGGCCACTGAATT

CACTGCAATCAACAGATTCAGAATGAGAATGGATGTTTTTCCTTTATATG

GTTGTCTGGATTTTTTTTAAAGTAATTTCATCAGTTCAGTTCATCCACCT

CATTAATAAATGAAGGAATATACCAATAAAATCAAATGAAATATTCACTG

TCCATTAGGAAGTTTTATAAAACAATGCCATGAACAAAAAATTCTTTAGT

ACTCAATGTTTCTGGACATTCTCTTTGATAACAAAAATAAATTTTAAAAA

GGAATTTTGTAAAGTTTCTGGGATTCTGTATCACTGGATGATGTAGTTAT

AAGCTTTGTAGTAGAAATATGGGAAGTGGGTTTATAGCTTTTAAGATTTT

TTTCTACTTTTGTCCTACTTTTTCTATTTCTGATAGAATAATCATATTTC

AAGAGAAGCATTGGTCCCCTCTAATACTAGTAACTGCCTTTAGTCATGCA

TATTATATGAAGTTGCTAAGAACACGCTTTGGGGGAGGTGTTCACTCTCT

TAGTTTGATATTGTTGACTTGATATAATTGAATGAAATAGTCATTCTCTT

GCTTCCAG

Alternative exons are represented in upper and lower case letters

Amino acid residues at positions Arg 365, Arg 366, Asp-368, Lys-369, Glu-373, Tyr-382, Asp-409, Asp-410, Asp-453, and Ser-469 play important role in catalytic domain of FUT8 enzyme. Thus, in the method of the present disclosure, INDEL (insertion/deletion) mutations and frame shift mutations at amino acids positions Arg 365, Arg 366, Asp-368, Lys-369, and Glu-373 are introduced through TALEN to disrupt FUT8 enzyme function.

The TALEN design is aimed to primarily target amino acid positions Arg 365, Arg 366, Asp-368 Lys-369, and Giu-373 as these amino acids are critical for FUT8 enzyme functionality. The remaining four amino acid positions Tyr-382, Asp-409, Asp-410, Asp-453, and Ser-469 are downstream of the potential double strand break site between the two TALEN binding sequences. Any deletion or insertion or any other modification affects these amino acids and results in nonfunctional FUT8 enzyme. In an embodiment of the present disclosure, the subsequent genomic DNA analysis of the modified CHOK1 cell lines reveals deletion, insertion, stop codon as well as frame shift mutations. Thus, the present disclosure envisages disruption of Fut8 gene and Fucosyltransferase enzyme by targeting amino acid positions Arg 365, Arg 366, Asp-368, Lys-369, Glu-373, Tyr-382, Asp-409, Asp-410, Asp-453 and Ser-469 of the enzyme protein, directly or indirectly.

FIG. 2 of the present disclosure depicts the CHOK1 Fut8 amino-acid sequence. The amino acid positions disrupted by the method of the present disclosure are also depicted.

Complete amino acid sequence of FUT8 gene is provided. Amino acid sequence from each CDS is indicated with large arrowheads. Small arrows indicate critical amino acids present in CDS7 which are targeted in the Fut8 gene by TALEN constructs.

Exon-9 (CDS-7) DNA sequence is represented by SEQ ID No. 1 of the present disclosure.

Exon-9 (CDS-7) amino acid sequence of Fut8 of CHO cell is represented by SEQ ID No. 2 of the present disclosure. The targeted amino acid positions in the protein/peptide sequence are underlined.

VHVRRTDKVGTEAAFHPIEEYMVHVEEHFQLLERRMKVDKKRVYLATDDP

SLLKEAKT

The regions of the Fut8 gene targeted in the process in which the six designs are developed for TALEN constructs are provided below.

1.4—Sequence of Interest to be Targeted Using TALEN

TAL pair 1: TALEN 1L and 1R
cgaaagtacatagtgaaaccagaatattaaatagtgttcatctcctcaga cttcattgaaattcagtgtggcacattctccctgcctcacttcatagtat agaacacacggaacaagtccaatttcctgagagaaacagtgattaagagg aatgtaggaaagaaaagatgactgcatagttattcctgtggtcaaatcca caactggactatagtctgggatgcaaaggaaacagtagcatgaaggtggc acagttacccagtgtgctacagccctgactccagattcaagacataacc ctgtctttggcaacactaagatgcaggagagtgctgggaagtcagtgact tggccattgcaggtcagtgtaagtctgtattccttgctttataacattgt gacttttcttcaaaatgagaaatgaggtctgtttctgtttgcagttgat agagaaaaaaaatgcaaaaaaagtctgtagtaacttcatgaacataaaat aaccaacatctttaaaaggctagcttgtcttaaactacaggaaaagttca tatggatctttgttttcttagatgactttaaattctatgaactgaagtgg tagtaactttacagggtaaaatgaaagaaaaaaattaataaactttggca taagaatgttacaagcattatctttaagctttgaattctgttatgatttt ggtctcaaaaaccaaaaaacttaaatctgttgattccaggttcccatata ttcttggatatgccaattacttttctgtaagcaagtgtttcataaaact tttacttaactttcatattgacctgtactattcaacattcagctatgtta aagtatttgtgaagtgttttgaaatgattttatattttctaaggtgagaa taaatgagaaaatgttttaatatgtctccagtgcccccatgactagggat actaattgagtaccagtacattatcagtgtgctctccacttctccccagA

GTCCATGTCAGACGCACTGACAAAGTGGGAACAGAAGCAGCCTTCCATCC

CATTGAGGAATACATGGTACACGTTGAAGAACATTTTCAGCTTCTCGAAC

GCAGAATGAAAGTGGATAAAAAAAGAGTGTATCTGGCCACTGATGACCCT

TCTTTGTTAAAGGAGGCAAAGACAAAgtaagttagaccaacaagtggttc tgtatgggattatctcttagttgaagaaaatccttaattctgggaacttg tggttcttgttgctaactaataggttccaaaatcaaagactacatgtgca aatattaatctaatcaagtcatacctta ctagctgtatctgatgcaaatt

```
aagaagtctaaaatgaattagactgctgatttgtgtagcatcactagcag tcatcattcaacacagtaccacacttcttagtaccaaaatctgtttaaca tactagagtttccataaatcaaattttgtagcctggggcttaagtaacag aagtttatgtctcacagttttgatctgggatattccagatcgaggtccta gtgatattgattttactctgaagtttcttagcttacaggtagtcactat ccagtcatgatacactgtgttgttaaggaatttccattctggggatggaa cagaccattagtatatggtacacctagtactactgtggcattaggggaag cacatagacagactttgatgattcccccatgggaggcctcaccctccct gaggactggatgggggagtgagatgggagggttggtgaggggaatgggaa agtgggagggagagggaactgggattggtatgtaaataatatcattttaa tttaaataaaaattaatttaaaaagaaagaaagaagcacatagacaaagc cgtgagcaaaattggaaattctcagaagatctgggcgaataaaattaaaa gataaattatttatgaaatagaggaaggaagaaaaatttagtcttagctc attatactacctcctccaaaaatcatccctaagctttgagtaagtatccc tcctctacatattattggtgtatcattgaatacttgtgcacttctgtctc cttcagtacattttatatactttgatgagagtcctagctgtggtatagg cctagtaaatattgaattatttactt
```

Introns-1 base to 1000 base and 1178 base to 2177 base are represented in lower case. Exon 9-1001 base to 1177 bases is represented in upper case. Sequence of interest to be targeted in exon region is represented in bold letters, particularly AGA, CGC, GAC, AAA and GAA. The binding sites of Left and Right TALEN are underlined.

The present disclosure provides TALENs for deletion/mutation at any amino acid position of the Exon 9 region. The TALEN constructs of the present disclosure, in any combination of two or more TALEN proteins provide for specific mutation of the Exon 9 region of Fut8 gene.

This entire sequence of 2177 bases, made of Exon 9 and two surrounding introns of 1000 bases each, is represented by SEQ ID No. 3 of the present disclosure. The TALEN designs for TAL 2L/2R to TAL 6L/6R is also depicted using SEQ ID No. 3.

```
TAL pair 2: TAL2L and TAL 2R
cgaaagtacatagtgaaaccagaatattaaatagtgttcatctcctcaga cttcattgaaattcagtgtggcacattctccctgcctcacttcatttgta tagaacacacggaacaagtccaatttcctgagagaaacagtgattaagag gaatgtaggaaagaaaagatgactgcatagttattcctgtggtcaaatcc acaactggactatagtctgggatgcaaaggaaacagtagcatgaaggtgg cacagttacccccagtgtgctacagccctgactccagattcaagacataac cctgtctttggcaacactaagatgcaggagagtgctgggaagtcagtgac ttggccattgcaggtcagtgtaagtctgtattccttgctttataacattg tgacttttcttcaaaatgagaaaatgaggtctgtttctgtttgcagttga tagagaaaaaaatgcaaaaaaagtctgtagtaacttcatgaacataaaa taaccaacatctttaaaaggctagcttgtcttaaactacaggaaaagttc atatggatctttgttttcttagatgactttaaattctatgaactgaagtg gtagtaactttacagggtaaaatgaaagaaaaaaattaataaactttggc ataagaatgttacaagcattatctttaagctttgaattctgttatgattt tggtctcaaaaaccaaaaaacttaaatctgttgattccaggttcccatat attcttggatatgccaattacttttctgtaagcaagtgtttcataaaac ttttacttaactttcatattgacctgtactattcaacattcagctatgtt aaagtatttgtgaagtgttttgaaatgattttatattttctaaggtgaga ataaatgagaaaatgttttaatatgtctccagtgcccccatgactaggga tactaattgagtaccagtacattatcagtgtgctctccacttctccccag

AGTCCATGTCAGACGCACTGACAAAGTGGGAACAGAAGCAGCCTTCCATC

CCATTGAGGAATACATGGTACACGTTGAAGAACATTTTCAGCTTCTCGAA

CGCAGAATGAAAGTGGATAAAAAAAGAGTGTATCTGGCCACTGATGACCC

TTCTTTGTTAAAGGAGGCAAAGACAAAgtaagttagaccaacaagtggac tgtatgggattatctcttagttgaagaaaatccttaattctgggaacttg tggttcttgttgctaactaataggttccaaaatcaaagactacatgtgca aatattaatctaatcaagtcataccttactagctgtatctgatgcaaatt aagaagtctaaaatgaattagactgctgatttgtgtagcatcactagcag tcatcattcaacacagtaccacacttcttagtaccaaaatctgtttaaca tactagagtttccataaatcaaattttgtagcctggggcttaagtaacag aagtttatgtctcacagttttgatctgggatattccagatcgaggtccta gtgatattgattttactctgaagtttcttagcttacaggtagtcactat ccagtcatgatacactgtgttgttaaggaatttccattctggggatggaa cagaccattagtatatggtacacctagtactactgtggcattaggggaag cacatagacagactttgatgattcccccatgggaggcctcaccctccct gaggactggatgggggagtgagatgggagggttggtgaggggaatgggaa agtgggagggagagggaactgggattggtatgtaaataatatcattttaa tttaaataaaaattaatttaaaaagaaagaaagaagcacatagacaaagc cgtgagcaaaattggaaattctcagaagatctgggcgaataaaattaaaa gataaattatttatgaaatagaggaaggaagaaaaatttagtcttagctc attatactacctcctccaaaaatcatccctaagctttgagtaagtatccc tcctctacatattattggtgtatcattgaatacttgtgcacttctgtctc cttcagtacattttatatactttgatgagagtcctagctgtggtatagg cctagtaaatattgaattatttactt
```

Introns-1 base to 1000 base and 1178 base to 2177 base is represented in lower case. Exon 9-1001 base to 1177 base is represented in upper case. Sequence of interest to be targeted in exon regions is represented in bold letters, particularly AGA, CGC, GAC, AAA and GAA. The binding sites of Left and Right TALEN are underlined.

```
TAL pair 3: TAL3L and TAL 3R
cgaaagtacatagtgaaaccagaatattaaatagtgttcatctcctcaga cttcattgaaattcagtgtggcacattctccctgcctcacttcatttgta tagaacacacggaacaagtccaatttcctgagagaaacagtgattaagag
``` gaatgtaggaaagaaaagatgactgcatagttattcctgtggtcaaatcc acaactggactatagtctgggatgcaaaggaaacagtagcatgaaggtgg cacagttacccagtgtgctacagccctgactccagattcaagacataac cctgtctttggcaacactaagatgcaggagagtgctgggaagtcagtgac ttggccattgcaggtcagtgtaagtctgtattccttgctttataacattg tgacttttcttcaaaatgagaaaatgaggtctgtttctgtttgcagttga tagagaaaaaaatgcaaaaaagtctgtagtaacttcatgaacataaaa taaccaacatctttaaaaggctagcttgtcttaaactacaggaaaagttc atatggatctttgttttcttagatgactttaaattctatgaactgaagtg gtagtaactttacagggtaaaatgaaagaaaaaaattaataaactttggc ataagaatgttacaagcattatctttaagctttgaattctgttatgattt tggtctcaaaaaccaaaaaacttaaatctgttgattccaggttcccatat attcttggatatgccaattacttttctgtaagcaagtgtttcataaaac ttttacttaactttcatattgacctgtactattcaacattcagctatgtt aaagtatttgtgaagtgttttgaaatgattttatattttctaaggtgaga ataaatgagaaatgttttaatatgtctccagtgccccatgactaggga tactaattgagtaccagtacattatcagtgtgctctccacttctcccag

AGTCCATGTCAGACGCACTGACAAAGTGGGAACAGAAGCAGCCTTCCATC

CCATTGAGGAATACATGGTACACGTTGAAGAACATTTTCAGCTTCTCGAA

CGCAGAATGAAAGTGGATAAAAAAAGAGTGTATCTGGCCACTGATGACCC

TTCTTTGTTAAAGGAGGCAAAGACAAAgtaagttagaccaacaagtggac tgtatggattatctcttagttgaagaaaatccttaattctgggaacttg tggttcttgttgctaactaataggttccaaaatcaaagactacatgtgca aatattaatctaatcaagtcataccttactagctgtatctgatgcaaatt aagaagtctaaaatgaattagactgctgatttgtgtagcatcactagcag tcatcattcaacacagtaccacacttcttagtaccaaaatctgtttaaca tactagagtttccataaatcaaatttttgtagcctggggcttaagtaacag aagtttatgtctcacagttttgatctgggatattccagatcgaggtccta gtgatattgattttactctgaagtttcttagcttacaggtagtcactat ccagtcatgatacactgtgttgttaaggaatttccattctggggatggaa cagaccattagtatatggtacacctagtactactgtggcattaggggaag cacatagacagactttgatgattcccccatgggaggcctcaccctcct gaggactggatgggggagtgagatgggagggttggtgaggggaatgggaa agtgggaggagagggaactgggattggtatgtaaataatatcattttaa tttaaataaaaattaatttaaaagaaagaaagaagcacatagacaaagc cgtgagcaaaattggaaattctcagaagatctgggcgaataaaattaaaa gataaattatttatgaaatagaggaaggaagaaaaatttagtcttagctc attatactacctcctccaaaaatcatccctaagctttgagtaagtatccc tcctctacatattattggtgtatcattgaatacttgtgcacttctgtctc cttcagtacattttatatacttttgatgagagtcctagctgtggtatagg cctagtaaatattgaattatttactt Introns-1 base to 1000 base and 1178 base to 2177 base is represented in lower case. Exon 9-1001 base to 1177 base is represented in upper case. Sequence of interest to be targeted in exon region 9 is in bold letters, particularly AGA, CGC, GAC, AAA and GAA. The binding sites of Left and Right TALEN are underlined.

TAL pair 4: TAL4L and TAL 4R
cgaaagtacatagtgaaaccagaatattaaatagtgttcatctcctcaga cttcattgaaattcagtgtggcacattctccctgcctcacttcatttgta tagaacacacggaacaagtccaatttcctgagagaaacagtgattaagag gaatgtaggaaagaaaagatgactgcatagttattcctgtggtcaaatcc acaactggactatagtctgggatgcaaaggaaacagtagcatgaaggtgg cacagttacccagtgtgctacagccctgactccagattcaagacataac cctgtctttggcaacactaagatgcaggagagtgctgggaagtcagtgac ttggccattgcaggtcagtgtaagtctgtattccttgctttataacattg tgacttttcttcaaaatgagaaaatgaggtctgtttctgtttgcagttga tagagaaaaaaatgcaaaaaagtctgtagtaacttcatgaacataaaa taaccaacatctttaaaaggctagcttgtcttaaactacaggaaaagttc atatggatctttgttttcttagatgactttaaattctatgaactgaagtg gtagtaactttacagggtaaaatgaaagaaaaaaattaataaactttggc ataagaatgttacaagcattatctttaagctttgaattctgttatgattt tggtctcaaaaaccaaaaaacttaaatctgttgattccaggttcccatat attcttggatatgccaattacttttctgtaagcaagtgtttcataaaac ttttacttaactttcatattgacctgtactattcaacattcagctatgtt aaagtatttgtgaagtgttttgaaatgattttatattttctaaggtgaga ataaatgagaaatgttttaatatgtctccagtgccccatgactaggga tactaattgagtaccagtacattatcagtgtgctctccacttctcccag

AGTCCATGTCAGACGCACTGACAAAGTGGGAACAGAAGCAGCCTTCCATC

CCATTGAGGAATACATGGTACACGTTGAAGAACATTTTCAGCTTCTCGAA

CGCAGAATGAAAGTGGATAAAAAAAGAGTGTATCTGGCCACTGATGACCC

TTCTTTGTTAAAGGAGGCAAAGACAAAgtaagttagaccaacaagtggac tgtatggattatctcttagttgaagaaaatccttaattctgggaacttg tggttcttgttgctaactaataggttccaaaatcaaagactacatgtgca aatattaatctaatcaagtcataccttactagctgtatctgatgcaaatt aagaagtctaaaatgaattagactgctgatttgtgtagcatcactagcag tcatcattcaacacagtaccacacttcttagtaccaaaatctgtttaaca tactagagtttccataaatcaaatttttgtagcctggggcttaagtaacag aagtttatgtctcacagttttgatctgggatattccagatcgaggtccta gtgatattgattttactctgaagtttcttagcttacaggtagtcactat -continued
ccagtcatgatacactgtgttgttaaggaatttccattctggggatggaa cagaccattagtatatggtacacctagtactactgtggcattaggggaag cacatagacagactttgatgattcccccatgggaggcctcaccctccct gaggactggatgggggagtgagatgggagggttggtgaggggaatgggaa agtgggagggagagggaactgggattggtatgtaaataatatcattttaa tttaaataaaaattaatttaaaaagaaagaaagaagcacatagacaaagc cgtgagcaaaattggaaattctcagaagatctgggcgaataaaattaaaa gataaattatttatgaaatagaggaaggaagaaaaatttagtcttagctc attatactacctcctccaaaaatcatccctaagctttgagtaagtatccc tcctctacatattattggtgtatcattgaatacttgtgcacttctgtctc cttcagtacattttatatacttttgatgagagtcctagctgtggtatagg cctagtaaatattgaattatttactt Introns-1 base to 1000 base and 1178 base to 2177 base are represented in lower case. Exon 9-1001 base to 1177 base are represented in upper case. The binding sites of Left and Right TALEN are underlined. The sequence of interest to be targeted in exon region 9 is particularly AGA, CGC, GAC, AAA and GAA.

TAL pair 5: TAL5L and TAL 5R
cgaaagtacatagtgaaaccagaatattaaatagtgttcatctcctcaga cttcattgaaattcagtgtggcacattctccctgcctcacttcatttgta tagaacacacggaacaagtccaatttcctgagagaaacagtgattaagag gaatgtaggaaagaaaagatgactgcatagttattcctgtggtcaaatcc acaactggactatagtctgggatgcaaaggaaacagtagcatgaaggtgg cacagttacccagtgtgctacagccctgactccagattcaagacataac cctgtctttggcaacactaagatgcaggagagtgctgggaagtcagtgac ttggccattgcaggtcagtgtaagtctgtattccttgctttataacattg tgacttttcttcaaaatgagaaatgaggtctgtttctgtttgcagttga tagagaaaaaaatgcaaaaaagtctgtagtaacttcatgaacataaaa taaccaacatctttaaaaggctagcttgtcttaaactacaggaaaagttc atatggatctttgttttcttagatgactttaaattctatgaactgaagtg gtagtaactttacagggtaaaatgaaagaaaaaaattaataaactttggc ataagaatgttacaagcattatctttaagctttgaattctgttatgattt tggtctcaaaaaccaaaaaacttaaatctgttgattccaggttcccatat attcttggatatgccaattacttttttctgtaagcaagtgtttcataaaac ttttacttaactttcatattgacctgtactattcaacattcagctatgtt aaagtatttgtgaagtgttttgaaatgattttatattttctaaggtgaga ataaatgagaaatgttttaatatgtctccagtgccccatgactaggga tactaattgagtaccagtacattatcagtgtgctctccacttctccccag

AGTCCATGTCAGACGCACTGACAAAGTGGGAACAGAAGCAGCCTTCCATC

CCATTGAGGAATACATGGTACACGTTGAAGAACATTTTCAGCTTCTCGAA

CGCAGAATGAAAGTGGATAAAAAAAGAGTGTATCTGGCCACTGATGACCC

-continued
TTCTTTGTTAAAGGAGGCAAAGACAAAGtaagttagaccaacaagtggac tgtatgggattatctcttagttgaagaaaatccttaattctgggaacttg tggttcttgttgctaactaataggttccaaaatcaaagactacatgtgca aatattaatctaatcaagtcataccttactagctgtatctgatgcaaatt aagaagtctaaaatgaattagactgctgatttgtgtagcatcactagcag tcatcattcaacacagtaccacacttcttagtaccaaaatctgtttaaca tactagagtttccataaatcaaattttgtagcctggggcttaagtaacag aagtttatgtctcacagttttgatctgggatattccagatcgaggtccta gtgatattgattttttactctgaagtttcttagcttacaggtagtcactat ccagtcatgatacactgtgttgttaaggaatttccattctggggatggaa cagaccattagtatatggtacacctagtactactgtggcattaggggaag cacatagacagactttgatgattcccccatgggaggcctcaccctccct gaggactggatgggggagtgagatgggagggttggtgaggggaatgggaa agtgggagggagagggaactgggattggtatgtaaataatatcattttaa tttaaataaaaattaatttaaaaagaaagaaagaagcacatagacaaagc cgtgagcaaaattggaaattctcagaagatctgggcgaataaaattaaaa gataaattatttatgaaatagaggaaggaagaaaaatttagtcttagctc attatactacctcctccaaaaatcatccctaagctttgagtaagtatccc tcctctacatattattggtgtatcattgaatacttgtgcacttctgtctc cttcagtacattttatatacttttgatgagagtcctagctgtggtatagg cctagtaaatattgaattatttactt Intron-1 base to 1000 base and 1178 base to 2177 base is represented in lower case. Exon 9-1001 base to 1177 base is represented in upper case. The binding sites of Left and Right TALEN are underlined. The sequence of interest to be targeted in exon region 9 is particularly AGA, CGC, GAC, AAA and GAA.

Tal pair 6: TAL6L and TAL 6R
cgaaagtacatagtgaaaccagaatattaaatagtgttcatctcctcaga cttcattgaaattcagtgtggcacattctccctgcctcacttcatttgta tagaacacacggaacaagtccaatttcctgagagaaacagtgattaagag gaatgtaggaaagaaaagatgactgcatagttattcctgtggtcaaatcc acaactggactatagtctgggatgcaaaggaaacagtagcatgaaggtgg cacagttacccagtgtgctacagccctgactccagattcaagacataac cctgtctttggcaacactaagatgcaggagagtgctgggaagtcagtgac ttggccattgcaggtcagtgtaagtctgtattccttgctttataacattg tgacttttcttcaaaatgagaaatgaggtctgtttctgtttgcagttga tagagaaaaaaatgcaaaaaagtctgtagtaacttcatgaacataaaa taaccaacatctttaaaaggctagcttgtcttaaactacaggaaaagttc atatggatctttgttttcttagatgactttaaattctatgaactgaagtg gtagtaactttacagggtaaaatgaaagaaaaaaattaataaactttggc ataagaatgttacaagcattatctttaagctttgaattctgttatgattt -continued
```
tggtctcaaaaaccaaaaaacttaaatctgttgattccaggttcccatat attcttggatatgccaattacttttctgtaagcaagtgtttcataaaac ttttacttaactttcatattgacctgtactattcaacattcagctatgtt aaagtatttgtgaagtgttttgaaatgattttatattttctaaggtgaga ataaatgagaaaatgttttaatatgtctccagtgccccatgactaggga tactaattgagtaccagtacattatcagtgtgctctccacttctccccag

AGTCCATGTCAGACGCACTGACAAAGTGGGAACAGAAGCAGCCTTCCATC

CCATTGAGGAATACATGGTACACGTTGAAGAACATTTTCAGCTTCTCGAA

CGCAGAATGAAAGTGGATAAAAAAAGAGTGTATCTGGCCACTGATGACCC

TTCTTTGTTAAAGGAGGCAAAGACAAAGtaagttagaccaacaagtggac tgtatgggattatctcttagttgaagaaaatccttaattctgggaacttg tggttcttgttgctaactaataggttccaaaatcaaagactacatgtgca aatattaatctaatcaagtcataccttactagctgtatctgatgcaaatt aagaagtctaaaatgaattagactgctgatttgtgtagcatcactagcag tcatcattcaacacagtaccacacttcttagtaccaaaatctgtttaaca tactagagtttccataaatcaaattttgtagcctggggcttaagtaacag aagtttatgtctcacagttttgatctgggatattccagatcgaggtccta gtgatattgattttttactctgaagtttcttagcttacaggtagtcactat ccagtcatgatacactgtgttgttaaggaatttccattctgggatggaa cagaccattagtatatggtacacctagtactactgtggcattaggggaag cacatagacagactttgatgattcccccatgggaggcctcaccctccct gaggactggatggggagtgagatgggagggttggtgaggggaatgggaa agtgggagggagagggaactgggattggtatgtaaataatatcattttaa tttaaataaaaattaatttaaaaagaaagaaagaagcacatagacaaagc cgtgagcaaaattggaaattctcagaagatctgggcgaataaaattaaaa gataaattatttatgaaatagaggaaggaagaaaaatttagtcttagctc attatactacctcctccaaaaatcatccctaagctttgagtaagtatccc tcctctacatattattggtgtatcattgaatacttgtgcacttctgtctc cttcagtacattttatatactttgatgagagtcctagctgtggtatagg cctagtaaatattgaattatttactt
```

Introns-1 base to 1000 base and 1178 to 2177 base is represented in lower case. Exon 9-1001 base to 1177 base is represented in upper case. The binding sites of Left and Right TALEN are underlined. Sequence of interest to be targeted in exon region in bold letters, particularly AGA, CGC, GAC, AAA and GAA.

FUT8 genomic sequence study reveals the intron and exon sequence around exon 9. Exon9 is a small exon spanning over 177 bp which contains all seven critical amino acid positions required for FUT8 enzyme function. This exon codes for critical catalytic domain of the enzyme. The exon 9 sequence allows only few TALEN DNA binding domain designs which suitably flank the target amino acid positions.

Designs 1 to 6 are the best possible designs in exon 9 sequence. Among these designs TAL1 is upstream of the targeted amino acid positions while designs TAL2 and TAL3 are downstream of the targeted amino acids. The method of the present disclosure creates two DNA binding domains flanking all or maximum or most important target amino acid positions.

All the TALEN pair constructs TAL1L-1R to TAL6L-6R are analyzed for disruption of Fut8 gene and depict successful disruption of Fut8 gene and resulting enzyme activity.

Among these, TALE is selected for further studies as an exemplification as it targets the most studied mutations in the FUT 8 enzyme functionality, positions Arg 365, Arg 366, Asp-368, Lys-369, Glu-373.

However, it is to be noted that all the TAL pairs provided in the present disclosure, i.e. TAL 1 to TAL 6, provide for efficient disruption of the Fut8 gene in the present disclosure.

TAL pair 6: TALEN Binding site
TGTGCTC<u>TCCACTTCTCCCCAGAGTC</u>CATGTC*AGACGCACTGAC*AAAGTG GGAACAGAAGCAGCCTTCCATCC In the gene sequence of Fut8 provided above, the Left TALEN binding site is underlined and represented as SEQ ID No. 4 and the Right TALEN binding site is in bold and represented as SEQ ID No. 5. The TALEN constructs are designed to recognize the afore-mentioned sequences. In italics are the nucleotides coding for the region to be mutated by the method of the present disclosure.

1.5—TALEN Synthesis from GeneArt

Construct-pcDNA3.1-TALEN_L6 is represented by FIG. 3 of the present disclosure.

Figure 4:
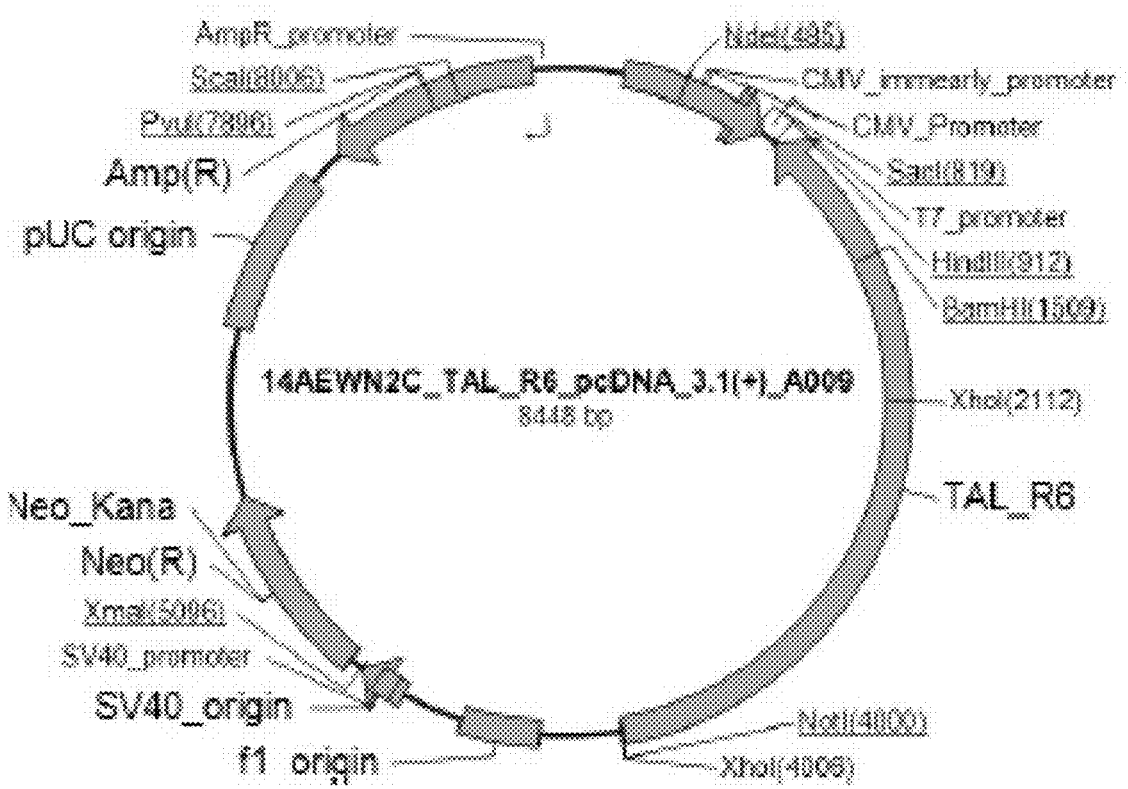
FIG. 4 depicts Construct pcDNA3.1-TALEN_R6.

Construct pcDNA3.1-TALEN_R6 is represented by FIG. 4 of the present disclosure.

The TALEN constructs consist of two parts, DNA binding domain and Nuclease domain. The DNA binding domain also has 2 domains—the TAL domain that identifies sequence left to the double strand break (DSB) target is termed as TAL-L and the TAL domain that identifies sequence right to the DSB target is termed as TAL-R. Both TAL-L and TAL-R domains are expressed as fusion protein with Fok1 nuclease domain.

In this example, the construction of TAL-L6 and TAL-R6 is explained. However, the data is provided for exemplification and is applicable to other TAL Pairs.

Construction of TAL-L6 Constructs:

The synthetic TAL-L6 is assembled from synthetic oligonucleotides and/or PCR products. The fragment is cloned into TALtrunc_FokI using 100% sequence verified sub-fragments. The resulting plasmid DNA is purified from transformed bacteria and quantified by UV spectroscopy. The final construct is confirmed by sequencing.

The TAL-L6 binding sequence for TALEN 6 design is 5' TCCACTTCTCCCCAGAGTC 3' corresponding to RVD (T)-HD-HD-NI-HD-NG-NG-HD-NG-HD-HD-HD-HD-NI-NN-NI-NN-NG-HD, where '(T)' indicates that the first binding repeat is provided by the vector.

FIG. 3 describes the TAL-L6 DNA cloned in pcDNA3.1 vector backbone for eukaryotic expression. The TALEN constructs are designed in two parts. The construct described in FIG. 3 identifies genomic DNA sequence left to the double strand break (DSB) target and is termed as TAL-L6. The synthetic gene TAL_L6 is assembled from synthetic oligonucleotides and/or PCR products. The fragment is cloned into TALtrunc_FokI using 100% sequence verified sub-fragments. The complete TAL-L6 sequence reading frame including the Kozak sequence is cloned under restriction sites NotI and HindIII. The plasmid DNA is purified from transformed bacteria and concentration determined by UV spectroscopy. The final construct is verified by sequencing. The sequence congruence within the used restriction sites is 100%. The TAL_L6 cassette is cloned in pcDNA3.1 (+)A009 with CMV promoter. The construct contains neomycin resistance gene for eukaryotic selection.

TAL-L6 Amino Acid Sequence

Amino acid sequence of the RVD—(T)-HD-HD-NI-HD-NG-NG-HD-NG-HD-HD-HD-HD-NI-NN-NI-NN-NG-HD. It is also provided in SEQ ID No. 6 of the present disclosure.

TAL-L6 sequence (nucleotide sequence) is represented by SEQ ID No. 7 of the present disclosure.

Construction of TAL-R6 Constructs:

The synthetic TAL-R6 is assembled from synthetic oligonucleotides and/or PCR products. The fragment is cloned into TALtrunc_FokI using 100% sequence verified sub-fragments. The resulting plasmid DNA is purified from transformed bacteria and quantified by UV spectroscopy. The final construct is confirmed by sequencing.

The TAL-R6 binding sequence is 5'-TGCTTCTGTTC-CCACTTTG-3' corresponding to RVD (T)-NN-HD-NG-NG-HD-NG-NN-NG-NG-HD-HD-HD-NI-HD-NG-NG-NG-NN, where '(T)' indicates that the first binding repeat is provided by the vector.

FIG. 4 describes the TAL-R6 DNA cloned in pcDNA3.1 vector backbone for eukaryotic expression. The TALEN constructs are designed in two parts. The construct described in FIG. 4 identifies genomic DNA sequence right to the double strand break (DSB) target and is termed as TAL-R6. The synthetic gene TAL-R6 is assembled from synthetic oligonucleotides and/or PCR products. The fragment is cloned into TALtrunc_FokI using 100% sequence verified sub-fragments. The complete TAL-R6 sequence reading frame including the Kozak sequence is cloned under restriction sites NotI and HindIII. The complete cassette is represented as TAL_R6 fragment with NotI and HindIII flanking restriction enzymes. The plasmid DNA is purified from transformed bacteria and concentration determined by UV spectroscopy. The final construct is verified by sequencing. The sequence congruence within the used restriction sites is 100%. The TAL_R6 cassette is cloned in pcDNA3.1 (+)_A009 with CMV promoter. The construct contains neomycin resistance gene for eukaryotic selection.

TAL-R6 amino acid sequence is represented by SEQ ID No. 8 of the present disclosure.

Amino acid sequence of the RVD: (T)-NN-HD-NG-NG-HD-NG-NN-NG-NG-HD-HD-HD-NI-HD-NG-NG-NG-NN TAL-R6 nucleotide sequence is represented by SEQ ID No. 9 of the present disclosure.

Construct-pcDNA3.1-TALEN_L6 is represented by FIG. 3 of the present disclosure.

Construct pcDNA3.1-TALEN_R6 is represented by FIG. 4 of the present disclosure.

EXAMPLE 2

Transfection of Cells with Talen Constructs

This example contains procedure for CHOK1 cell transfection with TALEN constructs. It also provides for selection and confirmation of single cell stable cell lines for developing FUT8 knock out CHOK1 cell line using TALEN technology, and selection of positive clones by flowcytometry based functional assay.

Transfection Protocol

Transfection is optimized using CHOK1 cells, both adherent and suspension type. Liposome and modified liposome mediated transfection reagents are tested for e.g., Lipofectamine 2000, Lipofectamine 3000, Lipofectamine LTX with Plus™ reagent, MIRUS TransIT X2, MIRUS TransIT 2020, MIRUS TransIT 293, MIRUS TransIT CHOK1 transfection kit. DNA concentration ranging from 0.5 µg to 5 µg are tested for various incubation times for e.g., 4 hrs, 24 hrs and 48 hrs. Multiple DNA to transfection reagent ratios (µg: µl) are also tested. The optimum transfection efficiency is achieved using 1:5 DNA to transfection reagent ratio, 24 hrs incubation and Lipofectamine LTX with Plus™ reagent. Optimization experiments are performed with Red Fluorescence Protein (RFP) expressing plasmid DNA.

Figure 25:
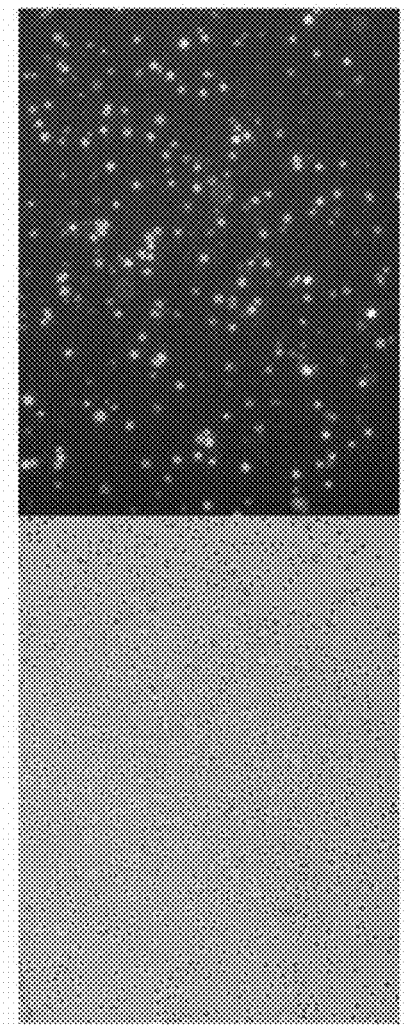
FIG. 25 depicts the pictorial representation of the RFP expressing cells after the Transfection protocol.

FIG. 25 depicts transfection efficiency of CHOK1 cell line using the protocol described in the disclosure. Transfection efficiency is determined using a Red Fluorescent Protein expressing plasmid construct. Number of red cells observed after transfection compared to the total number of viable cells determines transfection efficiency of the protocol established. Panel A represents the bright field image and panel B represents the same microscopic field for red channel fluorescence.

Transfection efficiency is calculated by the following formula:

Transfection efficiency=(Number of RFP expressing cells/Total number of cells)*100

Optimized transient transfection efficiency is about 40-50% in CHOK1 cells. The optimized transfection process is used for all TALEN construct transfection into CHOK1 cells in the following examples.

TALEN Transfection of CHOK1 Cells:

2.1 Transfection:

CHOK1 cells are seeded at more than 90% viability and a density of $0.25 \times 10^6$ cells/well in a 6 well tissue culture plate and allowed to adhere for 4 hrs. pcDNA3.1-TALEN_L6 and pcDNA3.1-TALEN_R6 constructs are transfected using Lipofectamine LTX with Plus™ reagent. 2.5 µg of each DNA construct is used with 1:5 DNA to transfection reagent ratio. The cells are incubated for 20-24 hrs after transfection. Prior to transfection, DNA quantity and quality is estimated by UV spectrophotometry. $A_{260/280}$ value DNA represents quality and protein contamination. The ratio of absorbance at 260 nm and 280 nm is used to assess the purity of DNA. $A_{260/280} > 1.8$ is generally accepted as "pure" or good quality DNA. 3-4 µl of DNA sample is placed on the micro cuvette and DNA concentration is estimated using Eppendorf Biophotometer D30 against suitable blank.

TALEN DNA Dilution:

| For n wells | 2.5 µg * n |
|---|---|
| pcDNA3.1-TALEN_L6 | 2.5 µg * n |
| pcDNA3.1-TALEN_R6 | 2.5 µg * n |
| Plus ™ reagent | 1.33 * 2 µl |
| Media without serum | Up to 1 ml * n |

Lipofectamine LTX Dilution:

| Lipofectamine LTX | 25 µl * n |
|---|---|
| Media without serum | Up to 0.5 ml * n |

Media change is provided to the cells with serum free media, 1 hour prior to transfection, TALEN constructs and Lipofectamine LTX solution are diluted, mixed gently and incubated for 10 minutes at 20-25° C. DNA and transfection reagent dilutions (3 ml) are mixed and incubated for 30 minutes at 20° C. to 25° C. for complex formation. The media is aspirated from the wells. 1.5 ml of DNA and transfection reagent complex is added drop wise to the plated cells. The cells are incubated for 4 hours at 37° C. in a 5% $CO_2$ Incubator. The complete media is added at 1.5 ml/well and incubated for 20-24 hours at 37° C. in a 5% $CO_2$ Incubator. After 20-24 hours of transfection, cells are trypsinized and followed by single cell dilution.

Single cell dilution is obtained by serial dilution of the cells to a concentration of 0.5 cell/100 µl. Cell count is taken using hemocytometer. After process optimization the CHOK1 cells are seeded at a density of 0.5 cells/100 µl/well and show good yield of single cell colonies. The cells are allowed to grow for few days at 37° C. in a 5% $CO_2$ Incubator. Plate scanning is done to identify single cell colonies under the inverted phase contrast microscope. Cells growing into distinctly small single colonies are marked for further amplification. After 2-3 weeks, single cell clones are amplified from one well of 96 well plate to one well of 6 well plate by trypsinization. Cells are allowed to grow for 2-3 days at 37° C. at 5% $CO_2$ in a $CO_2$ incubator. Cells are further amplified from one well to two wells in a 24 well plate (replica plating) for further screening.

2.2—LCA (Lens Culinaris Agglutin) Assay—Set 1

This is a functional assay to screen clones with afucosylated membrane proteins. Fucosylation is an integral biochemical process for many cellular proteins, and many of those are membrane proteins. Lens Culinaris Agglutinin (LCA) is a lectin which binds any fucosylated protein preferentially.

For cells that express a fucosylated membrane protein, LCA gets recognized and internalized and acts as a cytotoxic agent. As a result, cells with fucosylated membrane proteins get rounded off and eventually die depending on LCA concentration. On the other hand, cells with non-fucosylated membrane proteins survive and maintain colony morphology even in presence of high concentration of LCA. Based on this property, cells are quickly categorized into FUT8 knock out or wild type phenotype. LCA kill curve optimization is performed and 200 µg/ml of LCA reagent is used for LCA based selection. After replica plating, one set is retained as master plate and 200 µg/ml LCA is added to the clones in replica plate. 50 clones are tested for LCA resistance. Daily microscopic observation is done and clones maintaining colony morphology are identified and tested for further confirmation of FUT8 knockout cells.

2.3 LCA-FITC (Lens Culinaris Agglutin-Fluorescein Isothiocyanate) Binding Assay

Fluorescein iso thio-cyanate (FITC) is a fluorochrome conjugated to LCA. Therefore, presence of fucosylated proteins on cell membrane of control CHOK1 cells is recognized by fluorescein conjugated LCA. These cells fluoresce brighter in specific flow cytometer channel. The fluorescence observed is represented as Relative fluorescence unit (RFU). The cells where fucose pathway is disrupted, the cell lines are not able to produce fucosylated cellular proteins and hence the cell membrane proteins are non fucosylated. Testing these cells with Fluorescein-LCA conjugate results in fluorescence comparable to background. Therefore, the Fucose knock out cells fluoresce at a much lower level (less than 100RFU) compared to control CHOK1 cell line.

Transfected CHOK1 cells and untransfected control CHOK1 cells are trypsinized, transferred to a microfuge tube and spun at 1500 rpm (revolution per minute) for 5 minutes using Eppendorf minispin centrifuge. The media is removed and fresh media is added in the tubes. Both transfected and Untransfected CHOK1 cells are processed simultaneously. The cells are tested for LCA-FITC flow cytometry based analysis using "Millipore GUAVA 8 easyCyte HT" benchtop flow cytometer. 4 clones are screened for Fut8 knockout profile—TAL R4 #003, TAL R4 #013, TAL R4 #023 and TAL R4 #024.

Fluorescein Lens Culinaris Agglutinin (LCA-FITC) stock 5 mg/ml is diluted to get 2 µg/ml final concentration in assay buffer (DPBS containing 2% BSA). Cells are spun at 1500 rpm for 5 minutes using Eppendorf minispin centrifuge. The media is aspirated and the pellet is re-suspended in 0.25-1 ml of assay buffer containing 2 µg/ml LCA-FITC. CHOK1 control cells are re-suspended in 0.25-1 ml of assay buffer alone (unstained control) and 0.25-1 ml of assay buffer containing 2 µg/ml LCA-FITC (stained control). All samples are diluted to get $0.1$-$0.2 \times 10^6$ cells/ml in final assay buffer. The samples are then incubated in dark on ice for 30 minutes. Then 200 µl of each sample is aliquoted in a 96 well plate. The plate is then loaded in the Millipore GUAVA easyCyte 8HT bench-top flow cytometer for data acquisition and analysis. Data analysis is done using Incyte software.

TABLE 5

| | Results Set 1 | |
|---|---|---|
| Sl. No. | Sample ID | Median RFU |
| 1 | Unstained control | 8.77 |
| 2 | Stained control | 984.17 |
| 3 | TAL R4 #003 | 556.78 |
| 4 | TAL R4 #013 | 18.08 |
| 5 | TAL R4 #023 | 20.34 |
| 6 | TAL R4 #024 | 26.81 |

Median RFU refers to median value of relative fluorescence unit.

Figure 5:
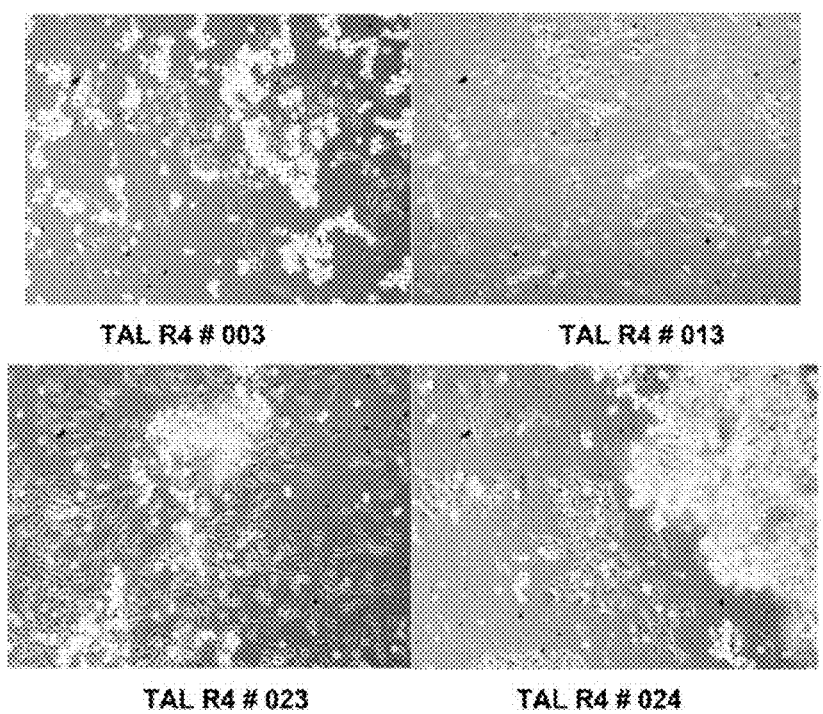
FIGS. 5 and 6 depict the pictures of the LCA-selected CHOK1 clones on Day 1 and Day 11.
Figure 6:
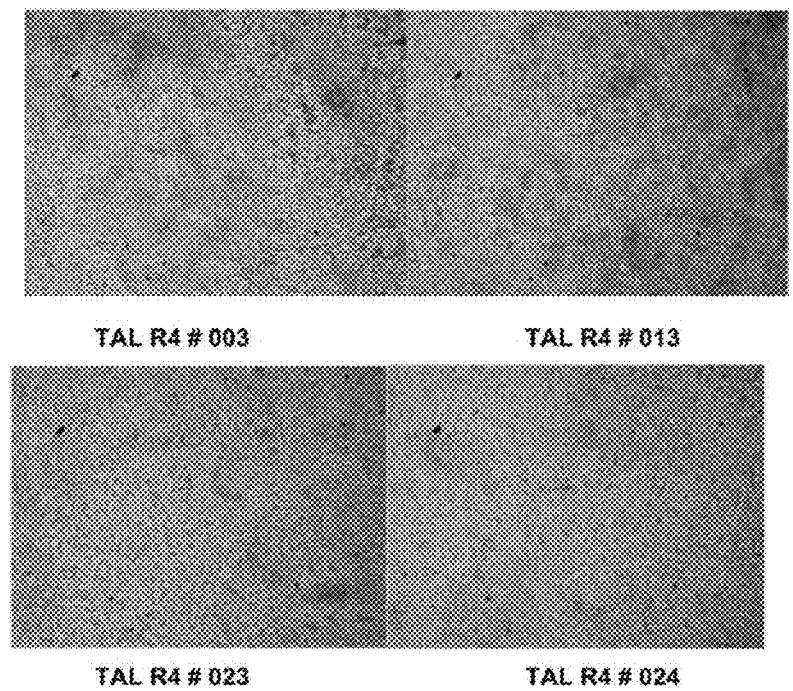

Results—During LCA selection of transfected clones, pictures of the clones on Day 1 are depicted in FIG. 5 and Day 11 pictures in FIG. 6 of the present disclosure. It is observed from FIGS. 5 and 6 that the following clones TAL R4 #003, TAL R4 #013, TAL R4 #023 and TAL R4 #024 maintain colony morphology even after treatment with 200 µg/ml LCA. Therefore these clones are considered to be potential FUT 8 knockout phenotype.

FIG. 5 and FIG. 6 depict results of Lens Culinaris Agglutinin (LCA) selection assay. Multiple single cell clonal cell line populations are separated in replica plates after transfection with TALEN constructs. These cell lines are then tested with 200 µg LCA reagent in the culture medium. The cells are observed every day to confirm cell health and morphology and photographs are taken at appropriate time points. FIG. 5 indicates photographs taken after one day of culture after LCA selection start point and FIG. 6 indicates photographs taken after 11 days of culture. The cell lines TAL R4#013, TAL R4#023 and TAL R4#024 indicated here show resistance against LCA depicted by few resistant cells on day one which has multiplied and grown into large colonies of cells after Day 11 of culture in presence of LCA reagent.

Figure 7:
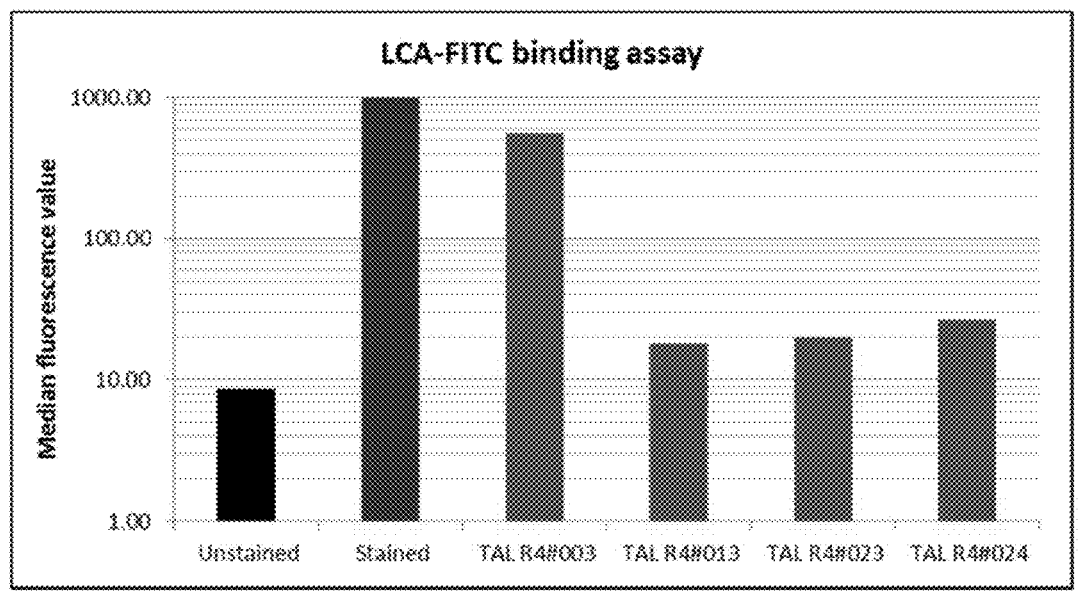

The graphical results and fluorescence profile provided in the table above are also depicted in FIGS. 7 and 8 of the present disclosure. FIGS. 7 and 8 depict the graphical result and fluorescence profile observed for the CHOK1 cell lines TAL R4#003, TAL R4#013, TAL R4#023 andTAL R4#024 in Flow cytometry based LCA-FITC Binding Assay. This flow cytometry assay detects fucosylated proteins present on cell surface. Thus CHOK1 control cells fluoresce highly as many fucosylated proteins are present in Control CHOK1 cell line. In cases where the TALEN constructs are able to disrupt the FUT8 gene in transfected cell lines, the LCA FITC fluorescence is minimized as there is no fucosylated protein on surface of these cell lines. FIGS. 7 and 8 reveal significant fluorescence loss when TAL R4#013, TAL R4#023 and TAL R4#024 are tested in this assay indicating these cell lines are CHOK1 FUT8 knock out cell lines.

It is observed from FIGS. 7 and 8 that TAL R4#013 shows complete shift in LCA-FITC binding profile and reveals expected afucosylated phenotype. TAL R4#003 shows about 50% reduction in LCA-FITC binding whereas TAL R4#023 and TAL R4#024 showed binding profile similar to mixed population of cellsTAL R4#013 is a potential FUT8 knock out clone. Clones TAL R4#023 and TAL R4#024 are studied in successive generations to achieve clonal population.

2.4—LCA (Lens Culinaris Agglutinin) Selection Assay—

A second set of LCA selection is done for 25 clones. Only one clone shows LCA resistant colony morphologyTAL-R4#111. Cell morphology is observed with microscope and observations are recorded on days 1, 9 and 11. Cells are regularly observed under the inverted phase contrast microscope and monitored for colony morphology, which is also depicted in FIG. 9 of the present disclosure.

Figure 9:
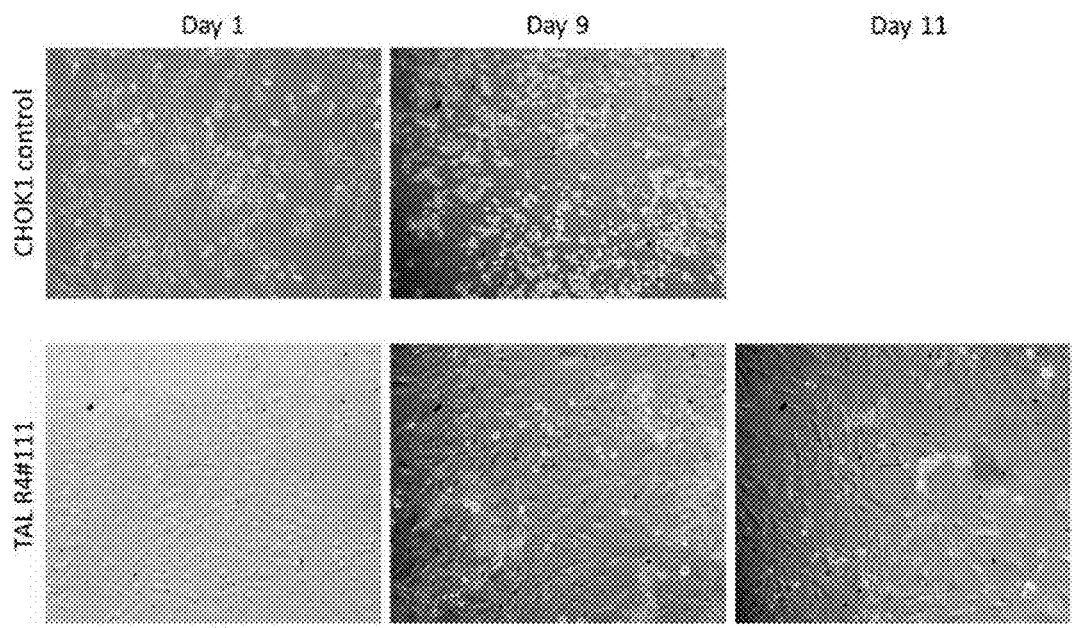
FIG. 9 depicts the inverted phase contrast microscope results for colony morphology of CHOK1 clones in LCA selection assay.

FIG. 9 depicts representative results from inverted phase contrast microscopy experiment to study colony morphology of CHOK1 control cells and one of the LCA resistant clones, TAL R4#111 in LCA selection assay. The photographs taken at different time points of LCA selection assay with 200 μg/ml LCA clearly show that CHOK1 control cells are completely dead at Day 9 of culture, whereas the TAL R4#111 clone shows continuous cell growth and healthy cell morphology even after 11 days of culture.

2.5—LCA-FITC Binding Assay:

For second set of LCA-FITC binding assay, following selected 5 clones are screened: TAL R4#003, TAL R4#013, TAL R4#023, TAL R4#024 and TAL R4#111. Fluorescein Lens Culinaris Agglutinin (LCA-FITC) stock of 5 mg/ml is diluted to get 2 μg/ml final concentration in assay buffer (DPBS containing 2% BSA). Cells are spun at 1500 rpm for 5 minutes using Eppendorf minispin centrifuge. The media is aspirated and the pellet re-suspended in 0.25-1 ml of assay buffer containing 2 μg/ml LCA-FITC. CHOK1 control cells are re-suspended in 0.25-1 ml of assay buffer alone (unstained control) and 0.25-1 ml of assay buffer containing 2 μg/ml LCA-FITC (stained control). All samples are diluted to get 0.1-0.2 X$10^6$ cells/ml in final assay buffer. The samples are then incubated in dark on ice for 30 minutes. Then 200 μl of each sample is aliquoted in a 96 well plate. The plate is then loaded in the Millipore GUAVA easyCyte 8HT benchtop flow cytometer for data acquisition and analysis. Data analysis is done using Incyte software.

TABLE 6

Results of LCA FITC flow cytometry assay

| Sl. No. | Sample ID | Median RFU |
| --- | --- | --- |
| 1 | Unstained control | 12.093 |
| 2 | Stained control | 922.471 |
| 3 | TAL R4#003 | 695.375 |
| 4 | TAL R4#013 | 26.188 |
| 5 | TAL R4#023 | 28.790 |
| 6 | TAL R4#024 | 37.445 |
| 7 | TAL R4#111 | 32.245 |

Figure 10:
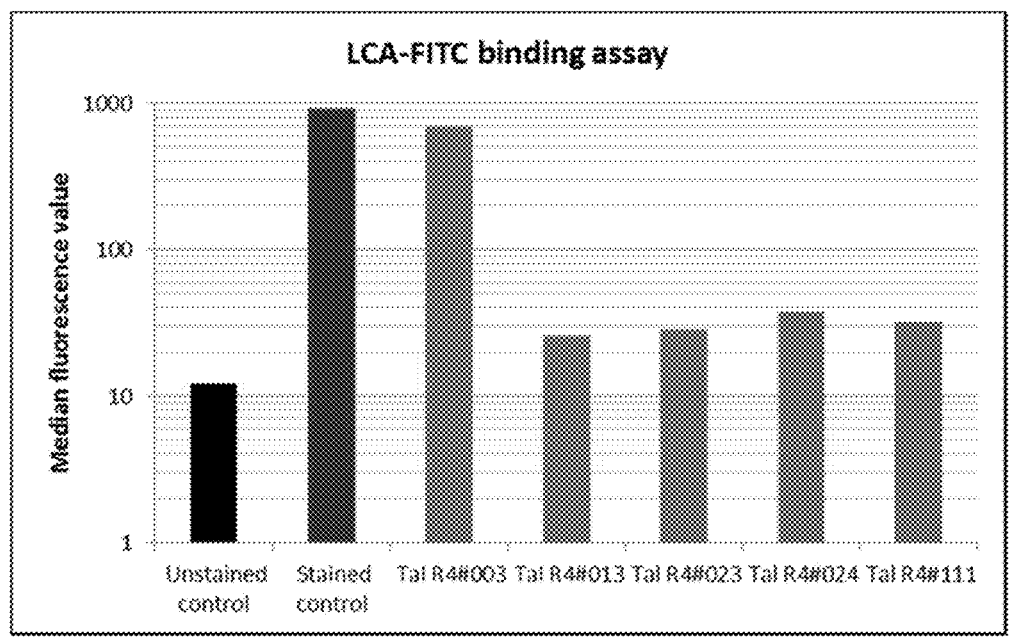

The results provided in the table above are also depicted in graphical representation in FIG. 10 and fluorescence profile in FIG. 11 of the present disclosure.

FIG. 10 and FIG. 11 depict the graphical result and fluorescence profile observed for the CHOK1 cell lines TAL R4#003, TAL R4#013, TAL R4#023, TAL R4#024 and TAL R4#111 in Flow cytometry based LCA-FITC Binding Assay. TAL R4#023 and TAL R4#024 cell lines are passaged for additional days before being analyzed in this experiment. This flow cytometry assay detects fucosylated proteins present on cell surface. Thus CHOK1 control cells fluoresce highly as many fucosylated proteins are present in Control CHOK1 cell line. In cases where the TALEN constructs are able to disrupt the FUT8 gene in transfected cell lines, the LCA FITC fluorescence is minimized as there is no fucosylated protein on surface of these cell lines. FIGS. 10 and 11 reveal significant fluorescence loss when TAL R4#013, TAL R4#023, TAL R4#024 and TAL R4#111 are tested in this assay indicating these cell lines are CHOK1 FUT8 knock out cell lines.

Two potential candidates, TAL R4 #013 and TAL R4#111 are validated for FUT8 knockout phenotype based on the shift in fluorescence profile. TAL R4#111 is a novel clone identified from second set of experiments. Also, this data validates the observation from first set of experiments for TAL R4#013. Other two clones TAL R4#023 and TAL R4#024 showed complete shift in fluorescence profile. The TAL R4#023 and TAL R4#024 cell lines have shown FUT8 knockout phenotype after 8-10 passages in culture to achieve clonal population.

EXAMPLE 3

Transfection of Cells with Talen Constructs Talen Transfection with High Cell Number to Improve Frequency of Talen Transfected Chok1 Cells 3.1 Transfection CHOK1 cells are seeded at more than 90% viability and a density of 0.5×$10^6$ cells/well in a 6 well tissue culture plate and allowed to adhere for 4 hrs. pcDNA3.1-TALEN_L6 and pcDNA3.1-TALEN_R6 constructs are transfected using Lipofectamine LTX with Plus™ reagent. 2.5 μg of each DNA construct is used with 1:5 DNA to transfection reagent ratio. The cells are incubated for 20-24 hrs after transfection. Prior to transfection, DNA quantity and quality is estimated by UV spectrophotometry. $A_{260/280}$ value DNA represents quality and protein contamination. The ratio of absorbance at 260 nm and 280 nm is used to assess the purity of DNA. $A_{260/280}$>1.8 is generally accepted as "pure" or good quality DNA. 3-4 μl of DNA sample is placed on the micro cuvette and DNA concentration is estimated using Eppendorf Biophotometer D30 against suitable blank.

TALEN DNA Dilution:

| | |
|---|---|
| For "n" number of wells | 2.5 µg * n |
| pcDNA3.1-TALEN_L6 | 2.5 µg * n |
| pcDNA3.1-TALEN_R6 | 2.5 µg * n |
| Plus ™ reagent | 1.33 µl * n |
| Media without serum | Up to 1.5 * n ml |

Lipofectamine LTX Dilution:

| | |
|---|---|
| Lipofectamine LTX | 25 µl * n |
| Media without serum | Up to 1.5 * n ml |

Media change is provided to the cells with serum free media, 1hour prior to transfection. TALEN DNA and Lipofectamine LTX solution are diluted, mixed gently and incubated for 10 minutes at 20-25° C. DNA and transfection reagent dilutions (3 ml) are mixed and incubated for 30 minutes at Room Temperature for complex formation. The media is aspirated from the wells. 1.5 ml of DNA and transfection reagent complex is added drop wise to the plated cells. The cells are incubated for 4 hours at 37° C. in a 5% $CO_2$ Incubator. The complete media is added at 1.5 ml/well and incubated for 20-24 hours at 37° C. in a 5% $CO_2$ Incubator. After 20-24 hours of transfection, cells are trypsinized and followed by single cell dilution.

Single cell dilution is obtained by serial dilution of the cells to a concentration of 0.5 cell/100 µl. Cell count is taken using hemocytometer. After process optimization the CHOK1 cells are seeded at a density of 0.5 cells/100 µl/well and showed good yield of single cell colonies. The cells are allowed to grow for few days at 37° C. in a 5% $CO_2$ Incubator. Plate scanning is done to identify single cell colonies under the inverted phase contrast microscope. Cells growing into distinctly small single colonies are marked for further amplification. After 2-3 weeks, single cell clones are amplified from one well of 96 well plate to one well of 6 well plate by trypsinization. Cells are allowed to grow for 2-3 days at 37° C. at 5% $CO_2$ in a $CO_2$ incubator. Cells are further amplified from one well to two wells in a 24 well plate (replica plating) for further screening.

3.2—LCA (Lens Culinaris Agglutin) Selection Assay—

LCA selection of the clones is initiated at 200 µg/ml for clone TAL R5 #1-115. Following clones have shown healthy colony morphology under LCA selection: TAL R5#007, TAL R5#009, TAL R5#010, TAL R5#016, TAL R5#032, TAL R5#045, TAL R5#047, TAL R5#052, TAL R5#064, TAL R5#066, TAL R5#067, TAL R5#095, TAL R5#099 and TAL R5#114. Cells are observed under the microscope at regular intervals till day 11. These clones are selected for their LCA resistant phenotype. Cell are amplified into 2 wells of 6 well plate by trypsinization from master plate (replica plating) and are allowed to grow for 6-7 days at 37° C. in a 5% CO2 incubator.

3.3—LCA-FITC Binding Assay:

A separate set of LCA-FITC binding assay is carried out with following 14 clones TAL R5#007, TAL R5#009, TAL R5#010, TAL R5#016, TAL R5#032, TAL R5#045, TAL R5#047, TAL R5#052, TAL R5#064, TAL R5#066, TAL R5#067, TAL R5#095, TAL R5#099 and TAL R5#114. Fluorescein Lens Culinaris Agglutinin (LCA-FITC) stock 5 mg/ml is diluted to get 2 µg/ml final concentration in assay buffer (DPBS containing 2% BSA). Cells are spun at 1500 rpm for 5 minutes using Eppendorf minispin centrifuge. The media is aspirated and the pellet re-suspended in 0.25-1 ml of assay buffer containing 2 µg/ml LCA-FITC. CHOK1 control cells are re-suspended in 0.25-1 ml of assay buffer alone (unstained control) and 0.25-1 ml of assay buffer containing 2 µg/ml LCA-FITC (stained control). All the samples are diluted to get $0.1$-$0.2 \times 10^6$ cells/ml in final assay buffer. The samples are then incubated in dark on ice for 30 minutes. Then 200 µl of each sample is aliquoted in a 96 well plate. The plate is then loaded in the Millipore GUAVA easyCyte 8HT benchtop flow cytometer for data acquisition and analysis. Data analysis is done using Incyte software.

TABLE 7

Results - set 1

| Sl. No. | Samples | Median RFU |
|---|---|---|
| 1 | Unstained control | 10.791 |
| 2 | LCA-FITC stained control | 967.904 |
| 3 | TAL R5#007 | 14.062 |
| 4 | TAL R5#009 | 603.129 |
| 5 | TAL R5#010 | 11.859 |
| 6 | TAL R5#016 | 935.036 |
| 7 | TAL R5#032 | 711.403 |
| 8 | TAL R5#045 | 15.992 |
| 9 | TAL R5#047 | 18.271 |
| 10 | TAL R5#052 | 705.069 |
| 11 | TAL R5#064 | 460.910 |
| 12 | TAL R5#066 | 18.097 |
| 13 | TAL R5#067 | 799.150 |
| 14 | TAL R5#095 | 12.050 |
| 15 | TAL R5#099 | 20.335 |
| 16 | TAL R5#114 | 18.171 |

Median RFU refers to median value of Relative Fluorescence Unit.

Figure 13:
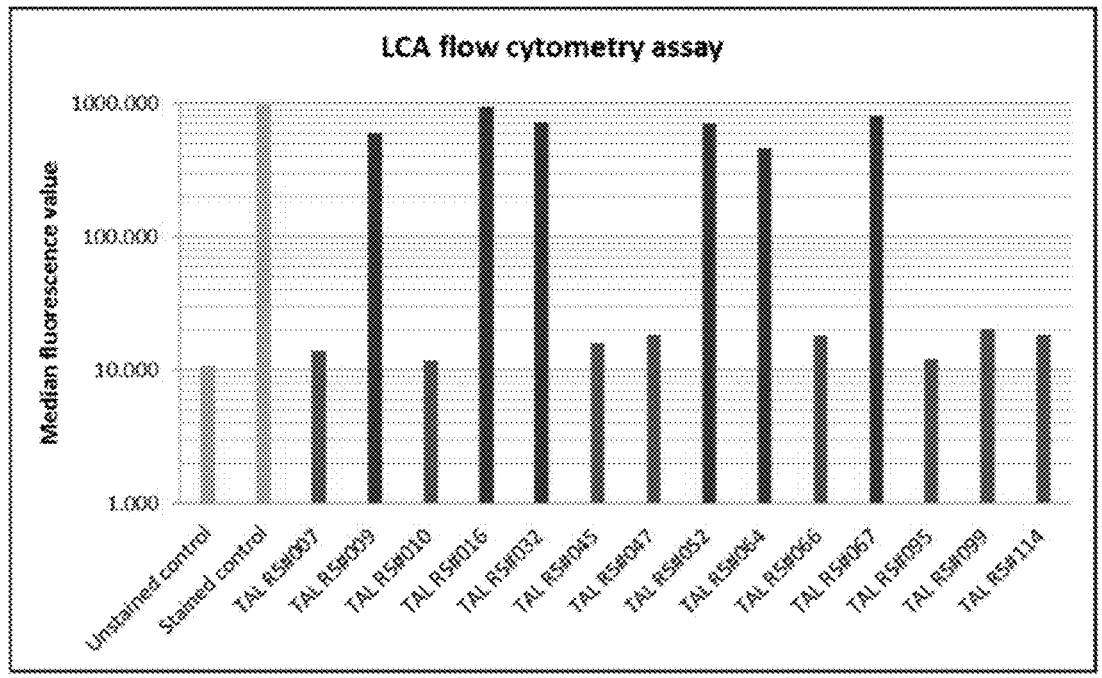
FIGS. 13 and 14 depict the LCA Flow cytometry assay, and comparison of the CHOK1 clones through LCA-FITC and Strep-FITC flow cytometry assay.
Figure 14:
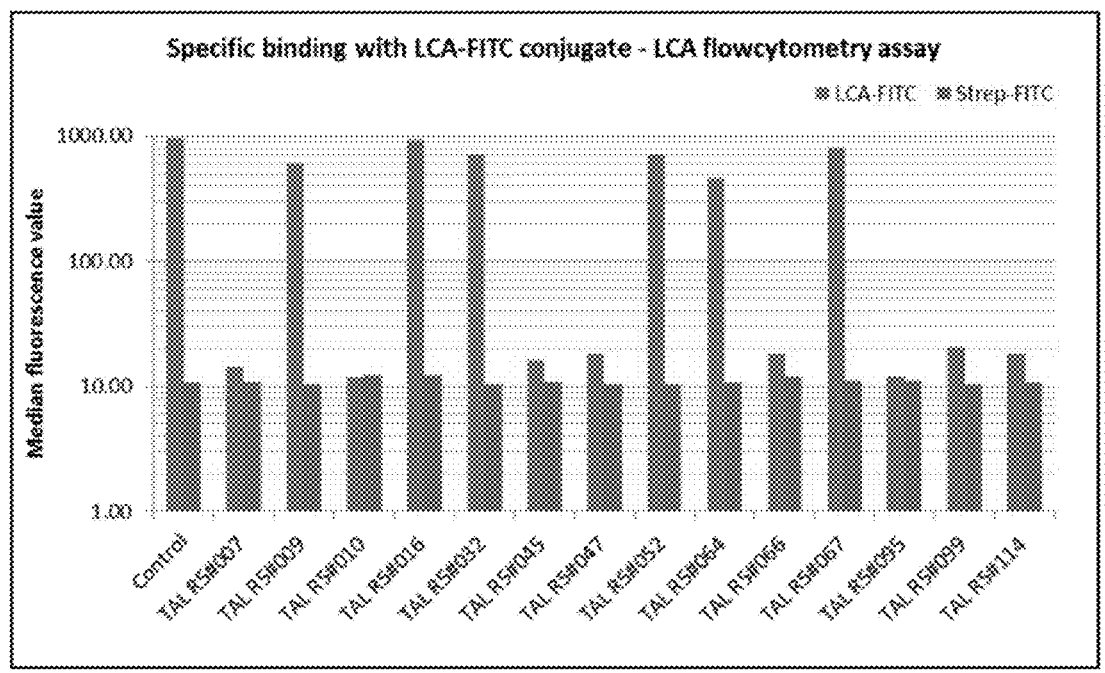

FIGS. 13 and 14 of the present disclosure depict the LCA Flow cytometry assay, and comparison of the clones through LCA-FITC and Strep-FITC assay respectively. For the following 8 clones Fut8 knockout phenotype is observed, TAL R5#007, TAL R5#010, TAL R5#045, TAL R5#047, TAL R5#066, TAL R5#095, TAL R5#099 and TAL R5#114. In all these 8 clones, a significant reduction of fluorescence compared to control is observed and thereby this proves absence of fucosylated protein on cell surface for the clones. This data provides functional proof that these cell lines lack fucosylated protein due to FUT8 gene disruption carried out using the TALEN constructs in the method of the present disclosure.

FIG. 13 depicts the LCA Flow cytometry assay, and comparison of the CHOK1 clones through LCA-FITC flow cytometry assay. CHOK1 cell lines TAL R5#007, TAL R5#009, TAL R5#010, TAL R5#016, TAL R5#032, TAL R5#045, TAL R5#047, TAL R5#052, TAL R5#064, TAL R5#066, TAL R5#067, TAL R5#095, TAL R5#099 and TAL R5#114 are tested in Flow cytometry based LCA-FITC Binding Assay. This flow cytometry assay detects fucosylated proteins present on cell surface. Thus CHOK1 control cells fluoresce highly as fucosylated proteins are present in Control CHOK1 cell line. In cases where the TALEN constructs are able to disrupt the FUT8 gene in transfected cell lines, the LCA FITC fluorescence is minimized as there is no fucosylated protein on surface of these cell lines. FIG. 13 reveals significant fluorescence loss when TAL R5#007, TAL R5#010, TAL R5#045, TAL R5#047, TAL R5#066, TAL R5#95, TAL R5#099, and TAL R5#114 are tested in this assay indicating these cell lines are CHOK1 FUT8 knock out cell lines.

Figure 15:
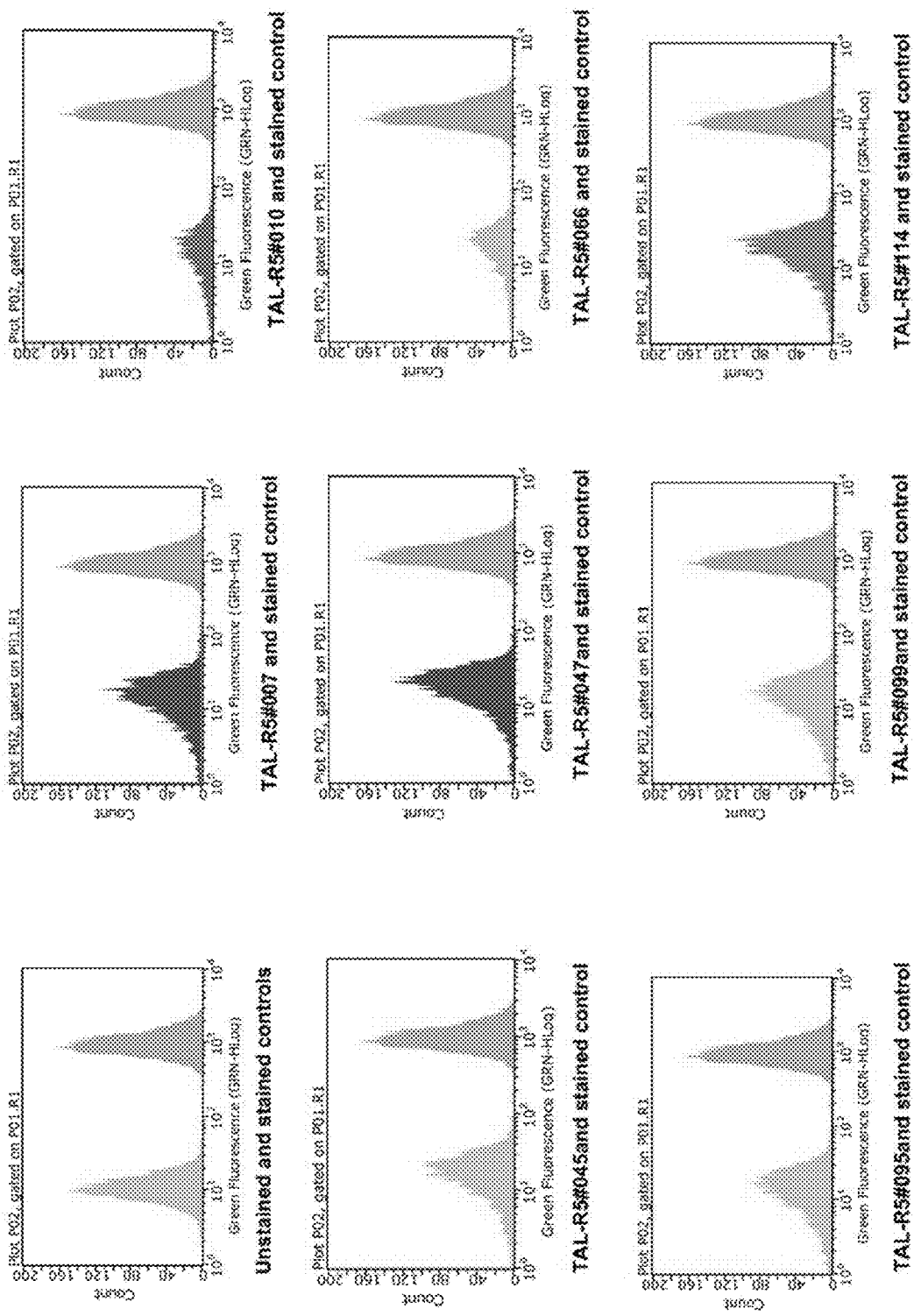
FIG. 15 depicts the fluorescence profile for the LCA-FITC binding assay and Strep-FITC assay.

FIGS. 14 and 15 depict the specificity of the LCA-FITC flow cytometry assay developed to screen the CHOK1 FUT8 knock out cell lines. Flow cytometry experiments are carried out with Streptavidin-FITC conjugate. Streptavidin-FITC does not recognize cell surface proteins on CHOK1 control cell line indicating specific interaction of LCA-FITC conjugate. Additionally, the Streptavidin-FITC conjugate reveals similar levels of background fluorescence between positive and negative cell lines identified by LCA-FITC conjugate.

3.4—LCA (Lens Culinaris Agglutin) Selection Assay—

Another set of cell lines are used for LCA selection at 200 µg/ml for clone TAL R5 #116 to TAL R5#209. Following clones are found to be growing healthy when cell morphology parameters are compared: TAL R5#125, TAL R5#131, TAL R5#154, TAL R5#161, TAL R5#165, TAL R5#171, TAL R5#172 andTAL R5#176. Cells are observed under the microscope at regular intervals till day 11. These clones are selected for their LCA resistant phenotype. Cell are amplified into 2 wells of 6 well plate by trypsinization from master plate (replica plating) and are allowed to grow for 6-7 days at 37° C. in a 5% CO2 incubator.

FIG. 16 of the present disclosure depicts pictures of TALEN transfected CHOK1 clones in the LCA selection assay. Multiple single cell clones are tested in replica plates through LCA selection assay. CHOK1 control cell line is also tested along with CHOK1 cells transfected with TALEN constructs. Microscopic observation of cell lines after 11 days of LCA selection reveals complete death in CHOK1 control cells and one of the clones TAL R5#125. Remaining clones TAL R5#131, TAL R5#154, TAL R5#161, TAL R5#165, TAL R5#171, TAL R5#172 and TAL R5#176 reveal resistant cells after 11 days of LCA selection at 200 µg/ml of LCA reagent per media. These clones are selected for further confirmation by LCA-FITC binding assay.

3.5—LCA-FITC Binding Assay:

LCA-FITC binding assay for the following 8 clones is carried out: TAL R5#125, TAL R5#131, TAL R5#154, TAL R5#161, TAL R5#165, TAL R5#171, TAL R5#172 and TAL R5#176. Fluorescein Lens Culinaris Agglutinin (LCA-FITC) stock 5 mg/ml is diluted to get 2 µg/ml final concentration in assay buffer (DPBS containing 2% BSA). Cells are spun at 1500 rpm for 5 minutes using Eppendorf minispin centrifuge. The media is aspirated and the pellet re-suspended in 0.25-1 ml of assay buffer containing 2 µg/ml LCA-FITC. CHOK1 control cells are re-suspended in 0.25-1 ml of assay buffer alone (unstained control) and 0.25-1 ml of assay buffer containing 2 µg/ml LCA-FITC (stained control). All the samples are diluted to get $0.1-0.2 \times 10^6$ cells/ml in final assay buffer. The samples are then incubated in dark on ice for 30 minutes. Then 200 µl of each sample is aliquoted in a 96 well plate. The plate is then loaded in the Millipore GUAVA easyCyte 8HT benchtop flow cytometer for data acquisition and analysis. Data analysis is done using Incyte software.

TABLE 8

| Sl. No. | Sample ID | Median RFU |
|---|---|---|
| | Results - set 2 | |
| 1 | Unstained control | 11.155 |
| 2 | LCA-FITC stained control | 1000.340 |
| 3 | TAL R5#125 | 1130.019 |
| 4 | TAL R5#131 | 22.749 |
| 5 | TAL R5#154 | 29.872 |
| 6 | TAL R5#161 | 17.920 |
| 7 | TAL R5#165 | 21.880 |
| 8 | TAL R5#171 | 20.169 |
| 9 | TAL R5#172 | 18.669 |
| 10 | TAL R5#176 | 25.544 |

Median RFU refers to median value of Relative Fluorescence Unit.

Figure 17:
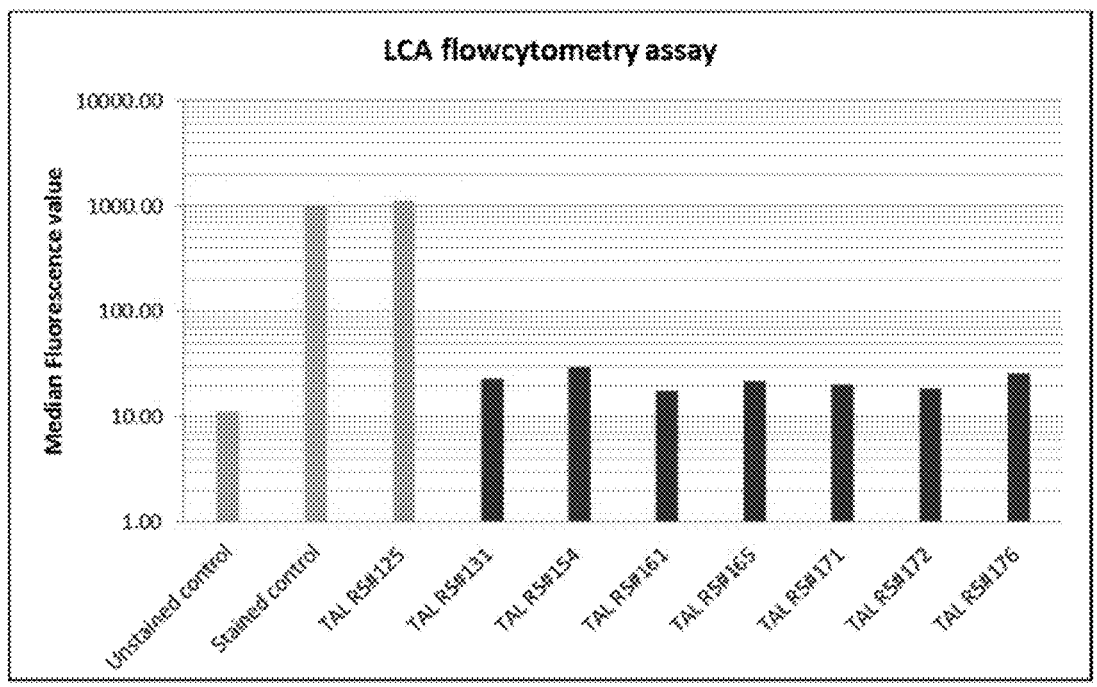
FIGS. 17 and 18 depict results of the LCA Flow cytometry assay, and comparison of the CHOK1 clones through LCA-FITC and Strep-FITC flow cytometry assay.
Figure 18:
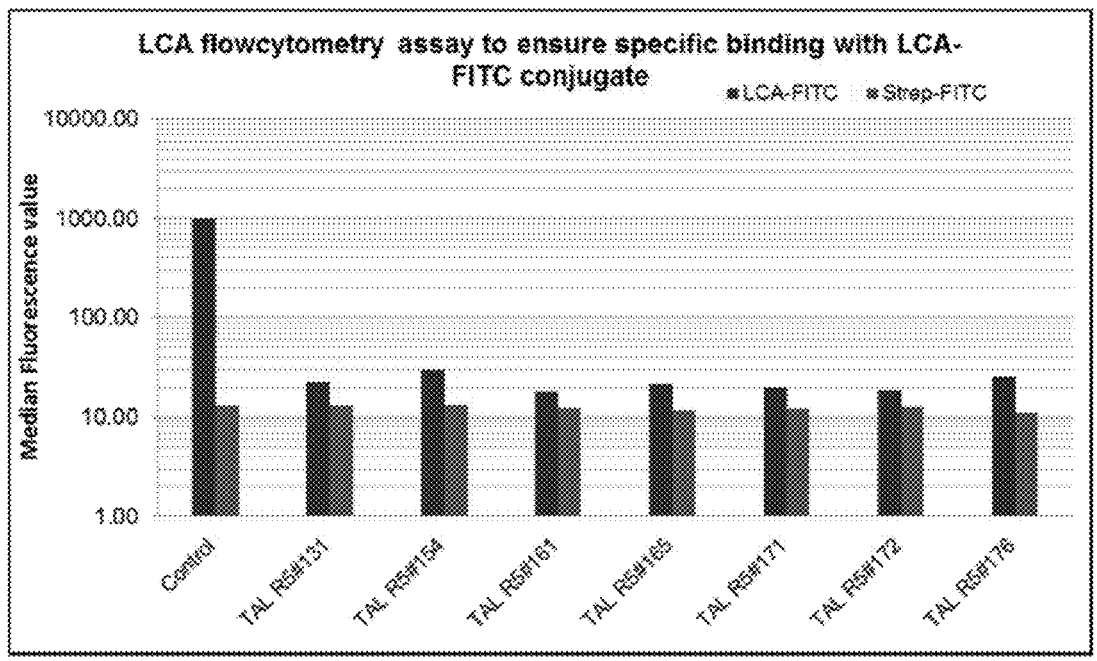
Figure 19:
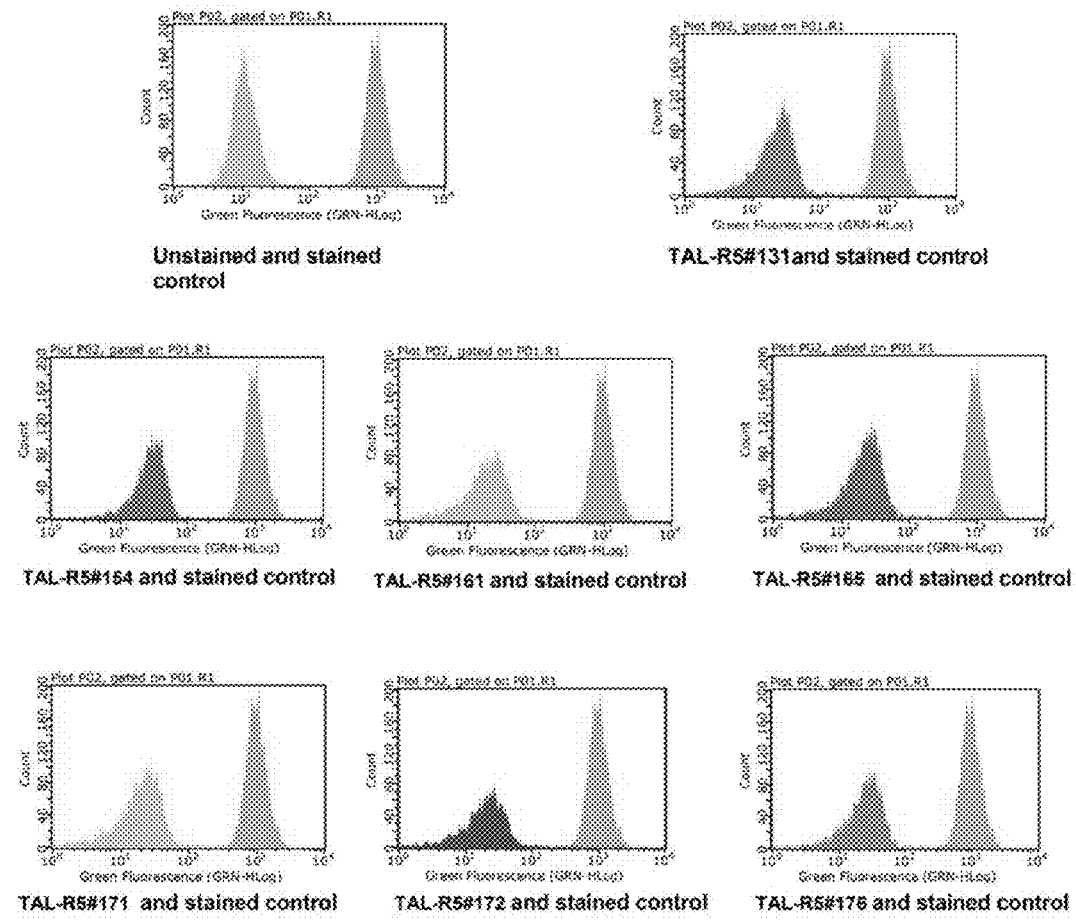
FIG. 19 depicts the fluorescence profile for the CHOK1 clones through LCA-FITC and Strep-FITC flow cytometry assay.

FIGS. 17 and 18 of the present disclosure depict the LCA-FITC fluorescence assay results and comparison with the Streptavidin-FITC assay as per the above table. FIG. 19 depicts the Fluorescence profile. Clones TAL R5#125, TAL R5#131, TAL R5#154, TAL R5#161, TAL R5#165, TAL R5#171, TAL R5#172 and TAL R5#176 are tested for LCA-FITC flow cytometry assay.

It is derived from FIGS. 17, 18 and 19 that the following 7 clones are positive for FUT8 knockout phenotype TAL R5#131, TAL R5#154, TAL R5#161, TAL R5#165, TAL R5#171, TAL R5#172 and TAL R5#176. All the above mentioned clones reveal significant reduction of fluorescence compared to CHOK1 control cell line. Comparison with Streptavidin-FITC is carried out to ensure specific interaction of LCA-FITC conjugate. The data suggests only background fluorescence observed with Streptavidin-FITC conjugate when tested with CHOK1 control cell line and any of the TALEN transfected cell lines. FIG. 18 shows no non-specific interaction of LCA-FITC conjugate used in this study when compared to Streptavidin-FITC conjugate.

FIG. 19 depicts the fluorescence profile for the CHOK1 FUT8 knock out clones through LCA-FITC flow cytometry assay. Flow cytometry profiles of clones TAL R5#131, TAL R5#154, TAL R5#161, TAL R5#165, TAL R5#171, TAL R5#172, and TAL R5#176 show clear shift in fluorescence compared to CHOK1 control cell line. The data clearly indicates these clones are potential CHOK1 FUT8 knock out cell lines.

3.6 Streptavidin-FITC Staining to Eliminate Non Specific Binding of FITC Dye

Streptavidin conjugated FITC (Strep-FITC) staining of the clones is carried out to ensure that there is no non-specific binding of FITC dye. Cell membrane proteins do not bind to Streptavidin-FITC conjugate whereas fucosylated membrane proteins bind specifically to LCA-FITC conjugate. Control CHOK1 cells are stained with both LCA-FITC and Strep-FITC in separate reactions to confirm this specificity. All clones are similarly stained with Streptavidin-FITC and LCA-FITC conjugates to determine non-specific binding.

Following 14 clones are screened from the previous set of experiments:—TAL R5#007, TAL R5#009, TAL R5#010, TAL R5#016, TAL R5#032, TAL R5#045, TAL R5#047, TAL R5#052, TAL R5#064, TAL R5#066, TAL R5#067, TAL R5#095, TAL R5#099 and TAL R5#114.

Similarly, another 8 clones from a separate experiment are also screened: are TAL R5#125, TAL R5#131, TAL R5#154, TAL R5#161, TAL R5#165, TAL R5#171, TAL R5#172 and TAL R5#176.

Fluorescein streptavidin (Streptavidin-FITC) stock 1 mg/ml is diluted to get 2 µg/ml final concentration in assay buffer (DPBS containing 2% BSA). Cells are spun at 1500 rpm for 5 minutes using Eppendorf minispin centrifuge. The media is aspirated and the pellet re-suspended in 0.25-1 ml of assay buffer containing 2 µg/ml Streptavidin-FITC. CHOK1 control cells are re-suspended in 0.25-1 ml of assay buffer alone (unstained control) and 0.25-1 ml of assay buffer containing 2 µg/ml Streptavidin-FITC (stained control). All samples are diluted to get $0.1$-$0.2 \times 10^6$ cells/ml in final assay buffer. The samples are then incubated in dark on ice for 30 minutes. Then 200 µl of each sample is aliquoted in a 96 well plate. The plate is then loaded in the Millipore GUAVA easyCyte 8HT benchtop flow cytometer for data acquisition and analysis. Data analysis is done using Incyte software.

Comparison with Streptavidin-FITC is carried out to ensure specific interaction of LCA-FITC conjugate. The data suggests only background fluorescence observed with Streptavidin-FITC conjugate when tested with CHOK1 control cell line and any of the TALEN transfected cell lines. FIG. 18 shows no non-specific interaction of LCA-FITC conjugate used in this study when compared to Streptavidin-FITC conjugate.

TABLE 9

Results - set1 and set2

| Sl. No. | Sample ID | Median RFU LCA-FITC | Median RFU Strep-FITC |
|---|---|---|---|
| 1 | Control CHOK1 | 1000.340 | 12.964 |
| 2 | TAL R5#07 | 14.062 | 10.803 |
| 3 | TAL R5#09 | 603.129 | 10.524 |
| 4 | TAL R5#10 | 11.859 | 12.316 |
| 5 | TAL R5#16 | 935.036 | 12.189 |
| 6 | TAL R5#32 | 711.403 | 10.415 |
| 7 | TAL R5#45 | 15.992 | 10.878 |
| 8 | TAL R5#47 | 18.271 | 10.424 |
| 9 | TAL R5#52 | 705.069 | 10.414 |
| 10 | TAL R5#64 | 460.910 | 10.578 |
| 11 | TAL R5#66 | 18.097 | 12.123 |
| 12 | TAL R5#67 | 799.150 | 11.061 |
| 13 | TAL R5#95 | 12.050 | 11.123 |
| 14 | TAL R5#99 | 20.335 | 10.455 |
| 15 | TAL R5#114 | 18.171 | 10.656 |
| 16 | TAL R5#125 | 1130.019 | 12.937 |
| 17 | TAL R5#131 | 22.749 | 12.950 |
| 18 | TAL R5#154 | 29.872 | 13.298 |
| 19 | TAL R5#161 | 17.920 | 12.211 |
| 20 | TAL R5#165 | 21.880 | 11.863 |
| 21 | TAL R5#171 | 20.169 | 12.128 |
| 22 | TAL R5#172 | 18.669 | 12.688 |
| 23 | TAL R5#176 | 25.544 | 11.271 |

The Fluorescence profile is depicted in FIG. 15 of the present disclosure. Fluorescence flow cytometry profiles of the TAL R5#007, TAL R5#010, TAL R5#045, TAL R5#047, TAL R5#066, TAL R5#95, TAL R5#099, and TAL R5#114 clones are presented. It is derived from FIG. 15 that all clones mentioned above show significant shift in fluorescence profile compared to the CHOK1 control cell line after LCA-FITC staining. Streptavidin-FITC (Strep-FITC) staining profile of all clones is observed at the background level including the CHOK1 control cell line and all TALEN transfected cell lines. The data confirms that Streptavidin-FITC conjugate does not bind to CHOK1 cell membrane in CHOK1 control as well as the TALEN transfected cell lines. The reduction of fluorescence observed in the positive clones signifies absence of fucosylated proteins on TALEN transfected potential FUT8 knock out cell lines. This indicates that all these lines are potentially CHOK1 FUT8 Knock out cell lines.

3.7—Growth Curve Determination of Selected Clone:

Growth curve determination of selected clones are performed to ensure that growth profile is not altered significantly compared to wild type CHOK1 cells during the process of knockout cell line development. $0.1 \times 10^6$ CHOK1 cells are seeded in 6 well tissue culture plates. Seeding is done for 5 time points for each clone. For each time point, triplicate seeding is done (e.g., 15 wells for 5 time points). At each time, point cell counts are taken in triplicates. Viable cell count is performed using either hemocytometer or Vi-cell XR cell viability analyser. Respective growth curves are generated with SEM as error bar. Table 10 describes representative growth data from one of the FUT8 knock out cell line, TAL-R4#013.

TABLE 10

| Tal-R4# 013 | | |
|---|---|---|
| Time (hrs) | Mean | SEM |
| 0 | 0.100 | 0.000 |
| 24 | 0.307 | 0.062 |
| 48 | 0.984 | 0.075 |
| 72 | 2.395 | 0.030 |
| 96 | 5.731 | 0.260 |

Figure 12:
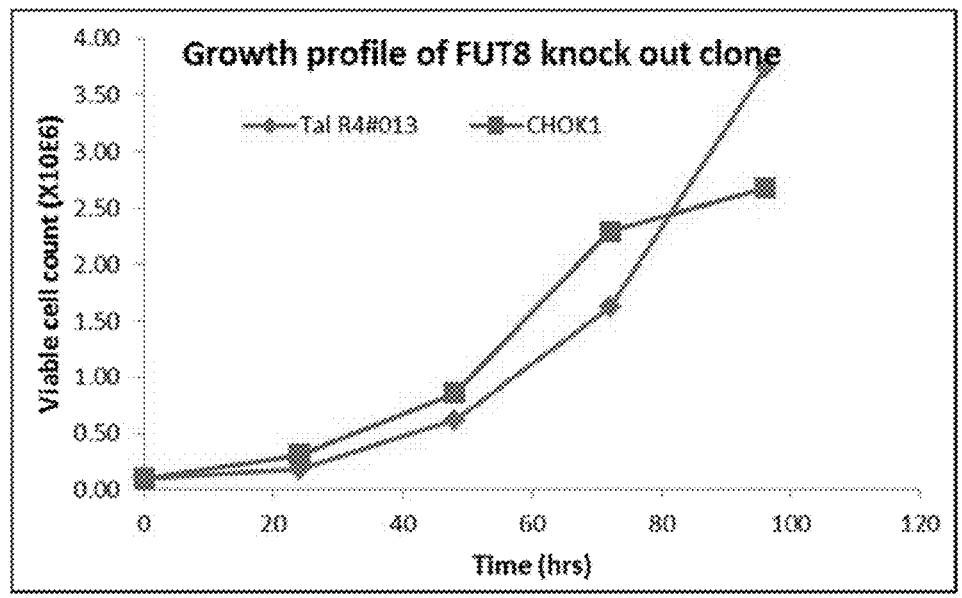
FIG. 12 depicts the graphical representation of Growth curve determination for Fut8 knockout clones.

The graph for the table presented above is provided in FIG. 12 of the present disclosure. It is observed from FIG. 12 that the clone TAL R4#013 has similar growth profile and doubling time to CHOK1 cells. All TALEN transfected clones confirmed with LCA-FITC flow cytometry assay are studied in parallel and FIG. 12 is representative of TAL R4#013 clone only.

FIG. 12 depicts representative graphical representation of growth curve of CHOK1 FUT8 knock out clones. Fucose knock out cell lines developed after TALEN constructs transfection are tested for optimal growth characteristics. These clonal cell lines are used for overexpression of therapeutic proteins and/or monoclonal antibodies. Viable cell count is taken every day for 5 days in optimal growth conditions, using Vi-Cell counter. Growth curves of the CHOK1 control cell line and clonal TAL R4#013 CHOK1 FUT8 knock out cell line are comparable.

EXAMPLE 4

Genomic Sequencing Assays

TALEN transfected clones selected through functional assay namely LCA-FITC flow cytometry assay are used for genomic sequence analysis. The FUT 8 genomic locus of Chinese Hamster is well reported in literature (NW_003613860) and is used as wild type sequence to understand type of gene modification in each cell line clone. The objective of this example is to analyse genomic DNA sequencing results obtained from TALEN transfected CHOK1 FUT8 knock out cell lines. All cell lines reported here are clonal cell lines and are selected from LCA media selection assay and LCA-FITC flowcytometry assay.

Briefly, the selected clonal cell lines are grown in appropriate growth conditions for genomic DNA isolation, purified genomic DNA is used for PCR amplification using primers flanking the FUT8 target locus, the PCR amplified product is then purified and cloned in a suitable vector using *E. coli* competent cells, resulting ampicillin resistant *E coli* colonies are selected and cultured, plasmid DNA are isolated from each bacterial clone, approximately 5-10 individual bacterial colonies are tested per clonal cell lines through automated sequencing to understand the type of modification at the FUT8 target genomic locus.

Following reagents and solutions are used to carry out genome sequencing of the selected clones The entire genome sequencing protocol is divided in following four processes
   A. Genomic DNA isolation from selected clones
   B. PCR strategy to amplify specific genomic locus for each cell line.
   C. Cloning of PCR products in sequencing vectors
   D. Sequence data analysis and identification of INDELs
4.1 Genomic DNA Isolation from Selected Clones Clonal CHOK1 cell lines are grown in Advanced DMEM media with 10% Fetal bovine serum, 4 mM glutamine, 100 units/ml Penicillin and 100 µg/ml Streptomycin in T175 flasks at 37° C. in presence of 5% $CO_2$ and 75% Relative Humidity in controlled condition incubators. The cell growth is observed every day and viability is monitored. Cells are harvested at 80% confluency and greater than 95% viability with trypsinization. On the day of isolation, culture media is removed and adherent cells are first washed with 10 ml of DPBS followed by addition of 4 milliliter of 0.05% trypsin EDTA solution for trypsinization. The cells are incubated at 37° C. for 2-3 minutes and harvested. Cells are then mixed with 10 ml of DPBS and centrifuged at 1500 rpm for 5 min. The spent media is removed and cell pellet is resuspended in 10 ml DPBS. Cells are washed again using centrifugation at 1500 rpm for 5 min. DPBS is removed completely by aspiration. The final cell pellet is used for genomic DNA isolation.

Genomic DNA is isolated from CHOK1 control cells and CHOK1 TALEN transfected clonal cell lines showing LCA resistance and selected through LCA flow cytometry assay. Commercially available QIAGEN gDNA extraction kit is used for isolating genomic DNA following manufacturers protocol.

4.2—PCR Strategy Design

Genomic DNA sequence of Chinese Hamster is analysed from publicly available database sequence NW_003613860. Exon 9 and 10 DNA sequences and partial intron sequence (Sequence ID No. 40.) is used for designing PCR strategy to amplify the FUT8 target locus. Primers are designed based on primer length, PCR product length, GC content, melting temperature and potential homoduplex and heteroduplex formation. Primers are designed flanking the FUT8 target locus as provided below. The amplified PCR product is intended for mutation analysis due to TALEN mediated DSB and subsequent DNA repair. Following nucleotide sequence represents the region of interest with primer sequences in bold letters.

gacctgtactattcaacattcagctatgttaaagtatttgtgaagtgttt tgaaatgattttatattttctaaggtgagaataaatgagaaaatgtttta atatgtctccagtgccccatgactagggatactaattgagtaccagtac attatcagtgtgctctccacttctccccagAGTCCATGTCAGACGCACTG

ACAAAGTGGGAACAGAAGCAGCCTTCCATCCCATTGAGGAATACATGGTA

CACGTTGAAGAACATTTTCAGCTTCTCGAACGCAGAATGAAAGTGGATAA

AAAAAGAGTGTATCTGGCCACTGATGACCCTTCTTTGTTAAAGGAGGCAA

AGACAAAgtaagttagaccaacaagtggttctgtatgggattatctc

Introns are represented from base 1 to base 180 and from base 358 to base 397 in lower case letters. Exon 9 is represented from base 181 to base 357 in upper case letters. The primer binding sites of Left and Right are underlined.

4.2.1 Primer Design for Identifying the INDEL by PCR

Genomic PCR is performed using QIAGEN gDNA extraction kit using the following primers mentioned in table 11.

TABLE 11

| PCR Sets | Primer Name | Primer sequence (5' to 3') | PCR product size | Base | Tm | % GC |
|---|---|---|---|---|---|---|
| TAL primers | TAL_P01_Fw | GACCTGTACTATTCAACAT TCAGC -SEQ ID No. 41 | 397 bp | 24 | 54 | 42 |
| | TAL_P01_Rv | GAGATAATCCCATACAGA ACCAC - SEQ ID No. 42 | | 23 | 54 | 43 |

Following section provides experimental details for PCR product generation from CHOK1 genomic DNA from control cell lines and LCA selected clonal cell lines, cloning of PCR products in E coli competent cells and sequencing of cloned PCR products.

4.2.2 Optimization of PCR Condition—

Experiments are designed to standardize PCR conditions. The parameters tested include, genomic DNA concentration (from 100 ng to 1000 ng), primer concentrations (2 nmole to 20 nmole), PCR annealing temperature (from 55.8° C. to 62.9° C. and time (20 secs to 50 secs), PCR product extention time (30 secs to 60 secs) and PCR cycle number is set at 30 cycles. Arrived optimized condition is described in following section. PCR reactions are carried out using proof reading polymerase Phusion polymerase to ensure that PCR mediated mutations are limited. Following PCR amplification cycles, Taq polymerase enzyme is added in the mix for tailing. The tailing step is important as the extra base added to the PCR products allows direct cloning in sequencing vector described in next section. In order to add dATP overhangs to PCR product for cloning in TA cloning vector, the Phusion polymerase amplified product is incubated with Taq DNA polymerase for 15 minutes at 72° C.

4.2.3 Cross Checking the Genomic DNA Sample by PCR—

Genomic DNA PCR products are analysed in agarose gel electrophoresis and the product length is confirmed using a molecular weight standard. PCR samples with clear amplification profile are used in next processing step.

4.2.4—PCR Product Gel Elution Using QIAGEN Kit—

The amplified PCR products are loaded in freshly prepared 1% agarose gel and electrophoresed at 100V for one hour) to separate amplified PCR products from unused primers and any other dimers produced during the amplification process. The amplified products are excised from gel and eluted using commercially available Qiagen gel elution kit. DNA is eluted with highly pure molecular biology grade water.

4.3 Cloning of PCR Products in Sequencing Vectors—

Agarose gel purified PCR amplified products are then used for cloning in commercially available pTZ57R/T vector through DNA ligation process. Conditions for DNA ligation have been standardized previously.

4.3.1 Transformation of Ligated Sample pTZ57R/T+TAL (PCR) in DH10B and DH5alpha E coli Competent Cells—

Ligated DNA is transformed in E coli DH10B competent cells, available commercially. Transformation protocol as described by manufacturer is followed to achieve high level transformation efficiency. After transformation, the E coli cells are grown in presence of Ampicillin antibiotic for growth of transformed colonies.

4.3.2 Inoculation of Transformed Cells (pTZ57R/T+TAL (PCR)) into LB Media with Ampicillin—

Each separate colony is inoculated in LB+Ampicillin broth in 5 mililiter culture volume and grown overnight for plasmid DNA isolation.

4.3.4 Isolation of Plasmid DNA (pTZ57R/T+TAL(PCR) from DH10B and DH5alpha Transformed Cells—

4.5 mililiter of overnight grown cultures are used for plasmid DNA isolation using commercially available QIAGEN plasmid DNA isolation kit following manufacturers protocol. The plasmid DNA is eluted with highly pure molecular biology grade water.

4.3.5 Cross Checking of Plasmids for the Presence of Insert—

Each plasmid preparation is tested for presence of insert using suitable restriction enzyme digestion followed by agarose gel electrophoresis. The size of insert is compared with suitable molecular weight standards.

4.4. Sequence Data Analysis and Identification of INDELs

Sequencing—The confirmed plasmids are then sequenced with specific sequencing primers present in the pTZ57R/T vector backbone. Sequence data is generated in automated DNA sequencing instruments following appropriate protocols. Sequencing is carried out with both forward and reverse sequencing primers to ensure proper sequence information.

DNA Sequence Analysis—DNA sequencing data from all plasmids are analyzed. DNA sequence from plasmid DNA derived from CHOK1 control cell line and various TALEN mediated FUT8 knock out CHOK1 clonal cell lines are compared and differences in DNA sequences are identified. From each CHOK1 cell line clone, PCR products are generated and cloned in E coli. Multiple E coli clones are sequenced to confirm nucleotide sequence modification at the target genomic locus.

Figure 26:
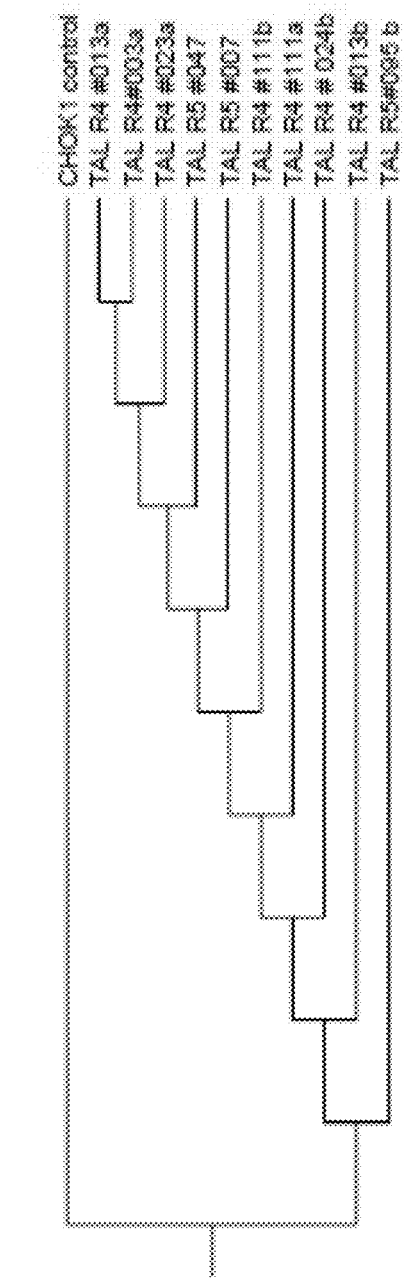
FIG. 26 depicts alignment tree of the FUT8 locus nucleotide sequence variation among several CHOK1 FUT8 knock out cell lines and CHOK1 control cell line.

Composite analysis of the sequence data is used to identify potential FUT8 knock out lines where FUT8 genomic target locus is modified through deletion and/or insertions (INDELs). The DNA sequences are then aligned to show distinct differences. FIG. 26 provides the alignment of nucleotide sequences of CHOK1 control cell line and FUT8 knock out clonal cell lines. The DNA sequence information is used to assign amino acid sequence of the FUT8 gene, exon 9 using standard codon usage. The amino acid sequences are then aligned to identify deletion, frame shift mutation, insertion of stop codons as well as amino acid substitutions at specific locations. FIG. 26 depicts the extent of nucleotide modification observed in the CHOK1 FUT8 knock out cell lines when compared to CHOK1 control cell line. The data provides a snapshot of FUT8 locus genomic DNA organization among multiple CHOK1 FUT8 knock out cell lines.

4.5—PCR Reaction

The Polymerase Chain Reaction (PCR) is a powerful and sensitive technique for DNA amplification. PCR amplifies specific DNA sequences exponentially by using multiple cycles of a three-step process. First, the double-stranded DNA template is denatured at a high temperature at 94° C. Sequence-specific primers mentioned in the Table 11 are then annealed (60.4° C.) to sites flanking the target sequence. A thermostable DNA polymerase (Phusion polymerase) extends (72° C.) the annealed primers, thereby doubling the amount of the original DNA sequence. This newly synthesized product then becomes an additional template for subsequent cycles of amplification. These three steps are repeated for 30 cycles, resulting in a $10^9$ fold increase in target DNA concentration. In order to add dATP overhangs to PCR product for cloning in TA cloning vector, the PCR Phusion polymerase amplified product is incubated with Taq polymerase for 15 minutes at 72° C.

| | | | |
|---|---|---|---|
| Initial denaturation | 94° C. | | |
| Denaturation | 94° C. | 3 minutes | 30 Cycles |
| Annealing | 60.4° C. | 50 seconds | |
| Extension | 72° C. | 1 minute | |
| Final extension | 72° C. | 10 minutes | |
| Forever | 4° C. | | |

PCR Conditions

| Reagents | Sample | Control |
|---|---|---|
| Template | respectively | 0.0 µL |
| dNTPs | 1 µL | 1 µL |
| TAL_P01_Fw | 1 µL | 1 µL |
| TAL_P01_Rv | 1 µL | 1 µL |
| Phusion Polymerase | 1 µL | 1 µL |
| Phusion buffer HF (5X) | 10 µL | 10 µL |
| Purified water | respectively | 36 µL |
| Total reaction mixture | 50 µL | 50 µL |

Figure 20:
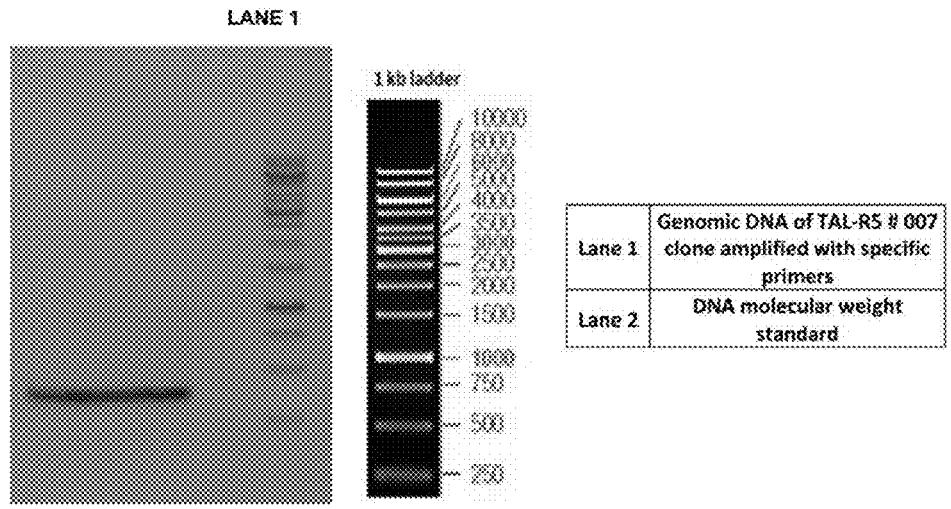
FIG. 20 depicts the PCR amplified product of sample CHOK1-TALE-R5 #007 when run on 1% agarose gel.

FIG. 20 of the present disclosure depicts representative figure of the PCR amplified product of clone CHOK1-TALE-R5 #007 when run on 1% agarose gel. Genomic DNA is isolated and amplified with TAL_P01_Fw and TAL_P01_Rv primers at standardized PCR conditions. The amplified product is electrophoresed in 1% agarose gel. The result reveals expected product size of amplified product. The PCR amplified product is gel purified and cloned in bacterial clones and sequenced to confirm the status of genomic FUT8 locus. All clonal cell lines are tested following this same process for DNA sequencing confirmation.

This representative figure describes PCR amplification of target FUT8 genomic locus using the primer sequences in Table 11 and Phusion polymerase. The PCR product is further modified with Taq DNA polymerase for tailing. Final PCR product is then electrophoresed in agarose gel for elution of amplified fragment. The "lane 1" of FIG. 20 reveals amplified PCR product of appropriate size electrophorezed for gel elution. The same process is applied to amplify PCR amplified product from CHOK1 control and FUT8 knock out CHOK1 clonal cell lines, which are gel extracted using QIAEX II Gel extraction kit.

4.6—Ligation

PCR amplified and gel eluted products are ligated in commercially available pTZ57R/T vector. Ligation protocol is described as follows Ligation Mix

| DNA (pTZ57R/T) | 1 μL |
|---|---|
| DNA (TAL(PCR product)) | 4 μL |
| T4 DNA ligase | 1 μL |
| T4 DNA ligase buffer(10X) | 1 μL |
| Purified water | to 10 μL |
| Total | 10 μL |

The above ligation mix is incubated at 4° C. overnight and 50% of ligated mix is transformed into DH5alpha or DH10B E coli competent cells by heat shock method.

4.7—Transformation of Ligated Sample into Bacterial Cell by Heat Shock Method

The purpose to transform bacterial cells is to clone and propagate the plasmid DNA. 20 μL aliquot of competent E. coli cells (DH5alpha or DH10B) are taken from −80° C. freezer and thawed on ice for 5 minutes. 50% of ligated sample (pTZ57R/T+TAL(PCR) is added to the competent cells and gently mixed and incubated on ice for 20 minutes. The mix containing tube is placed on water bath/dry bath at 42° C. for 50 seconds. The tube is placed back on ice for 2 minutes. 0.950 ml of 37° C. warmed LB broth (without ampicillin antibiotic), is incubated at 37° C., 220 rpm for 1 hour, in shaker. 100 μL of the resulting culture is spread on warmed LB+ampicillin culture plates. The plates are incubated overnight at 37° C. incubator.

4.8—Plasmid DNA Isolation from Bacterial Cells Using QIAPrep Spin Miniprep

The purpose of this procedure is to grow/culture bacteria that contain a specific DNA plasmid, which is used in following experiments. 5 mL of LB+ampicillin broth is added into autoclaved tubes, isolated bacterial colonies are inoculated from the culture plates to the LB broth+Ampicillin culture tubes. Tubes are incubated at 220 rpm, at 37° C. overnight (approximately 16-18 hours depending on the growth of the bacterium). Overnight culture of 4.5 mL is centrifuged at 13 rpm for 1 minute. Plasmid DNA is isolated using commercially available QIAGEN plasmid isolation kit. Plasmid DNA is eluted with highly pure molecular biology grade water and stored at −20° C. freezer until further use.

4.9—Positive Clones Selected Using Restriction Digestion with EcoR I-HF and Hind III-HF Enzymes Plasmid DNA thus isolated is tested for presence of insert, in this case the PCR amplified fragment. The pTZ57R/T vector contains multiple restriction enzyme sites flanking the cloned PCR product. The restriction sites EcoRI and HindIII are CHOK1sen for restriction digestion as described in below table. The reaction is carried out at 37° C. for 2 hours for complete digestion of the plasmid DNA. Following restriction digestion, the mixture is electrophoresed in 1% agarose gel for 1 hour. The PCR product insert, if present separates from pTZ57R/T vector backbone and the confirmed bacterial clones are used for DNA sequencing.

Restriction Enzyme Digestion-Reaction Mix

| DNA (pTZ57R/T + TAL(PCR products)) | 2 μg |
|---|---|
| EcoRI-HF | 1 μL |
| Hind III-HF | 1 μL |
| Cut smart buffer(10X) from New England Biolabs | 2 μL |
| Purified water | to 20 μL |
| Total | 20 μL |

Figure 21:
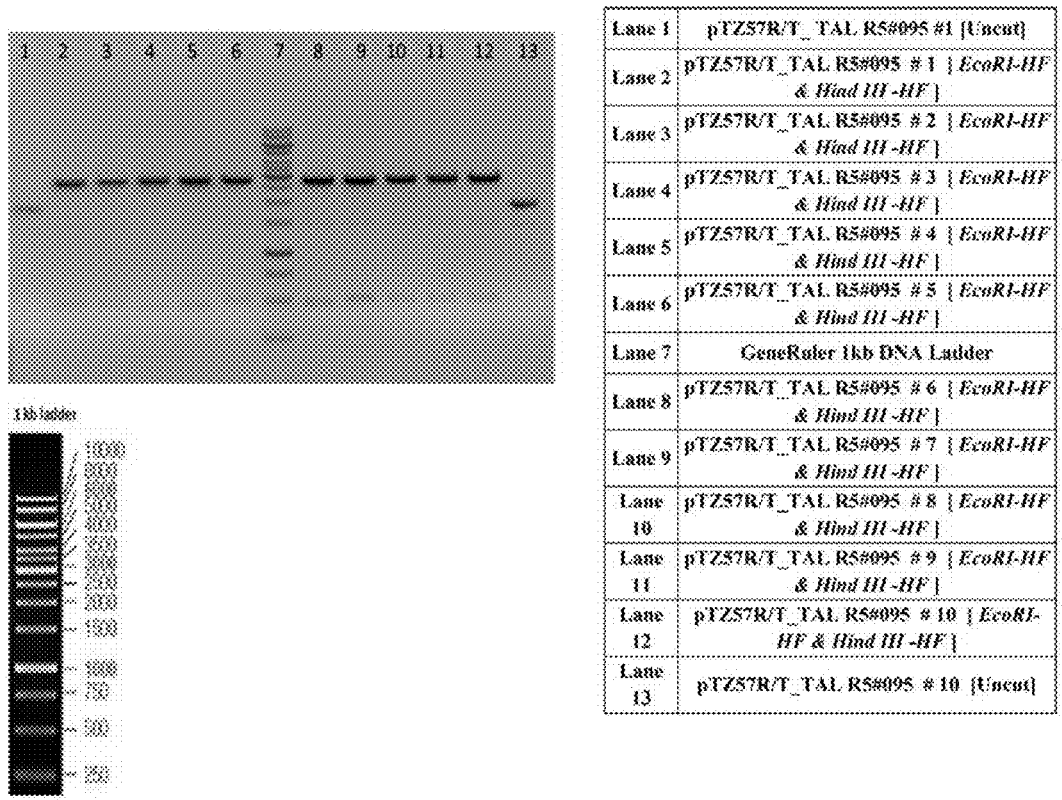
FIG. 21 depicts the restricted fragment from pTZ57R/T_TAL R5#095 (5.4 Kb+0.397 Kb) when subjected to restriction digestion and run on 1% agarose gel.

FIG. 21 of the present disclosure depicts the restriction enzyme digestion of PCR amplified product in pTZ57R/T vector to confirm presence of insert. Plasmid DNA preparations from independent bacterial clones are digested with EcoRI and HindIII restriction enzymes flanking the PCR fragment cloned in the vector and the mixture is electrophoresed in 1% agarose gel. The size of resulting DNA fragments are estimated from the DNA molecular weight standards. The results reveal that all tested clones harbor PCR product inserts of around 397 bp length. The pTZ57R/T vector backbone is represented by the fragment observed at approximately 5.4 Kb band position. Based on this data, individual plasmid DNA samples are selected and used for DNA sequencing. The same process is applied to all PCR products cloned in pTZ57R/T vector and confirmed clones are selected for DNA sequencing. The result indicates presence of insert which is sequenced with sequencing primers present in the vector backbone.

EXAMPLE 5

Confirmation of the Indels by Sequencing

DNA sequencing of the selected bacterial plasmid DNA is performed with upstream and downstream sequencing primers located in the pTZ57R/T vector backbone. Sequencing data is gathered using both primers and is analysed for proper DNA sequence information. Multiple bacterial plasmids are sequenced to generate composite DNA sequence information at the FUT8 target genomic locus for CHOK1 control cell line and clonal CHOK1 FUT8 knock out cell line achieved through TALEN constructs.

Provided below are the genomic DNA sequences from CHOK1 control cell line and CHOK1 FUT8 knock out clonal cell lines, confirming the presence of insertion and/or deletion mutations in Fut8 gene, by TALEN constructs, as per the method of the present disclosure. Amplified targeted genomic locus from each cell line including the CHOK1 control cell line is cloned as PCR products in multiple independent bacterial clones. Sequence verification is carried out with both forward and reverse sequencing primers from multiple independent bacterial clones (ranging from 5-15) to understand allelic variability of the FUT8 target locus. The DNA sequence data below is representative of genomic sequences at the targeted FUT8 locus from various FUT8 knock out cell lines.

DNA Sequence Analysis

CHOK1 control cell line (wild type)—sequence of Exon-9 is in upper case. Intron sequence is in lower case and underlined.

tgactccacttctccccagAGTCCATGTCAGACGCACTGACAAAGTGGGA
ACAGAAGCAGCCTTCCATCCCATTGAGGAATACATGGTACACGTTGAAGA -continued
ACATTTTCAGCTTCTCGAACGCAGAATGAAAGTGGATAAAAAAAGAGTGT
ATCTGGCCACTGATGACCCTTCTTTGTTAAAGGAGGCAAAGACAAAgtaa
gttagaccaacaagtg CHOK1 FUT8 knockout clonal cell line sequences are provided below. It is observed that the Exon 9 sequence is mutated in the cell lines.

Figure 22A:
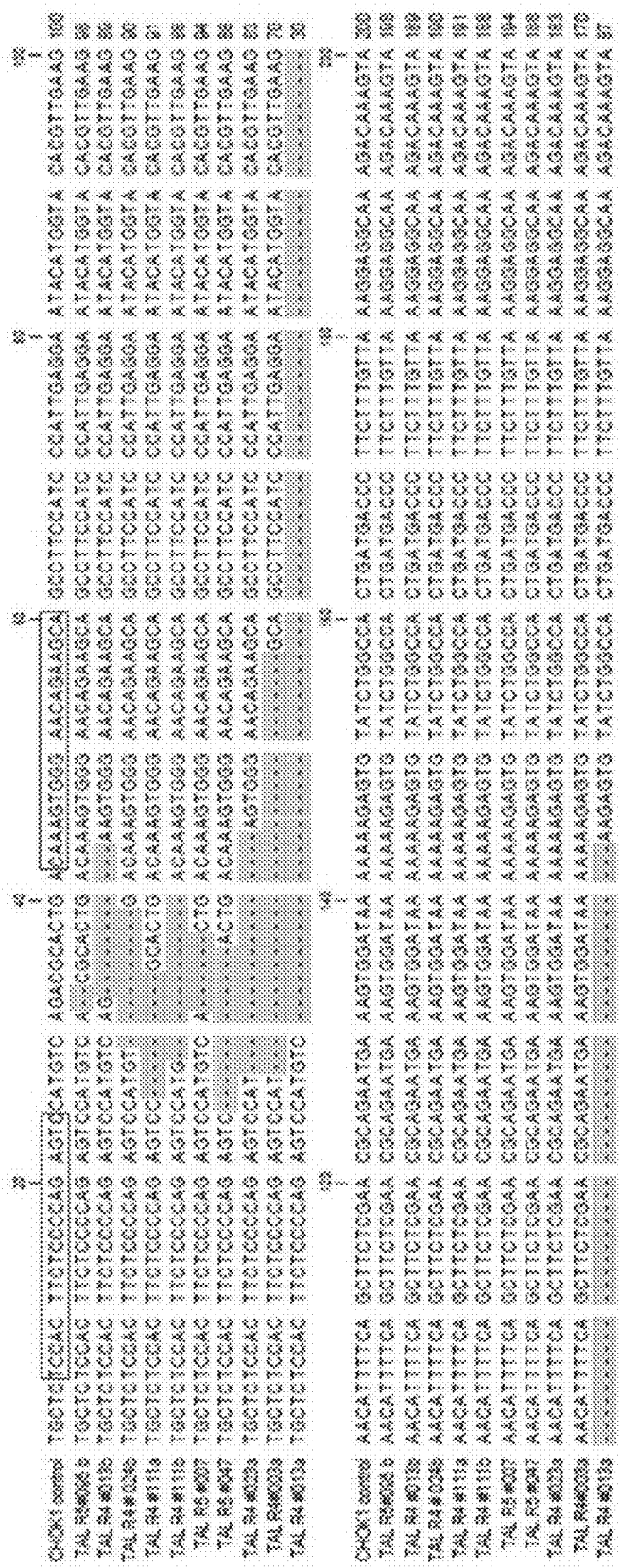
Figures 22B, 23:
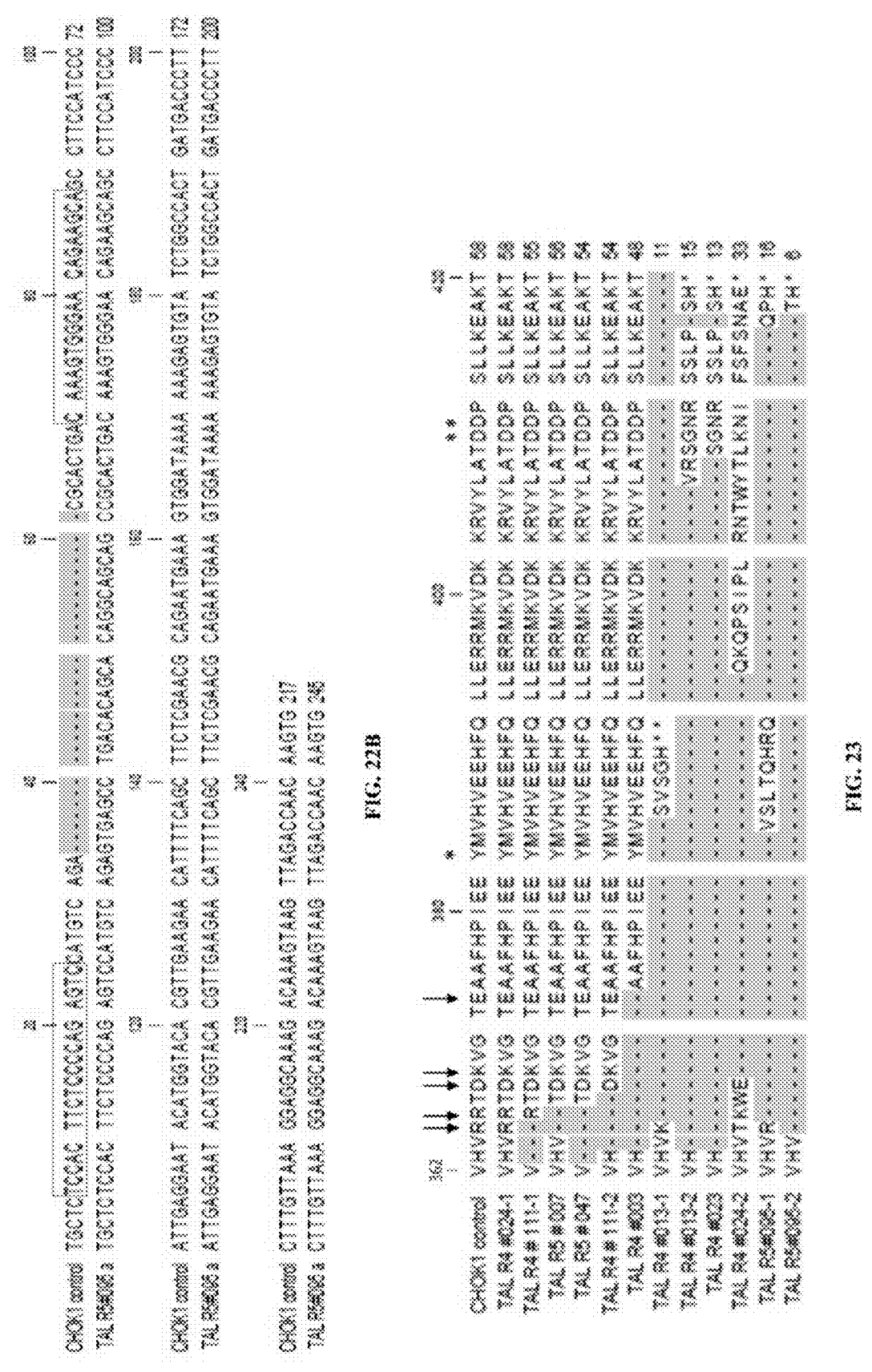

TALR4#003a-
tgctctccacttctccccagAGTCCATGCAGCCTTCCATCCCATTGAGGA
ATACATGGTACACGTTGAAGAACATTTTCAGCTTCTCGAACGCAGAATGA
AAGTGGATAAAAAAAGAGTGTATCTGGCCACTGATGACCCTTCTTTGTTA
AAGGAGGCAAAGACAAAgtaagttagaccaacaagtg TAL R4 #013a -
tgctctccacttctccccagAGTCCATGTCAAGAGTGTATCTGGCCACTG
ATGACCCTTCTTTGTTAAAGGAGGCAAAGACAAAgtaagttagaccaaca
agtg TAL R4 #013b -
tgctctccacttctccccagAGTCCATGTCAGAAGTGGGAACAGAAGCAG
CCTTCCATCCCATTGAGGAATACATGGTACACGTTGAAGAACATTTTCAG
CTTCTCGAACGCAGAATGAAAGTGGATAAAAAAAGAGTGTATCTGGCCAC
TGATGACCCTTCTTTGTTAAAGGAGGCAAAGACAAAgtaagttagaccaa
caagtg TAL R4 #023a -
tgctctccacttctccccagAGTCCATAGTGGGAACAGAAGCAGCCTTCC
ATCCCATTGAGGAATACATGGTACACGTTGAAGAACATTTTCAGCTTCTC
GAACGCAGAATGAAAGTGGATAAAAAAAGAGTGTATCTGGCCACTGATGA
CCCTTCTTTGTTAAAGGAGGCAAAGACAAAgtaagttagaccaacaagtg TAL R4 #024b -
tgctctccacttctccccagAGTCCATGTGACAAAGTGGGAACAGAAGCA
GCCTTCCATCCCATTGAGGAATACATGGTACACGTTGAAGAACATTTTCA
GCTTCTCGAACGCAGAATGAAAGTGGATAAAAAAAGAGTGTATCTGGCCA
CTGATGACCCTTCTTTGTTAAAGGAGGCAAAGACAAAgtaagttagacca
acaagtg TALR4#111a--
tgctctccacttctccccagAGTCCGCACTGACAAAGTGGGAACAGAAGC
AGCCTTCCATCCCATTGAGGAATACATGGTACACGTTGAAGAACATTTTC
AGCTTCTCGAACGCAGAATGAAAGTGGATAAAAAAAGAGTGTATCTGGCC
ACTGATGACCCTTCTTTGTTAAAGGAGGCAAAGACAAAgtaagttagacc
aacaagtg TAL R4 #111b -
tgctctccacttctccccagAGTCCATGACAAAGTGGGAACAGAAGCAGC
CTTCCATCCCATTGAGGAATACATGGTACACGTTGAAGAACATTTTCAGC
TTCTCGAACGCAGAATGAAAGTGGATAAAAAAAGAGTGTATCTGGCCACT
GATGACCCTTCTTTGTTAAAGGAGGCAAAGACAAAgtaagttagaccaac
aagtg -continued
TAL R5 #007 a -
tgctctccacttctccccagAGTCCATGTCACTGACAAAGTGGGAACAGA
AGCAGCCTTCCATCCCATTGAGGAATACATGGTACACGTTGAAGAACATT
TTCAGCTTCTCGAACGCAGAATGAAAGTGGATAAAAAAAGAGTGTATCTG
GCCACTGATGACCCTTCTTTGTTAAAGGAGGCAAAGACAAAgtaagttag
accaacaagtg TAL R5 #047 a -
tgctctccacttctccccagAGTCACTGACAAAGTGGGAACAGAAGCAGC
CTTCCATCCCATTGAGGAATACATGGTACACGTTGAAGAACATTTTCAGC
TTCTCGAACGCAGAATGAAAGTGGATAAAAAAAGAGTGTATCTGGCCACT
GATGACCCTTCTTTGTTAAAGGAGGCAAAGACAAAgtaagttagaccaac
aagtg TAL R5#095 a -
tgctctccacttctccccagAGTCCATGTCAGAGTGAGCCTGACACAGCA
CAGGCAGCAGCCGCACTGACAAAGTGGGAACAGAAGCAGCCTTCCATCCC
ATTGAGGAATACATGGTACACGTTGAAGAACATTTTCAGCTTCTCGAACG
CAGAATGAAAGTGGATAAAAAAAGAGTGTATCTGGCCACTGATGACCCTT
CTTTGTTAAAGGAGGCAAAGACAAAgtaagttagaccaacaagtg TAL R5#095 b -
tgctctccacttctccccagAGTCCATGTCACGCACTGACAAAGTGGGAA
CAGAAGCAGCCTTCCATCCCATTGAGGAATACATGGTACACGTTGAAGAA
CATTTTCAGCTTCTCGAACGCAGAATGAAAGTGGATAAAAAAAGAGTGTA
TCTGGCCACTGATGACCCTTCTTTGTTAAAGGAGGCAAAGACAAAgtaag
ttagaccaacaagtg Representative genomic DNA sequence alignment in FKO cell line clones showing deletion in FUT8 gene sequence is provided in FIGS. 22A and 22B of the present disclosure. FIGS. 22A and 22B depict nucleotide sequence analysis. Genomic DNA of TALEN transfected selected CHOK1 FUT8 knock out clones and CHOK1 control cell lines are used to PCR amplify targeted genomic FUT8 locus. Sequence data is collected from analysis of 5-15 independent bacterial clones sequenced with both forward and reverse sequencing primers. The sequencing data suggests deletions of variable lengths in multiple clones compared to CHOK1 control cell line. Largest deletion of 113 bases is observed in clone TAL R4#013 and smallest deletion is just 2 bases in clone TAL R5#095. All deletions are located at the TALEN target site. In FIG. 22B, the left and right TALEN DNA binding sites are denoted by open boxes. FIG. 22B indicates one allele of the clone TAL R5#095a where the sequence data revealed insertion of new DNA sequence compared to CHOK1 control cell line.

The data suggests various INDELs present at the FUT8 genomic locus in CHOK1 FUT8 knock out cell lines. In many cases, it is observed that there are very specific modifications at the targeted bases, and in other cases the changes are broad and involve longer stretches of DNA. Such diversity of genomic modification through TALEN constructs is possible due to endogenous DNA double strand break repair through non homologous end joining. All of these cell lines are selected through two separate functional screening assays, namely LCA media selection assay and LCA-FITC flow cytometry assay. The results also imply high efficiency of both these functional assays to isolate and identify CHOK1 FUT8 knock out cell line.

It is also revealed that the design of the TALEN construct depicted in this disclosure is unique as this one pair of TALEN constructs provided a highly sequence specific gene alteration at the targeted FUT8 locus in CHOK1 cell lines.

Amino Acid Sequence Analysis of the CHOK1 FUT8 Knock Out Cell Lines

FUT8 genomic DNA sequence CHOK1 control and CHOK1 FUT8 knock out cell lines are further analysed to understand the impact of DNA sequence INDEL on FUT8 protein status. DNA sequences at the targeted FUT8 locus is translated into amino acid sequences using vertebrate codon bias. The amino acid sequence of exon9 region is studied closely and the results are summarized in table 12. When compared to CHOK1 control cell line, the FUT8 knock out cell lines revealed modifications including deletions as small as 3 amino acids (TAL-R4 #111) to as large as 10 amino acids (TAL R4 #003) are deleted in FUT8 knock out cell lines.

In many instances, frame shift mutations are observed, which alter the C-terminal region of the FUT8 protein to make it non-functional enzyme. In addition, in several cases stop codon is introduced as an effect of frame shift mutation and thereby the FUT8 protein is truncated and non-functional in these clones (TAL R4 #013 and TAL R4 #023).

Representative amino acid sequence alignment in CHOK1 control and CHOK1 FUT8 knock out cell lines showing deletion in FUT8 gene sequence is provided in FIG. 23 of the present disclosure. The translated amino acid sequence is predicted using standard codon usage. The data indicates various effects on FUT8 amino acid sequence due to the nucleotide deletion and/or insertion observed. Black arrows indicate amino acids critical for FUT8 functionality targeted in this disclosure. Other important amino acids in Exon9 region are indicated by asterisks. Clone TAL R4#111, TAL R5#007, TAL R5#047 and TAL R4#003 revealed targeted deletion of specific amino acid position at Arg366 in addition to other amino acids in the region. Remaining clones revealed deletion followed by frame shift mutations resulting in early stop codons. All these modifications indicate non-functional FUT8 protein in the TALEN transfected CHOK1 FUT8 knock out cell lines.

In addition, the TALEN construct created frame shift mutations which disrupted the c-terminal region of the FUT8 enzyme which contains important motif II and motif III along with the specific amino acids positions Tyr-382, Asp-409, Asp-410, Asp-453, and Ser-469 which are involved in the catalytic domain of the FUT8 enzyme. The end result of these critical mutations is non-functional α-1,6 fucosyltransferase enzyme, the protein product of FUT8 gene in the CHOK1 FUT8knock out cell lines.

TABLE 12

| Cell line information | Genetic makeup at FUT8 target genomic locus | Amino acid sequence derived from DNA sequencing data |
|---|---|---|
| CHOK1 control cell line | Wild type FUT8 amino acid sequence | VHVRRTDKVGTEAAFHPIEEYMVHVEEHFQL LERRMKVDKKRVYLATDDPSLLKEAKT |
| TAL R4 #003 | Deletion mutant and Wild type allele | 1. VH_AAFHPIEEYMVHVEEHFQLLERRMKVD KKRVYLATDDPSLLKEAKT 2. VHVRRTDKVG TEAAFHPIEEYMVHVEEHFQLLERRMKVDKK RVYLATDDPSLLKEAKT |
| TAL R4 #013 | Frame shift mutation with stop codons | 1. VHVKSVSGH** 2. VHVRSGNRSSLPSH* |
| TAL R4 #023 | Frame shift mutation with stop codons | VHSGNRSSLPSH* |
| TAL R4 #024 | Wild type allele and frame shift mutation with stop codon | 1. VHVRRTDKVGTEAAFHPIEEYMVHVEEHFQ LLERRMKVDKKRVYLATDDPSLLKEAKT 2. VHVTKWEQKQPSIPLRNTWYTLKNIFSFSN AE* |
| TAL R4 # 111 | Different length deletion at the targeted amino acid position | 1. V_RTDKVGTEAAFHPIEEYMVHVEEHFQLL ERRMKVDKKRVYLATDDPSLLKEAKT 2. VH__DKVGTEAAFHPIEEYMVHVEEHFQLL ERRMKVDKKRVYLATDDPSLLKEAKT |
| TAL R5 # 007 | Deletion at targeted amino acid positions | VHV___TDKVGTEAAFHPIEEYMVHVEEHFQL LERRMKVDKKRVYLATDDPSLLKEAKT |
| TAL R5 # 047 | Deletion at targeted amino acid positions | V____TDKVGTEAAFHPIEEYMVHVEEHFQL LERRMKVDKKRVYLATDDPSLLKEAKT |
| TAL R5#095 | Frame shift mutation with stop codons | 1. VHVRVSLTQHRQQPH* 2. VHVTH* |

Furthermore, it is observed that the selection of target amino acids in the FUT8 protein sequence is highly effective. Targeting conserved amino acids at Arg 365, Arg 366, Asp-368, Lys-369, and Glu-373 positions of wild type FUT8 protein with only one pair of TALEN construct has created mutations at the targeted locus in multiple knock out cell lines.

EXAMPLE 7

Use of Fucose Knockout Cell Line to Produce Non-Fucosylated Antibodies

The fucose knock out CHOK1 cell expression platform is used for expression of non-fucosylated antibody, particularly non-fucosylated monoclonal antibody. Antibody genes encoding heavy chain and light chain of monoclonal antibody is cloned in suitable gene expression plasmids and is transfected in the fucose knock out CHOK1 cell platform described in the examples above. The monoclonal antibody produced using this platform/method is expressed as non-fucosylated antibody. The product is purified following established protocols and guidelines to develop biobetter monoclonal antibody product for therapeutic use. Nonfucosylated biobetter antibody produced using this platform results in higher level of ADCC and thereby better therapeutic outcome.

LCA-FITC flow cytometry data and further sequencing experiments of the present disclosure confirm that the FKO lines are unable to fucosylate membrane proteins. Thus, the cell obtained in the present disclosure produces non-fucosylated proteins, specifically non-fucosylated antibody. The characteristic features and therapeutic advantages of non-fucosylated antibodies, such as higher ADCC, are known to one of skill in the art.

Although disclosure and exemplification has been provided by way of illustrations and examples for the purpose of clarity and understanding, it is apparent to a person skilled in the art that various changes and modifications can be practiced without departing from the spirit or scope of the disclosure. Accordingly, the foregoing descriptions and examples should not be construed as limiting the scope of the present disclosure.

It is intended that the scope of the disclosure be limited not by this detailed description, but rather by the claims appended hereto. It is also to be understood that the following claims are intended to cover all of the generic and specific features of the disclosure described herein.

Many modifications and variations are possible in light of the above teachings. It is therefore to be understood that the claimed subject matter may be practiced otherwise than as specifically described. Any reference to claim elements in the singular, for example, using the articles "a," "an," "the," or "said" is not to be construed as limiting the disclosure.

The description of the embodiments of the present disclosure reveals the general nature of the embodiments that are readily suitable for modification and/or adaptation for various applications by applying the current knowledge. Such specific embodiments of the disclosure, without departing from the generic concept, and, therefore, such adaptations and modifications should and are intended to be comprehended and considered within the meaning and range of equivalents of the disclosed embodiments.

It is also to be understood that the phrases or terms employed herein are for the purpose of description and not intended to be of any limitation. Throughout the present disclosure, the word "comprise", or variations such as "comprises" or "comprising" wherever used, are to be understood to imply the inclusion of a stated element, integer or step, or group of elements, integers or steps, but not the exclusion of any other element, integer or step, or group of elements, integers or steps.

Where a numerical limit or range is stated herein, the endpoints are included. Also, values and sub-ranges within a numerical limit or range are specifically included as if explicitly written out.

With respect to the use of any plural and/or singular terms in the present disclosure, those of skill in the art can translate from the plural to the singular and/or from the singular to the plural as is considered appropriate to the context and/or application. The various singular/plural permutations may be expressly set forth herein for the sake of clarity.

Any discussion of documents, acts, materials, devices, articles and the like that has been included in this specification is solely for the purpose of providing a context for the present disclosure. It is not to be taken as an admission that any or all of these matters form a part of the prior art base or are common general knowledge in the field relevant to the present disclosure, as it existed anywhere before the priority date of this application.

The contents of all references, patents, and published patent applications cited throughout this application are incorporated herein by reference for all purposes.

---

We claim:

1. A DNA-binding domain of Transcription Activator like Effector Nuclease protein, wherein the DNA-binding domain comprises one or more amino acid sequence selected from the group consisting of SEQ ID No. 6, SEQ ID No.8, SEQ ID No. 11, SEQ ID No. 14, SEQ ID No. 17, SEQ ID No.20, SEQ ID No. 23, SEQ ID No.26, SEQ ID No. 29, SEQ ID No.32, SEQ ID No. 35, and SEQ ID No.38.

2. The DNA-binding domain as claimed in claim 1, wherein SEQ ID No. 6 binds SEQ ID No. 4 of the Fut8 gene sequence,
   SEQ ID No. 8 binds SEQ ID No. 5 of the Fut8 gene sequence,
   SEQ ID No. 11 binds SEQ ID No. 10 of the Fut8 gene sequence,
   SEQ ID No. 14 binds SEQ ID No. 13 of the Fut8 gene sequence,
   SEQ ID No. 17 binds SEQ ID No. 16 of the Fut8 gene sequence,
   SEQ ID No. 20 binds SEQ ID No. 19 of the Fut8 gene sequence,
   SEQ ID No. 23 binds SEQ ID No. 22 of the Fut8 gene sequence,
   SEQ ID No. 26 binds SEQ ID No. 25 of the Fut8 gene sequence,
   SEQ ID No. 29 binds SEQ ID No. 28 of the Fut8 gene sequence,
   SEQ ID No. 32 binds SEQ ID No. 31 of the Fut8 gene sequence,
   SEQ ID No. 35 binds SEQ ID No. 34 of the Fut8 gene sequence,
   SEQ ID No. 38 binds SEQ ID No. 37 of the Fut8 gene sequence.

3. A polynucleotide encoding the DNA-binding domain of claim 1, wherein the polynucleotide comprises one or more nucleotide sequence selected from the group consisting of SEQ ID No. 7, SEQ ID No. 9, SEQ ID No. 12, SEQ ID No. 15, SEQ ID No. 18, SEQ ID No. 21, SEQ ID No. 24, SEQ ID No. 27, SEQ ID No. 30, SEQ ID No. 33, SEQ ID No. 36, and SEQ ID No. 39.

4. A Transcription Activator like Effector Nuclease protein comprising the DNA-binding domain as claimed in claim 1 and nuclease.

5. The Transcription Activator like Effector Nuclease protein as claimed in claim 4, wherein the nuclease is Fok1 endonuclease.

6. A vector comprising a polynucleotide as claimed in claim 3.

7. A cell comprising a vector as claimed in claim 6.

8. The cell as claimed in claim 7, wherein the cell is a mammalian cell.

9. A method of obtaining a cell without fucosylation activity, said method comprising steps of:
   a) Obtaining a Transcription Activator like Effector Nuclease construct comprising polynucleotide as claimed in claim 3; and
   b) Transfecting a cell with the construct of step (a) to obtain a cell without fucosylation activity.

10. A method of obtaining non-fucosylated protein, said method comprising steps of:
    a) Obtaining a Transcription Activator like Effector Nuclease construct comprising polynucleotide as claimed in claim 3;
    b) Transfecting a cell with the construct of step (a) to obtain a cell without fucosylation activity; and
    c) Obtaining non-fucosylated protein expressed by the cell of step (b).

11. The method as claimed in claim 10, wherein the non-fucosylated protein is a non-fucosylated antibody.

12. The method as claimed in claim 11, wherein the non-fucosylated antibody is a non-fucosylated monoclonal antibody.

13. The method as claimed in claim 10, wherein the Transcription Activator like Effector Nuclease is the nuclease protein as claimed in claim 4; and wherein the nuclease protein cleaves Fut8 gene sequence.

14. The method as claimed in claim 13, wherein the Fut8 gene sequence coding for α-1,6 Fucosyltransferase enzyme is cleaved at Exon 9.

15. The method as claimed in claim 14, wherein the Fucosyltransferase enzyme is mutated at one or more amino acid position selected from the group consisting of Arg-365, Arg-366, Asp-368, Lys-369, Glu-373, Tyr-382, Asp-409, Asp-410, Asp-453, and Ser-469.

16. The method as claimed in claim 10, wherein the cell is a mammalian cell, and wherein the cell is Chinese Hamster Ovary cell.

17. The method as claimed in claim 10, wherein the cell produces an endogenous non-fucosylated protein.

18. The method as claimed in claim 10, further comprising a step of introducing a protein encoding gene into the cell and obtaining non-fucosylated protein.

19. A non-fucosylated protein obtained by the method as claimed in claim 10.

20. The non-fucosylated protein as claimed in claim 19, wherein the protein is a non-fucosylated antibody.

21. A composition comprising the non-fucosylated protein of claim 19, optionally along with pharmaceutically acceptable excipient.

22. The composition as claimed in claim 21, wherein the non-fucosylated protein is a non-fucosylated antibody.

23. The method as claimed in claim 9, wherein the Transcription Activator like Effector Nuclease is the nuclease protein as claimed in claim 15; and wherein the nuclease protein cleaves Fut8 gene sequence.

24. The method as claimed in claim 9, wherein the cell is mammalian cell, and wherein the mammalian cell is Chinese Hamster Ovary cell.

\* \* \* \* \*

UNITED STATES PATENT AND TRADEMARK OFFICE
CERTIFICATE OF CORRECTION

Page 1 of 1

PATENT NO. : 10,077,434 B2
APPLICATION NO. : 15/500509
DATED : September 18, 2018
INVENTOR(S) : Sohang Chatterjee et al.

It is certified that error appears in the above-identified patent and that said Letters Patent is hereby corrected as shown below:

On the Title Page

Item (72), Line 8, in the list of Inventors, remove "Jahnabi Arika" and replace it with --Jahnabi Hazarika--

Signed and Sealed this
Seventh Day of May, 2019

Andrei Iancu
*Director of the United States Patent and Trademark Office*